US008268756B2

(12) United States Patent
Logtenberg et al.

(10) Patent No.: US 8,268,756 B2
(45) Date of Patent: Sep. 18, 2012

(54) MIXTURE OF BINDING PROTEINS

(75) Inventors: Ton Logtenberg, Driebergen (NL); Hendricus Renerus Jacobus Mattheus Hoogenboom, Maastricht (NL)

(73) Assignee: Merus B.V., Driebergen (NL)

( * ) Notice: Subject to any disclaimer, the term of this patent is extended or adjusted under 35 U.S.C. 154(b) by 92 days.

(21) Appl. No.: 11/490,545

(22) Filed: Jul. 20, 2006

(65) Prior Publication Data

US 2007/0059766 A1 Mar. 15, 2007

Related U.S. Application Data

(63) Continuation of application No. PCT/NL2005/000036, filed on Jan. 19, 2005.

(30) Foreign Application Priority Data

Jan. 20, 2004 (EP) .................................... 04075170

(51) Int. Cl.
C40B 50/06 (2006.01)
C07H 21/04 (2006.01)

(52) U.S. Cl. ................ 506/26; 506/23; 506/13; 435/7.1; 435/325; 435/455

(58) Field of Classification Search ..................... 506/26, 506/23, 13; 435/7.1, 325, 455
See application file for complete search history.

(56) References Cited

U.S. PATENT DOCUMENTS

| 4,399,216 A | 8/1983 | Axel et al. |
|---|---|---|
| 4,599,311 A | 7/1986 | Kawasaki |
| 4,634,665 A | 1/1987 | Axel et al. |
| 4,801,687 A | 1/1989 | Ngo |
| 4,816,567 A | 3/1989 | Cabilly et al. |
| 4,868,103 A | 9/1989 | Stavrianopoulos et al. |
| 4,937,190 A | 6/1990 | Palmenberg et al. |
| 5,137,809 A | 8/1992 | Loken et al. |
| 5,179,017 A | 1/1993 | Axel et al. |
| 5,223,409 A | 6/1993 | Ladner et al. |
| 5,627,037 A | 5/1997 | Ward et al. |
| 5,631,169 A | 5/1997 | Lakowicz et al. |
| 5,641,640 A | 6/1997 | Hanning |
| 5,667,988 A | 9/1997 | Barbas et al. |

(Continued)

FOREIGN PATENT DOCUMENTS

CA 2 405 961 11/2001

(Continued)

OTHER PUBLICATIONS

Journal of Immunological Methods 231, 53-63, 1999.*

(Continued)

*Primary Examiner* — T. D. Wessendorf
(74) *Attorney, Agent, or Firm* — TraskBritt

(57) ABSTRACT

Described are methods for producing libraries of cells expressing at least two separate single polypeptide chain binding proteins, in which the binding proteins have different target epitopes. Such libraries are made by integration of the nucleic acid sequences encoding the polypeptide chains into the genome of the host cell, and selecting for cells that have successfully integrated these nucleic acids. The selected cells are preferably subjected to a cloning step. Mixtures of binding proteins are produced without having to individually produce each of the components of the mixture. A library of cells wherein essentially each cell encodes at least two single polypeptide chain binding proteins having different target epitopes is also herewith provided, as well as methods for producing a composition comprising at least two separate single polypeptide chain binding proteins having different target epitopes.

8 Claims, 11 Drawing Sheets

U.S. PATENT DOCUMENTS

| | | | |
|---|---|---|---|
| 5,733,779 | A | 3/1998 | Reff |
| 5,772,997 | A | 6/1998 | Hudziak et al. |
| 5,783,186 | A | 7/1998 | Arakawa et al. |
| 5,789,208 | A | 8/1998 | Sharon |
| 5,888,789 | A | 3/1999 | Rodriquez |
| 5,965,371 | A | 10/1999 | Marasco et al. |
| 6,004,940 | A | 12/1999 | Marasco et al. |
| 6,080,560 | A | 6/2000 | Russell et al. |
| 6,180,357 | B1 | 1/2001 | Young et al. |
| 6,207,446 | B1 | 3/2001 | Szostak et al. |
| 6,265,150 | B1 | 7/2001 | Terstappan et al. |
| 6,291,740 | B1 | 9/2001 | Bremel et al. |
| 6,303,341 | B1 | 10/2001 | Hiatt et al. |
| 6,335,163 | B1 | 1/2002 | Sharon |
| 7,067,284 | B1 | 6/2006 | Barbas et al. |
| 7,262,028 | B2 | 8/2007 | Van Berkel et al. |
| 7,429,486 | B2 | 9/2008 | Van Berkel et al. |
| 7,491,516 | B2 * | 2/2009 | Collinson et al. ........... 435/70.21 |
| 2003/0039958 | A1 * | 2/2003 | Holt et al. .......................... 435/5 |
| 2003/0091561 | A1 | 5/2003 | van de Winkel et al. |
| 2003/0194403 | A1 | 10/2003 | van de Winkel et al. |
| 2003/0207346 | A1 | 11/2003 | Arathoon et al. |
| 2003/0224408 | A1 | 12/2003 | Hoogenboom et al. |
| 2006/0160184 | A1 | 7/2006 | Hoogenboom et al. |
| 2007/0054362 | A1 | 3/2007 | Van Berkel et al. |
| 2009/0263864 | A1 | 10/2009 | Van Berkel et al. |

FOREIGN PATENT DOCUMENTS

| | | | |
|---|---|---|---|
| CA | 1 341 364 | | 6/2002 |
| CA | 2 445 255 | | 10/2002 |
| CA | 2 114 353 | | 1/2006 |
| EP | 0 120 694 | | 10/1984 |
| EP | 0 314 161 | | 5/1989 |
| EP | 0 402 029 | | 12/1990 |
| EP | 0 445 625 | | 9/1991 |
| EP | 0 469 897 | A2 | 2/1992 |
| EP | 0 481 790 | | 4/1992 |
| EP | 0 523 949 | | 1/1993 |
| EP | 0 724 639 | | 1/2001 |
| EP | 1 325 932 | B1 | 4/2005 |
| WO | WO 90/02809 | | 3/1990 |
| WO | WO 91/08216 | | 6/1991 |
| WO | WO 91/17271 | | 11/1991 |
| WO | WO 92/01047 | | 1/1992 |
| WO | WO 92/09690 | | 6/1992 |
| WO | WO 92/15679 | | 9/1992 |
| WO | WO 92/18619 | | 10/1992 |
| WO | WO 92/20791 | | 11/1992 |
| WO | WO 93/01288 | | 1/1993 |
| WO | WO 94/02610 | | 2/1994 |
| WO | WO 94/25591 | | 11/1994 |
| WO | WO 95/17085 | | 6/1995 |
| WO | WO 95/17500 | | 6/1995 |
| WO | WO 95/20401 | | 8/1995 |
| WO | WO 96/27011 | | 9/1996 |
| WO | WO 97/42313 | | 11/1997 |
| WO | WO 97/47739 | | 12/1997 |
| WO | WO 98/15627 | | 4/1998 |
| WO | WO 98/15833 | | 4/1998 |
| WO | WO 98/39416 | | 9/1998 |
| WO | WO 98/41645 | | 9/1998 |
| WO | WO 98/50431 | | 11/1998 |
| WO | WO 99/20749 | | 4/1999 |
| WO | WO 99/23221 | * | 5/1999 |
| WO | WO 99/36569 | | 7/1999 |
| WO | WO 99/64582 | | 12/1999 |
| WO | WO 00/63403 | | 10/2000 |
| WO | WO 00/70023 | | 11/2000 |
| WO | WO 00/71694 | A1 | 11/2000 |
| WO | WO 01/19394 | | 3/2001 |
| WO | WO 01/27279 | | 4/2001 |
| WO | WO 01/32901 | | 5/2001 |
| WO | WO 01/48485 | | 7/2001 |
| WO | WO 01/64929 | | 9/2001 |
| WO | WO 01/88132 | A2 | 11/2001 |
| WO | WO 02/18948 | | 3/2002 |
| WO | WO 02/46233 | A1 | 6/2002 |
| WO | WO 02/074969 | A2 | 9/2002 |
| WO | WO 02/096948 | A2 | 12/2002 |
| WO | WO 03/004704 | | 1/2003 |
| WO | WO 03/016501 | A2 | 2/2003 |
| WO | WO 03/048306 | A2 | 6/2003 |
| WO | WO 03/102157 | A2 | 12/2003 |
| WO | WO 2004/009618 | | 1/2004 |
| WO | WO 2004/106375 | A1 | 12/2004 |
| WO | WO 2005/068622 | A2 | 7/2005 |

OTHER PUBLICATIONS

Muyldermans, Reviews in Molecular Biotechnology 74 (2001) 277-302.*

Ward et al, Nature, vol. 341, 1989, 544-546.*

PCT International Search Report, PCT/NL2005/000036, dated Jan. 19, 2005.

Holliger et al., "Diabodies": Small bivalent and bispecific antibody fragments, Proc. Natl. Acad. Sci., Jul. 1993, pp. 6444-6448, vol. 90.

Kortt et al., Dimeric and trimeric antibodies: high avidity scFvs for cancer targeting, Biomol. Eng., Oct. 15, 2001, pp. 95-108, vol. 18, No. 3.

De Kruif et al., Rapid selection of cell subpopulation-specific human monoclonal antibodies from a synthetic phage antibody library, Proc. Natl. Acad. Sci., USA, Apr. 1995, pp. 3938-3942, vol. 92.

Schmitz et al., Phage Display: A Molecular Tool for the Generation of Antibodies—A Review, Placenta, 2000, pp. S106-S112, Supplement A, Trophoblast Research, vol. 14.

Office Action in U.S. Appl. No. 11/593,280 dated Apr. 28, 2008.

Office Action in U.S. Appl. No. 11/593,280 dated Oct. 29, 2008.

Office Action in U.S. Appl. No. 11/593,280 dated Apr. 17, 2009.

U.S. Appl. No. 11/593,280, filed Nov. 6, 2006 Recombinant Production of Mixtures of Antibodies.

U.S. Appl. No. 11/977,954, filed Oct. 26, 2007 Chimaeric Phages.

U.S. Appl. No. 12/221,021, filed Jul. 29, 2008 Recombinant Production of Mixtures of Antibodies.

Boel et al., Functional human monoclonal antibodies of all isotypes constructed from phage display library-derived single-chain Fv antibody fragments, Journal of Immunological Methods, 2000, pp. 153-166, vol. 239.

de Kruif et al., Selection and Application of Human Single Chain Fv Antibody Fragments from a Semi-synthetic Phage Antibody Display Library with Designed CDR3 Regions, Journal of Molecular Biology, 1995, pp. 97-105, vol. 248.

Figini et al., In Vitro Assembly of Repertoires of Antibody Chains on the Surface of Phage by Renaturation, Journal of Molecular Biology, 1994, pp. 68-78, vol. 239.

Franconi et al., Functional expression in bacteria and plants of an scFv antibody fragment against tospoviruses, Immunotechnology, 1999, pp. 189-201, vol. 4.

French, et al., Cancer Research, 1991, pp. 2353-2361, vol. 51.

Lindhofer et al., Preferential Species-Restricted Heavy/Light Chain Pairing in Rat/Mouse Quadromas, Journal of Immunology, 1995, pp. 219-225, vol. 155.

Ma et al., Assembly of monoclonal antibodies with IgG1 and IgA heavy chain domains in transgenic tabacco plants, Eur. J. Immunol., 1994, p. 131-138, vol. 24.

Merchant et al., An efficient route to human bispecific IgG, Nature Biotechnology, Jul. 1998, pp. 677-681, vol. 16.

Morrison, Sherie L., Transfectomas Provide Novel Chimeric Antibodies, Science, Sep. 20, 1985, pp. 1202-1207, vol. 229.

Pau et al, The human cell line PER.C6 provides a new manufacturing system for the production of influenza vaccines, Vaccine, 2001, pp. 2716-2712, vol. 19.

PCT International Preliminary Examination Report, PCT/EP03/07690, dated Nov. 11, 2004.

PCT International Search Report, PCT/EP03/07690, dated Apr. 16, 2004.

Sugita, et al., Int. J. Cancer, 1986, pp. 351-357, vol. 37.

Vaughan et al., Human Antibodies with Sub-nanomolar Affinities Isolated from a Large Non-immunized Phage Display Library, Nature Biotechnology, Mar. 1996, pp. 309-314, vol. 14.

Warnaar et al., Hybridoma, 1994, pp. 519-526, vol. 13, No. 6.

Burioni et al., Nonneutralizing Human Antibody Fragments against Hepatitis C Virus E2 Glycoprotein Modulate Neutralization of Binding Activity of Human Recombinant Fabs, Abstract, Virology, Sep. 2001, pp. 29-35, vol. 288, No. 1.

Champion et al., Abstract, The development of monoclonal human rabies virus-neutralizing antibodies as a substitute for pooled human immune globulin in the prophylactic treatment of rabies virus exposure, Abstract, Journal of Immunological Methods, Feb. 2000, pp. 81-90, vol. 235, No. 1-2, Elsevier Science Publishers B.V., Amsterdam, NL.

Chen et al., Abstract, Selection and analysis of an optimized anti-VEGF antibody: crystal structure of an affinity-matured Fab in complex with antigen, Journal of Molecular Biology, Nov. 5, 1999, pp. 865-881, vol. 293, No. 4.

Heintges et al., Cloning, Bacterial Expression and Sequencing of Human Antibody Fragments Against Hepatitis C Virus NS3 by Phage Display of a Combinatorial Phagemid Library, Hepatology, p. 497, vol. 28, No. 4.

Hoogenboom et al., Antibody phage display technology and its applications, Immunotechnology, 1998, pp. 1-20, vol. 4.

Huse et al., Purification of antibodies by affinity chromatography, Journal of Biochemical and Biophysical Methods, 2002, pp. 217-231, vol. 51.

Kang et al., Linkage of recognition and replication functions by assembling combinatorial antibody Fab libraries along phage surfaces, Proc. Natl. Acad. Sci., May 1991, pp. 4363-4366, vol. 88.

Krebs et al., High-throughput generation and engineering of recombinant human antibodies, Journal of Immunological Methods, 2001, pp. 67-84, vol. 254.

Kwaks et al., Identification of anti-repressor elements that confer high and stable protein production in mammalian cells, Nature Biotechnology, 2003, pp. 553-558, vol. 269.

Lu et al., Selection of high affinity human neutralizing antibodies to VEGFR2 from a large antibody phage display library for antiangiogenesis therapy, Abstract, International Journal of Cancer, Jan. 20, 2002, pp. 393-399, vol. 97, No. 3.

Norderhaug et al., Balanced expression of single subunits in a multisubunit proteins, achieved by cell fusion of individual transfectants, European Journal of Biochemistry, 2002, pp. 3205-3210, vol. 269.

PCT International Search Report, PCT/NL2004/000386 dated Nov. 23, 2004.

Sidhu et al., Phage-displayed antibody libraries of synthetic heavy chain complementarity determining regions, Abstract, Journal of Molecular Biology, Apr. 23, 2004, pp. 299-310, vol. 338, No. 2.

Office Action for U.S. Appl. No. 11/593,280 dated Dec. 11, 2009.

Notice of Allowance for U.S. Appl. No. 11/593,280 dated Apr. 6, 2010.

Office Action for U.S. Appl. No. 12/221,021 dated May 12, 2010.

Friedenson, Bernard et al., "Immunoglobulin G Antibodies from an Individual Rabbit in Which Several Heavy Chain Variants are Paired with One Light Chain Sequence." The Journal of Biological Chemistry. Oct. 25, 1973, pp. 7073-7079, vol. 248, No. 20.

Conrath et al., Camel Single-domain Antibodies as Modular Building Units in Bispecific and Bivalent Antibody Constructs, The Journal of Biological Chemistry, 2001, pp. 7346-7350, vol. 276, No. 10.

Nguyen et al., Heavy-chain only antibodies derived from dromedary are secreted and displayed by mouse B cells, Immunology, 2003, pp. 93-101, vol. 109.

Tanaka et al., De novo production of diverse intracellular antibody libraries, Nucleic Acids Research, 2003, e23, pp. 1-10, vol. 31, No. 5.

Lenz, et al.; Expression of heterobispecific antibodies by genes transfected into producer hybridoma cells; Gene; 87 Mar. 15, 1990, No. 2; pp. 213-218.

Morimoto et al., Abstract, High level expression of a human rabies virus-neutralizing monoclonal antibody by a rhabdovirus-based vector, J. Immunol. Methods, Jun. 2001, pp. 199-206, vol. 1, No. 252(1-2).

Arai et al., Abstract, Antibody responses induced by immunization with a Japanese rabies vaccine determined by neutralization test and enzyme-linked immunosorbent assay, Vaccine, Jun. 2002, pp. 2448-2453, vol. 7, No. 20(19-20).

Perrin et al., Abstract, In vitro rabies vaccine potency appraisal by ELISA: advant of the immunocapture method with a neutralizing anti-glycoprotein monoclonal antibody, Biologicals, Oct. 1990, pp. 321-330, vol. 18(4).

Roholt et al, Antibodies of Limited Heterogeneity: L. Chains of a Single Mobility, Immunochemistry, Pergamon Press, 1970, vol. 7, pp. 329-340.

Carmack et al, Influence of a Vκ8 L Chain Transgene on Endogenous Rearrangements and the Immune Response to the HA(SB) Determinant on Influenza Virus The Journal of Immunology, 1991, vol. 147, No. 6, pp. 2024-2033.

* cited by examiner

MIXTURE OF BINDING PROTEINS

CROSS-REFERENCE TO RELATED APPLICATIONS

This application is a continuation of PCT International Patent application No. PCT/NL2005/000036, filed on Jan. 19, 2005, designating the United States of America, and published, in English, as PCT International Publication No. WO 2005/068622 A2 on Jul. 28, 2005, which application claims priority to European Patent Application Serial No. 04075170.3 filed on Jan. 20, 2004, the contents of the entirety of each of which are incorporated by this reference.

STATEMENT ACCORDING TO 37 C.F.R. §1.52(e)(5)-SEQUENCE LISTING SUBMITTED ON COMPACT DISC

Pursuant to 37 C.F.R. §1.52(e)(1)(iii), a compact disc containing an electronic version of the Sequence Listing has been submitted concomitant with this amendment, the contents of which are hereby incorporated by reference. A second compact disc is submitted and is an identical copy of the first compact disc. The discs are labeled "copy 1" and "copy 2," respectively, and each disc contains one file entitled "2183-7926US SeqListing.txt" which is 4 KB and created on Nov. 3, 2006.

TECHNICAL FIELD

The invention relates to biotechnology and molecular biology, in particular, to medical molecular biology. Specific recognition plays an important role in modern medical biology. Receptor-ligand interactions, immune responses, infections, and enzymatic conversions are all based on specific recognition between molecules. Of particular interest are specific protein-protein interactions, which give a vast array of possibilities of interfering in all kinds of biological processes.

BACKGROUND

Throughout nature, biological processes are found that depend on more than one (simultaneous) protein-interaction. At the present time, it seems that interfering at more than one point in a biological process is going to be more effective than a single interference. This interference may be mediated by two different proteins with binding activity (e.g., antibodies), each binding to an epitope on a target or targets associated with the biological process and subsequently inhibiting the biological process. Particularly, in antibody therapy it is seen that one (monoclonal) antibody is often not effective enough for treating a particular disorder and/or disease. Therefore, the attention of many medical researchers is now focused on combination therapies. Well known examples of combinations of antibodies that are presently clinically pursued are for the treatment of non-Hodgkin's lymphoma, the combination of the already approved anti-CD20 antibody Rituxan with the anti-CD22 antibody Epratuzumab from AmGen, and for the treatment of Hepatitis B, a combination of two human antibodies being developed by XTL Pharmaceuticals (E. Galun et al., *Hepatology* (2002) 35:673-679). However, the combination of multiple (two or more) drugs (be it binding proteins, antibodies or other) has a number of technical, practical and regulatory drawbacks. In the past, binding proteins (such as antibodies) were typically not designed to function and be produced in combination with one another and development as combinations with optimal clinical efficacy and compatibility may be a problem. As an example, conditions for stabilizing the one may be detrimental to stability of the other(s). Furthermore, multiple sources of recombinant production lead to multiple sources of risks, such as viral contamination, prion contamination and the like.

Historically, the most investigated binding proteins are antibodies. Antibodies normally display binding sites composed of two separate polypeptide chains, assembled as tetrameric protein in the immunoglobulin IgG molecule. More recently, it has become possible to produce single polypeptide chain binding proteins, in which binding is mediated by a single protein domain. Such binding proteins can be based on the same or highly related protein scaffolds or sequence, yet display highly divergent binding specificities. Herein, "SPCBP" is defined as a single polypeptide chain binding protein, and "SPCBPs" as single polypeptide chain binding proteins. Frequently, they are made by first providing a certain level of diversity in a chosen monomeric protein scaffold or fold, which itself can have a natural origin or synthetic basis, and then using molecular selection or screening methods to identify amongst the protein variants those that show a desirable binding specificity. Alternatively, they are harvested from nature, which also has some sources of SPCBPs, such as the "heavy chain only" camelid and shark antibodies.

DISCLOSURE OF THE INVENTION

Described are methods for producing libraries of cells expressing at least two separate single binding proteins, in which the binding proteins have different target epitopes. Such libraries are made by integration of the nucleic acid sequences encoding the polypeptide chains into the genome of the host cell, and selecting for cells that have successfully integrated these nucleic acids. The selected cells are preferably subjected to a cloning step. This cloning step is preferably linked to a selection and/or screening step involving selection and/or screening of cells producing suitable binding proteins, examples of such selection steps are discussed elsewhere in this application. It is preferred that the nucleic acids encoding these polypeptide chains are related in their amino acid sequence outside of the binding region such that the mixture of binding proteins can be isolated by the same physico-chemical purification procedure. In this context, it is preferred that the polypeptide chains are at least 70% homologous. By producing multiple recombinant host cell lines that each express multiple binding proteins and in which each cell line expresses the proteins at a set ratio, many different mixtures of binding proteins can be readily made, and without having to express, purify and characterize each binding protein individually. By assaying such mixtures, for example, in a biological activity assay, the composition of the mixture with the most optimal biological activity can be determined, and the concurrent host cell line producing exactly this mixture identified.

Since it is preferred that the binding proteins included share a certain level of nucleic acid sequence homology and physicochemical nature, the mixture of binding proteins can be isolated by physico-chemical purification procedures that, with similar efficiency, will purify all components of the binding protein mixture. Such a method provides a means to produce mixtures of binding proteins for therapeutic applications without having to individually produce the components of the mixture, which has important technical, financial and time drawbacks. The present inventors have further opened up an avenue of improvements in screening the properties of combinations of binding proteins. These improvements and their advantages will become apparent from the following description.

Thus, one of the technical problems underlying the invention is to provide methods for producing and assaying mixtures of binding proteins without having to individually produce each of the components of the mixture. A solution to this technical problem is achieved by providing the embodiments characterized in the claims. Accordingly, the invention allows constructing collections of homologous binding proteins that are binding different target epitopes, that are expressed in the same host cell and in which the homology leads to a common method for the purification of all homologous binding proteins as a mix of proteins. The technical approach of the invention, i.e., to derive libraries of cells expressing mixtures of SPCBPs and screen such libraries for compositions with optimal bioactivity, is neither provided nor suggested by the prior art.

"Binding" is defined as interactions between molecules that can be distinguished from background interactions. Typically, specific interactions between molecules have higher binding affinity then background interactions between molecules. Binding proteins are proteins made up of a sequence of amino acid residues and bind an epitope on a target. Specific binding proteins are made up of amino acid residues (proteinaceous molecules).

By producing the two or more desired binding specificities in one system, there is only one source of the products and thereby less risk of contamination with viruses, prions and the like. There is also more likelihood that post-translational modifications imposed on the binding proteins as they are expressed inside the host cell will be similar if not indistinguishable from one another. Contrary, while producing binding proteins in different cells, even when these are identical cells, will the culturing conditions affect some of the post-translational modifications. It is preferred to carry out methods according to the invention inside an immortalized cell, typically a eukaryotic cell line, and preferably CHO, SP2/0, NS0 or PER.C6. For production of libraries and selection of optimal mixtures, other cells can be used such as bacteria, insect cells, yeasts and other eukaryotes that are typically suitable for the production of small globular proteins (*E. coli, Pichia pastoris, S. cerevisiae*, etc.) are preferred.

The production of the separate binding proteins takes place in the same host cell. A particularly useful way of producing binding proteins is through the expression of nucleic acids encoding these binding proteins. It is preferred that all binding proteins in one cell are produced by such expression. For most purposes, the nature of the nucleic acid is not critical, it is RNA, preferably DNA, episomal or integrated, or part of a viral vector or a plasmid. It is preferred that at least two binding proteins are encoded by separate nucleic acid sequences.

In another embodiment, at least two nucleic acid sequences encoding at least two single polypeptide chains are part of the same nucleic acid. In this way, the copy number of at least two nucleic acid sequences, in relation to each other, can be made essentially constant.

In yet another embodiment, at least two nucleic acid sequences encoding at least two single polypeptide chains are part of two different nucleic acids. In this way, the copy number of at least two nucleic acid sequences can be varied in relation to each other, in a controllable fashion. For the final production system of the combination of binding proteins having different binding specificities, it is preferred that the nucleic acid or acids encoding the binding proteins are stably integrated into the host genome, preferably, the nucleic acid comprises means for site-directed integration of the nucleic acid sequence encoding the binding proteins, preferably, the means are means for homologous recombination. Production of binding proteins through expression of nucleic acids encoding them gives the possibility to manipulate the encoding sequences, thereby enabling the designing of new binding specificities, exchanging useful sequences from one encoding sequence to another and the like.

Particularly for making therapeutic preparations of multiple binding proteins, fusions of one or more of the binding proteins can be made to a sequence that does not influence the binding specificity of the binding protein itself, but provides an effector function or detection handle. Examples of this are beta-galactosidase, carboxypeptidase G2 (or other enzymes involved in antibody-directed enzyme-prodrug therapy), human RNAse, Onconase (or other RNA degrading enzymes), bacterial or plant toxins (ricin A, *Pseudomonas* exotoxin), cytokines or growth factors (TNF, IL-1, IL-12, GM-CSF). The methods as disclosed herein provide for adaptation of the nucleic acids encoding binding proteins to the desired end result.

Binding proteins as used herein are intended to refer to all variations of proteins that retain or have specific binding activity. Thus, the invention also provides a method wherein the binding proteins are derived from engineered protein scaffolds such as anticalins, fluorobodies, affibodies etc., or are derived from heavy chains and/or light chains of immunoglobulins, engineered versions of variable regions of immunoglobulins with elements of heavy and/or light chains of immunoglobulins and/or a method wherein the proteinaceous molecules are fragments and/or derivatives of antibodies.

A method of the invention is preferably used for the production of libraries of cells expressing multiple (i.e., two or more) binding proteins in one system and compositions comprising multiple binding proteins produced by these methods. For biopharmaceutical production of such protein mixtures, it will be necessary to obtain an expression system that is compatible with the scale of the industrial processes that are employed. Typically, recombinant host cells are made in which the expression system encoding the transgenes (or the nucleic acids encoding proteins of interest) are retained by the host cells in a stable and active form during the growth phases of scale-up and production. This is typically achieved by integration of the transgenes into the genome of the host cell. By selecting for successful integration events (for example, via genetically encoded selection markers present on the expression vectors used for the transfection), cells are isolated that have integrated the nucleic acids encoding the single polypeptide chains and express these at variable levels. Variation in expression levels is due to many factors including positional cloning effects and copy number of the transgene. This creates a library of combinations that is screened in bioassays to identify the most optimal mixture. The methods provide a means to identify a host cell that expresses the different binding proteins at the most optimal ratio.

Another element of the invention useful for control of the production of diverse libraries is placing expression of different binding protein-encoding genes under control of different regulatory elements, such as promoters, (trans) activators, enhancers, terminators, anti-repressors, stabilizing anti-repression (STAR) elements, repressors, locus control regions, matrix-attachment regions, Internal Ribosome Entry Site (IRES) and the like. These regulatory elements are constitutive, inducible or repressible and depending on their function, provided in cis or in trans. Thus, the production of binding proteins can be regulated and variegated, thus providing a means to achieve variable ratios of binding proteins in each cell, i.e., wherein different regulating elements give rise to different expression levels of different binding proteins.

Different combinations of binding proteins can be made by separation in time of expression of various binding proteins, and ratios between different binding proteins are manipulated by regulating expression levels. Variations are described herein. Preferably, nucleic acid sequences comprise a coding sequence for localizing and anchoring the resulting binding protein in a cell membrane. The invention also provides an expression system for carrying out a method according to the invention comprising nucleic acids encoding binding proteins together with all elements required for gene expression. Preferably, such an expression system comprises at least one recombinant cell, such as a bacterium, a yeast cell, a fungal cell, an insect cell, a plant cell or another eukaryotic cell, preferably a mammalian cell, more preferably a human cell. In a preferred embodiment, the cell encodes two to ten different, separate, single amino acid chain binding proteins. Such a system can be provided with all necessary and useful control elements as disclosed hereinbefore and as well known in the art. Selection elements and suicide elements can also be introduced into such a system as desired.

A collection of expression systems according to the invention comprising a variety of combinations of different specificities is also provided, typically as a library for use in selecting desired combinations of binding proteins. A desired combination may be a preferred combination of binding specificities, a particular ratio of expressing the proteinaceous molecules or preferably a combination of both properties. Such selection methods are also part of the invention. Thus, the invention in one embodiment also provides a method for selecting combinations of proteinaceous molecules having specific affinity for at least two target epitopes, comprising contacting a collection according to the invention with the two target epitopes and selecting combinations showing specific affinity.

Further provided is a method for producing a cell expressing at least two separate single polypeptide chain binding proteins having different target epitopes, comprising contacting a library of cells of the invention with different target epitopes and screening for and selecting a cell expressing binding proteins recognizing the target epitopes. Preferably, the method comprises transferring the nucleic acids encoding at least two separate single chain binding polypeptides into a production cell. Preferably, screening and/or selecting is achieved by performing a bioassay as a method of screening and/or selecting. Apart from binding, a bioassay has the advantage that ratios of expressing at least two separate single chain polypeptide chain binding proteins having different target epitopes are also selected for efficacy. This further speeds up the process of selecting and screening. Furthermore, combinations of proteinaceous molecules that are only effective in certain ratios are not missed using a bioassay.

In another embodiment, the invention provides a method for producing a cell expressing at least two separate single polypeptide chain binding proteins having different target epitopes and capable of antagonizing a function of a molecule comprising at least one of the target epitopes, comprising contacting a library of cells of the invention with the different target epitopes and screening for and selecting a cell expressing binding proteins recognizing the target epitopes and performing a bioassay measuring antagonistic activity.

In yet another embodiment, the invention provides a method for producing a cell expressing at least two separate single polypeptide chain binding proteins having different target epitopes and capable of activating a function of a molecule comprising at least one of the target epitopes, comprising contacting a library of cells of the invention with the different target epitopes and screening for and selecting a cell expressing binding proteins recognizing the target epitopes and performing a bioassay measuring activating activity.

In yet another embodiment, the invention provides a method for producing a composition comprising at least two separate single polypeptide chain binding proteins having different target epitopes, comprising expressing at least two nucleic acid sequences encoding the binding proteins in one cell, wherein the nucleic acid sequences are at least 70% homologous, such that the resulting binding proteins can be purified by the same purification method. Preferably, at least two binding proteins are encoded by separate nucleic acid sequences.

In a particularly preferred embodiment, at least two nucleic acid sequences encoding at least two binding proteins are under control of different regulatory elements.

In another embodiment, the different regulatory elements are chosen from a promoter, preferably inducible, an enhancer, a terminator, a stabilizing anti-repressor element, an internal ribosomal entry site, a matrix-attachment region, a ubiquitous chromatin-opening element, a boundary element, a locus control region, or a scaffold-attachment region.

In a preferred embodiment, different regulatory elements give rise to different expression levels of different binding proteins. In this embodiment, it is preferred that at least two cells are produced and that a selection or screening using a bioassay as mentioned above is used to select and/or screen for a cell expressing a favorable ratio of the binding protein.

It is preferred that each cell encodes two to ten different, separate single amino acid chain binding proteins. At least two nucleic acid sequences encoding at least two single polypeptide chains are preferably part of the same nucleic acid, in eukaryotic cells or part of two different nucleic acid (eukaryotic and prokaryotic cells).

Such methods are particularly useful when two target epitopes are associated with one disease or disorder. It is preferred to combine such a method with subjecting a selected combination of proteinaceous molecules to a biological assay indicative of an effect of the combination on the disease and/or disorder.

Compositions obtainable by a method of the invention are also part of the invention. Compositions comprising at least two different binding proteins having different binding specificities are preferred. A combination composition that targets both TNF-α as well as IL-1β is an exemplary combination of the invention. In such typical therapeutic uses it is important that the combination preparations do not lead to severe immune responses in the subject to be treated. Preferably, the scaffold that was used to build the binding proteins is of human origin, or the scaffold shows a high level of homology with its human counterpart (e.g., camelid or VHH antibodies). Potentially antigenic parts of the binding molecules are alternatively modified (e.g., by removing putative T-cell epitopes), omitted or masked by molecules such as PEG. Thus, the invention also provides in one embodiment a composition according to the invention, which is a pharmaceutical composition.

Although binding proteins have found use in other areas and binding protein combinations can be used in other areas, the pharmaceutical use of the invented combinations is preferred, both diagnostic and therapeutic, with a preference for the latter. However, in industrial applications, the combinations of the invention are superior to existing separation techniques because of ease of production, consistency of production and the availability of many combinations of specificities capable of separating almost anything from any mixture. In testing, be it in pharmaceutical diagnostics or in any other field (e.g., environmental or agricultural), the combinations of the invention can be used advantageously as well. Both partners of a sandwich assay can be made in one cell. Agglutination mixtures can be made in one cell. Again, ease and consistency of production, as well as the diversity of specificities, is an asset of the combinations of the invention. These advantages, of course, also apply in selecting and producing combinations of specificities for therapeutic and/or prophylactic use, with additional advantages in ease of selection, efficacy of selected combinations and the mentioned safety aspects.

Further provided is a method for producing a composition comprising at least two separate single polypeptide chain binding proteins having different target epitopes, comprising culturing a cell of this invention, allowing the cell to express at least two separate single polypeptide chain binding proteins having different target epitopes and harvesting at least two separate single polypeptide chain binding proteins having different target epitopes.

A simple combination according to the invention starts with two specificities present in the combination. Thus, the invention in one embodiment comprises compositions comprising at least two monospecific binding proteins for use as a pharmaceutical.

These multispecific mixtures resemble polyclonal antibody mixtures in their efficacy for recognizing antigens, but without the drawbacks of many irrelevant specificities in the mixture. The mixtures of binding proteins resemble monoclonal antibodies in their defined constitution, ease of production and high specificities, but without the concomitant loss of efficacy. The mixtures thus contain two, three, or more different binding specificities, and exist in various formats. In the simplest form, a mixture of binding proteins according to the invention contains two or more related binding proteins with different binding specificities.

As disclosed herein, the methods and means of the invention in one embodiment are the production of combinations of specificities. Before production of combinations, suitable combinations are to be designed and/or selected. These methods for designing and selection are also part of the invention.

The invention further provides a cell obtainable by a method of the invention and a non-human transgenic animal comprising a cell obtainable by a method of the invention.

Preferred nucleic acids (also part of the invention) for use in producing combinations of specificities are binding proteins created by combinatorial biotechnology. These include binding proteins based on the immunoglobulin-fold (domain antibodies, or dAbs, camelid antibodies (VHH) or other natural folds (anticalins, affibodies, fluorobodies), and their engineered variants (fusions to other effectors or tags). Domain antibodies can, for example, be derived from either immunoglobulin heavy chain variable regions or immunoglobulin light chain variable regions, but can also be engineered hybrids of heavy and light chain variable regions (with, e.g., swapped CDR regions or FR regions). Dabs can, e.g., be obtained from hybridomas, by cloning from immune or non-immune donors or can be synthetically constructed variable regions. Of course, parts and/or derivatives according to this invention are such parts and/or derivatives that as single polypeptide chains have specific binding properties and are comparable to these cited examples.

In one aspect, the invention provides a library of cells, wherein essentially each cell encodes at least two single polypeptide chain binding proteins having different target epitopes, obtainable by a method according to the invention. The library preferably comprises at least two cells encoding identical single polypeptide chain binding proteins and expressing them at a different ratio, preferably, though not necessarily, the cell library comprises eukaryotic cells.

BRIEF DESCRIPTION OF THE FIGURES

FIG. 1: General outline of the expression cassette and expression vectors for eukaryotic cells. The legend of the vector elements is depicted on the right.

DETAILED DESCRIPTION OF THE INVENTION

Figure 1A:
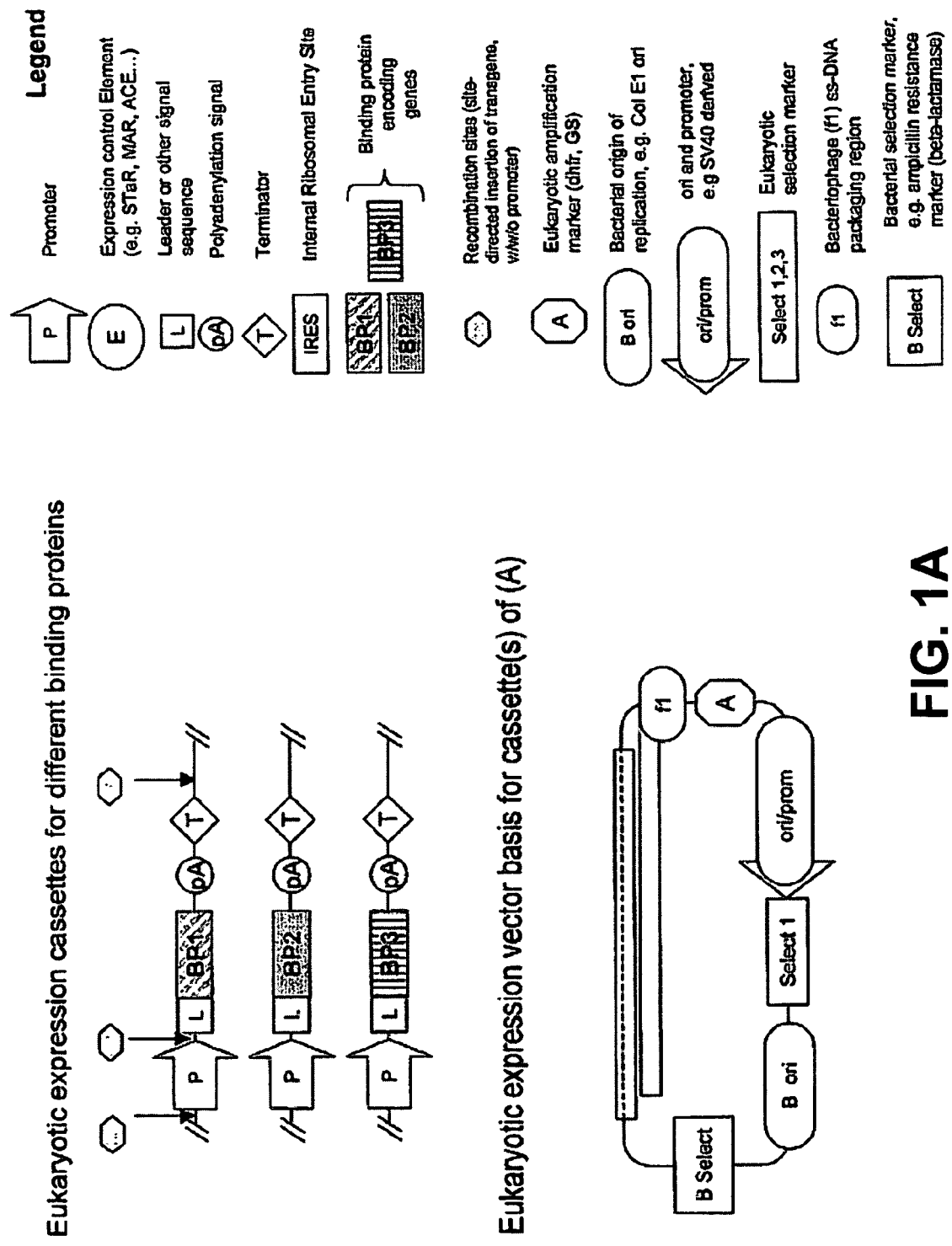
In FIG. 1A on the left-hand side top panel are depicted three eukaryotic expression cassettes for three different binding proteins, BP1-3. These are schemes of the elements found in an expression cassette for a single polypeptide chain binding protein gene or nucleic acid and typically comprises a promoter, a Leader sequence (optional), an open reading frame encoding the protein of interest, a polyadenylation region (for eukaryotic expression) and a terminator, all in operable configuration. In addition, sites used for site-directed and in some cases homologous recombination, are shown (are also optional; indicated on top of the first expression cassette). On its bottom panel is depicted an exemplary vector backbone used for insertion of the top panel cassette(s). This scheme displays the typical elements of a eukaryotic expression vector, comprising a bacterial origin of replication (such as Col E1), a bacterial selection marker (B Select, such as the ampicillin resistance gene), a eukaryotic selection marker (Select, such as gpt, neo, zeo etc., see text; useful when stable integration into the host cell's genome is envisaged), and additional optional elements such as a bacteriophage packaging region (for ss-DNA production, such as f1), and an optional amplification marker (such as DHFR). Optional but not shown in the vector backbone neither expression cassettes are other expression controlling elements (such as BEs, STAR, LCRs, MARS and the like, see below) and IRES; these are included in later figures.

1. Background
   1.1 Antibodies

In the fight against infection, the immune system creates a cellular and humoral response that can specifically combat the infectious agent. The humoral immune response is based on immunoglobulins, or antibodies, which contact antigens and mediate certain effector functions to clear the infection (I. M. Roit et al. (1985) and all references herein). In the immune system, antibodies are generated by B-lymphocytes. Antibodies consist of heavy and light chains that are assembled via inter-domain pairing and interchain disulphide bonds to form multivalent molecules. Various isotypes of natural antibodies exist, including IgG (within humans, four subclasses, IgG1, IgG2, IgG3, IgG4), IgM, IgD, IgA and IgE. An IgG molecule contains two heavy (H) and two light (L) chains, both with variable (V) and constant (C) regions. A typical IgG antibody comprises two heavy (H) chain variable regions (abbreviated herein as VH), and two light (L) chain variable regions (abbreviated herein as VL). The VH and VL regions can be further subdivided into regions of hypervariability, termed "complementarity determining regions" (CDR), interspersed with regions that are more conserved, termed "framework regions" (FR). The extent of the framework region and CDRs has been precisely defined (see, E. A. Rabat et al. (1991) *Sequences of Proteins of Immunological Interest*, Fifth Edition, U.S. Department of Health and Human Services, NIH Publication No. 91-3242; and C. Chothia et al. (1987) *J. Mol. Biol.* 196:901-917, which are incorporated herein by reference).

In the generation of the primary immune response, the pairing of heavy and light variable region sequences of antibodies is a random process. The variable region genes are first assembled by recombining a set of randomly picked V, (D) and J genetic elements represented in the genome as a diverse gene pool. The recombined heavy and light variable regions are then spliced towards their respective constant region genes and the chains expressed, assembled and secreted as immunoglobulin. In this combinatorial library, in principle, every heavy chain can pair with every light chain to create a vast repertoire of different antigen specificities, with diversity derived from the rearrangement process (which also introduces further diversity at some of the segment junctions) and from the combinatorial assembly of the heavy and light chain variable regions. In principle, B-cells produce only one antibody specificity, encoded by one antibody heavy and one antibody light chain sequence. The immune system selects via an efficient antigen-selection process those antibodies that can bind to a given antigen, in particular, when the antigen is foreign and part of a pathogen.

In natural immunoglobulins, the light chain which consists of two domains, is paired to the heavy chain, which consists of at least four domains and a hinge region: non-covalent interactions occur between VH and VL, and between CH1 and CL; between the latter, a disulphide bridge provides a covalent linkage between heavy and light chains. Furthermore, the heavy chains are found paired to one another, i.e., in the IgG format, and sometimes further associate with additional elements such as J-chains (i.e., in the IgM format). A strong non-covalent interaction occurs between the CL and CH1 domains, a frequently weaker interaction is present between VL and VH. The heavy chains are paired via interactions in the hinge region (often covalently associated via one or more disulphide bridges) and between the CH2 and CH3 domains.

Within one B-cell, typically only one light and one heavy chain is expressed, but in the few instances that other light or heavy chains are expressed (such as in two fused B-cells), mispairing between the chains will occur, and antigen binding is lost in this fraction of the antibody preparation. For example, in the past, the expression of multiple antibody variable domains, as in quadromas or cells transfected with multiple heavy and/or light chain genes, typically yields a large fraction of pairings of variable regions that are not functional.

1.2 Therapeutic MoAbs

State of the art antibody engineering allows the generation of "tailor-made" antibodies in terms of specificity, affinity and constant region-mediated effector mechanisms. The strong sales growth of the expanding number of approved MoAbs is testament to their success. In the year 2000, the combined sales of human or humanized antibodies exceeded $2 billion and are expected to exceed $6 billion by 2005. With 13 MoAbs registered for the treatment of a variety of diseases including cancer, autoimmune disease, transplant rejection and antiviral prophylaxis, an estimated 200 antibody products in various phases of clinical testing and approximately 470 additional antibodies in preclinical development, MoAbs were in 2002 also the most important category of new drugs. For example, a number of monospecific antibodies have been approved as human therapeutics. These include Orthoclone OKT3, which targets CD3 antigen; ReoPro, which targets GP IIb/IIIa; Rituxan, which targets CD20; Zenapax and Simulect, which target IL-2 receptors; Herceptin, which targets the HER2-receptor; Remicade, which targets tumor necrosis factor; Synagis, which targets the F protein of respiratory syncytial virus; Mylotarg, which targets CD33; and Campath, which targets CD52 (see, e.g., Carter (2001) *Nature Reviews* 1:118-129; Ezzell (2001) *Scientific American* October 2001, pages 36-41; Garber (2001) *Nat. Biotechnol.* 19:184-185).

The notion that current generations of recombinant human MoAbs require further optimization to achieve improved clinical effects has spurred the development of antibody conjugates: antibodies linked to drugs, toxins or radionuclides that exploit the specificity of the antibody to deliver a highly toxic compound to, for example, tumor cells. Despite their improved potency, conjugated antibodies are more toxic then "naked" antibodies and require more complex manufacturing processes, restricting their applicability and increasing their costs. In addition, conjugated antibodies do not address the lack of efficacy of MoAbs when killing a target cell is not the desired mechanism of action.

An important reason for lack of efficacy of naked MoAbs is that they bind to only a single epitope on a target (virus, cancer cell, toxin etc.). In contrast, in natural antibody responses, a multitude of antibodies (polyclonal antibodies) that bind to many epitopes on a target are generated, resulting in a more efficient elimination or neutralization of targets. Although polyclonal antibodies may be considered more efficacious drugs then MoAbs, their widespread use is hampered by many drawbacks.

In the therapeutic antibody field, there is a need for novel approaches that combine the existing superior technology of "naked" human MoAbs with the higher levels of clinical efficacy associated with polyclonal antibodies. To capture the efficacy inherent in polyclonal antibodies, some efforts have gone into the development of cocktails of MoAbs targeting the same entity. At the research level, additive or synergistic effects on therapeutic efficacy have been demonstrated for combinations of MoAbs that were separately produced and subsequently mixed at the protein level or administered simultaneously to animal models.

1.3 Polyclonal Antibodies

Polyclonal antibodies isolated from animal sera have been employed in the clinic for more than a century to treat bacterial and viral infections and are still applied for many different indications. Polyclonal antibodies consist of an ill-defined mixture of antibodies purified from the serum of an animal or human. The polyclonal serum is enriched for specific antibodies by prior immunization or infection. Products of human origin are preferred over those of animal origin because of the high incidence of adverse reactions to animal sera and the longer lasting protection conferred by human antibodies.

Polyclonal antibodies have the advantage of consisting of a multitude of MoAbs that target different epitopes, thereby often conferring more potent biological activity. While proven effective, their wider-spread use has been limited for a variety of reasons, including the immunogenicity of animal-derived proteins in human patients. Preparations of polyclonal antibodies suffer from the following drawbacks: (1) Polyclonal antibodies are costly and labor-intensive to produce. (2) The amount of specific antibodies in a polyclonal antibody preparation usually represents only a minute fraction (<1%) of the total antibody protein, resulting in injection of large amounts of non-relevant protein in patients. (3) Polyclonal preparations generated from immune donors or immunized animals are difficult to control quality. (4) Polyclonal preparations generated from the pooled sera of immune donors or immunized animals display lot-to-lot variations. (5) The specificity and affinity of the specific antibodies in the preparation are undefined. (6) The amount of available antiserum may be limited for some applications. (7) Because polyclonal antibodies are derived from pools of sera, the possibility of transmission of infectious agents (viruses, prions) exists. Yet, polyclonal antibodies have the advantage of consisting of a multitude of MoAbs that target different epitopes, thereby often conferring more potent biological activity. While proven effective, their wider-spread use has been limited for a variety of reasons, including the immunogenicity of animal-derived proteins in human patients. In some cases is has become clear that a polyclonal antibody of animal origin may be more effective than a MoAb: a recently approved polyclonal antibody of rabbit origin, Thymoglobulin®, proved more efficacious then a humanized MoAb, Simulect™, in the treatment of transplant rejection.

1.4 Protein Mixtures

Mixtures of three to five MoAbs prepared by combining antibodies at the protein level have superior therapeutic effects compared to MoAbs. However, large-scale manufacturing of multiple individual MoAbs that are mixed to form a single product poses insurmountable problems for pharmaceutical development related to regulatory issues, the cost of parallel development of multiple MoAbs, and the design of current manufacturing facilities for biopharmaceuticals. Similarly, therapeutic polyclonal antibodies, although often more potent than MoAbs, display major isolation, safety and development issues. Methods to create mixtures of binding proteins are, therefore, addressing a crucial need in therapy.

Thus far, mixtures of functional monoclonal antibodies have been made by expressing and purifying the proteins separately and then mixing them at the protein level. Generally, there are several other problems underlying the production of such protein mixtures. A first problem with relying on mixtures of binding proteins that have been first separately expressed, produced and purified, and then mixed, is the differential susceptibility of each preparation to external factors that will modify the binding protein. For example, often epitope and detection/purification tags (such as the myc, FLAG or ploy-HIS tags or fusions to protein A, protein Z domain, maltose binding protein and GST) are provided for detection and purification of the expressed binding protein. As these are usually located at the N or C terminal ends of the binding protein, they tend to be prone to proteolytic cleavage. If the tag of one but not the other binding protein has been extensively degraded, for example, due to extensive bacterial cell lysis during production, the two proteins in the mix will display more differences than just their binding specificity. Other examples are sequence-independent or dependent protein modifications such as glycosylation, oxidation, etc. The distribution of glycosylation of proteins by eukaryotic cells is susceptible to other factors that are present in the growth media of the cells and by culturing conditions. Even when binding proteins such as antibodies are produced in the same host cells, this will not be a guarantee that the glycosylation pattern and contents will be identical. To this end, it would be desirable to have a system which could eliminate undesirable differences between binding proteins that have to be used as mixtures.

Problems exist with testing large numbers of protein mixtures that are assembled in vitro by mixing samples of the individual components. Each component is separately prepared, purified, and its quantity accurately determined. Often, protein purification is a lengthy process and not easy to upscale for hundreds of samples. The determination of the active fraction of a protein preparation is time consuming and is not always possible and with time, the activity may be altered (which is often also a function of how well the protein component was purified). To this end, it would be desirable to have a method that provides mixtures of binding proteins that are expressed at different ratios and expressed in such a manner that the purification and concentration determination can be done with one and the same sample.

A third problem with relying on screening of mixtures of purified proteins is to find the optimal combination for biological activity and then producing a host cell that expressed the binding protein components of that optimal ratio. First, many cell lines are screened to find one that expresses the ratio of the effective combination, a problem that increases with increasing the number of different binding proteins in the mix. Second, in some cases, the co-expression of one binding protein simultaneously with other binding proteins can lead to unexpected negative effects on protein aggregation, on cell viability and on production levels.

2. Making Mixtures of Binding Proteins 2.1 Libraries of Binding Proteins Expressed at Variable Quantities Described are methods to produce libraries of cells expressing mixtures of SPCBPs. The invention provides a method that addresses at least some of these cited problems that occur when mixing proteins in vitro. The method minimizes differences between binding proteins that are used as a mixture, due to the simultaneous expression in the same host cell. It simplifies manipulation of the proteins and obviates the need to purify the proteins separately. If the binding proteins are modified post-translationally during these processes, sequence-independent modifications and alterations may appear but are likely to appear in all binding proteins at equal or similar frequency. For example, N-linked glycosylation of two binding proteins is more likely to be similar, if not indistinguishable, when these proteins are expressed in the same host cell compared to expression in two separate host cells. This will make the protein characterization and interpretation of the biological activity more straightforward. Finally, the direct screening of mixtures expressed by one host cell would remove those cases in which one binding protein is incompatible with the expression of others. In addition, it has a number of additional advantages that are detailed below.

The expression of multiple proteins inside the same host cell has been described, e.g., for producing proteins that consist of functional multimers, which is, however, a very different approach from what is presented here. Multimeric proteins consist of two or more possibly different polypeptide chains in their biologically and/or biotechnologically active form. Examples include antibodies (Wright and Morrison 1997), bone morphogenetic proteins (Groeneveld and Burger 2000), nuclear hormone receptors (Aranda and Pascual 2001), heterodimeric cell surface receptors (e.g., T-cell receptors (Chan and Mak 1989)), integrins (Hynes 1999), and the glycoprotein hormone family (chorionic gonadotrophin, pituitary luteinizing hormone, follicle-stimulating hormone, and thyroid-stimulating hormone (Thotakura and Blithe 1995)). In all of these cases, the different polypeptides that were expressed assembled in the cell to one functional protein.

The invention differs in that multiple binding proteins are expressed and that these are non-associated and thus retrievable as separate proteins. Binding proteins that carry two chains forming one binding site are thus excluded from this invention. There is also a major difference in the approach and in the end result. The production of a multimeric protein in a heterologous system is technically difficult due to difficulties in attaining production of the monomeric polypeptides in stoichiometrically balanced proportions (Kaufman 2000). Imbalanced expression of the monomers is wasteful of the costly resources used in cell cultivation and can have deleterious effects on the cell (including sequestration of cellular factors required for secretion of the recombinant proteins and induction of stress responses that result in reduced rates of growth and protein translation, or even in apoptosis (programmed cell death)). Such deleterious effects lead to losses in productivity and yield and to higher overhead costs. Many described expression systems for such multimeric proteins have, therefore, focused on obtaining a balanced and proportional expression of two or more polypeptide monomers that are constituents of a multimeric protein. In this invention, libraries of cells are created that each express the different binding proteins purposely at a different ratio, such that a library of cells that express a subset of at least two binding proteins are produced and in which the ratio between the expression levels of the two binding proteins is highly variable. Eventually, the ratio that mediates the suitable bioactivity is determined and the cell line producing this ratio is used to produce the mixture of two binding proteins at this ratio.

2.2. Examples of SPCBPs and Methods to Identify These

The development of soluble binding proteins that recognize given target molecules is of importance in the life sciences and biotechnology. For the past century, this field was dominated by antibodies, which were traditionally generated via immunization of animals but also became available by means of protein engineering methods. The binding proteins used in this invention are based on a single polypeptide. They can be generated from certain animals (see below) or as artificial binding proteins in vitro, by applying techniques of combinatorial biotechnology to protein scaffolds or folds. The applicability of a scaffold or fold lies in the ability to introduce permissive diversity, without destroying the tertiary structure of the protein fold, and the ability to recover binding molecules from a diverse repertoire. Usually, existing scaffolds are recruited to randomize some exposed amino acid residues after analysis of the crystal structure. The recovery of binding variants of this scaffold can then be achieved by phage display and affinity selection on the ligand of choice. The properties of a scaffold are largely determined by the nature of the application and the properties of the scaffold. Many scaffolds described to date are small, globular proteins and are often comprising a single domain (thus, easier to produce, purify and engineer into multivalent or multispecific reagents).

In many cases, the scaffolds fulfill some or all of the following list of criteria, making them as binding proteins attractive alternatives to antibodies: (1) The scaffold should be expressed as a soluble protein in library-compatible hosts (*E. coli* and other bacteria, yeast cells, Baculovirus-infected cells, eukaryotic cells), and which are amenable to large-scale screening or display and selection technology (such as phage, ribosome, mRNA, cell display); (2) the tertiary structure of the scaffold should not be perturbed by the introduction of diversity; (3) the scaffold should also be stable; (4) the scaffold should have permissive loops, patches and/or surfaces for introducing diversity at a number of chosen sites, wherein the nature of the required binding surface depends on the application; (5) it should have a large accessible binding surface that has the potential to be further diversified and reselected, e.g., for affinity maturation purposes; (6) the scaffold should be engineerable to make monospecific/bispecific/trispecific or, in general, multispecific molecules; (7) it should allow fusion at the N- and/or C-terminus; (8) for therapeutic use in humans, it should be preferably non-immunogenic and human, and (9) it should be resistant to proteolysis.

A number of non-antibody and non-immunoglobulin fold-based scaffolds have been used to build artificial binding proteins. Perhaps the one in the most advanced state of development is the Z domain (K. Nord et al. (1995) *Protein Eng.* 8:601-608). Others include tendamistat (S. J. McConnell et al. (1995) *J. Mol. Biol.* 250:460-470), cytochrome b562 (J. Ku et al. (1995) *Proc. Natl. Acad. Sci. U.S.A.* 92:6552-6556), trypsin inhibitor (P. Rottgen et al. (1995) *Gene* 164:243-250), synthetic coiled coil (M. E. Houston, Jr. et al. (1996) *J. Mol. Biol.* 262:270-282), conotoxins, thioredoxin, knottins (G. P. Smith et al. (1998) *J. Mol. Biol.* 277:317-332), green fluorescent protein (M. R. Abedi et al. (1998) *Nucleic Acids Res.* 26:623-630), fibronectin (A. Koide et al. (1998) *J. Mol. Biol.* 284:1141-1151), and ankryn repeat proteins (H. K. Binz et al. (2003) *J. Mol. Biol.* 332:489-503). More examples of small scaffolding domains include: Kunitz domains (58 amino acids, three disulfide bonds), *Cucurbida maxima* trypsin inhibitor domains (31 amino acids, three disulfide bonds), domains related to guanylin (14 amino acids, two disulfide bonds), domains related to heat-stable enterotoxin IA from gram-negative bacteria (18 amino acids, three disulfide bonds), EGF domains (50 amino acids, three disulfide bonds), kringle domains (60 amino acids, three disulfide bonds), fungal carbohydrate-binding domains (35 amino acids, two disulfide bonds), endothelin domains (18 amino acids, two disulfide bonds), Streptococcal G IgG-binding domain (35 amino acids, no disulfide bonds) and small intracellular signaling domains such as SH2, SH3, and EVH domains. Generally, any modular domain, intracellular or extracellular, can be used. Thus, binding proteins can be derived based on many different structural folds, including β-sheet proteins, α-helical bundle proteins, combinations of these two, the immunoglobulin fold, and the eight-stranded beta-barrel. In one embodiment, the scaffolding domain is a small, stable protein domain, e.g., a protein of less than 200, 150, or 120 amino acids. The domain can include one or more disulfide bonds or may chelate a metal, e.g., zinc. Another example of a small scaffolding domain is a so-called "cysteine loop" formed by a pair of cysteines separated by amino acids, e.g., between 3 and 25 amino acids, or between 4 and 10 amino acids. The intervening amino acids can be any amino acid other than cysteine, in which case, under oxidizing conditions, the pair of cysteine disulfides bond and constrain the topology of the intervening amino acids.

Besides the use scaffolds based on natural folds, protein scaffolds suitable for making SPCBPs can also be identified de novo, by general computational strategies that iterates between sequence design and structure prediction. For example a 93-residue alpha/beta protein called Top7 was designed that was found experimentally to be folded and extremely stable; its x-ray crystal structure was similar to the design model (Kuhlman et al. 2003, *Science* 302:5649 and references therein). Further, native-like proteins suitable as a scaffold for SPCBP generation can be generated by combinatorial segment assembly from nonhomologous proteins (Riechmann and Winter 2000, *Proc. Natl. Acad. Sci. U.S.A.* 2000, 97:10068-73), a technology able to create novel domains and architectures in vitro, and SPCBPs with unique characteristics.

2.2.1. Single Domain Antibodies

The first scaffold to consider is the one used in the natural binding proteins, antibodies. The two domains of the antibody, forming the Fv fragment, are typically the smallest unit of an antibody that retains binding activity without significant loss in antigen affinity and specificity. But one domain by itself can also retain antigen-binding activity and exist as a single binding protein based on the immunoglobulin fold. Single-domain antibody fragments based on a single VH domain have been described (E. S. Ward et al. (1989) *Nature* 341:544-546), and have also been shown as naturally occurring molecules in camelidae (C. Hamers-Casterman et al. (1993) *Nature* 363:446-448). Also, single VH domains have been selected from diverse phage displayed libraries of engineered human (J. Davies et al. (1995) *Biotechnology* (N.Y.) 13:475-479) or mouse VH domains (Y. Reiter et al. (1999) *J. Mol. Biol.* 290:685-698). More recently, single human VH and VL domains have been engineered to bind protein antigens (T. van den Beucken et al. (2001) *J. Mol. Biol.* 310:591-601; L. J. Holt et al. (2003) *Trends Biotechnol.* 21:484-490).

2.2.2. Anticalins

One example of an alternative type of ligand-binding proteins are the anticalins, constructed on the basis of lipocalins as a scaffold. The central element of this protein architecture is a beta-barrel structure of eight antiparallel strands, which supports four loops at its open end. These loops form the natural binding site of the lipocalins and have been reshaped in vitro by extensive amino acid replacement, thus creating novel binding specificities (A. Skerra (2001) *J. Biotechnol.* 74:257-275). For example, the bilin-binding protein (BBP), a lipocalin of *Pieris brassicae*, was employed as a model system for the preparation of a random library with 16 selectively mutagenized residues. Using bacterial phagemid display and colony screening techniques, several lipocalin variants were selected from this library, exhibiting binding activity for compounds like fluorescein or digoxigenin. Anticalins are described to possess high affinity and specificity for their prescribed ligands, as well as fast binding kinetics, such that their functional properties are similar to those of antibodies. However, anticalins exhibit several advantages, including a smaller size, composition of a single polypeptide chain, and a simple set of four hypervariable loops that can be easily manipulated at the genetic level.

2.2.3. Affibodies

Protein engineering has also been used to generate tailor-made product-specific binding proteins that are used as affinity ligands in the recovery process of the product (P. Jonasson et al. (2002) *Biotechnol. Appl. Biochem.* 35:91-105). Particularly useful for this process are engineered binding proteins such as affibodies, proteins based on the three-helix scaffold of the Z domain derived from staphylococcal protein A. Affibody libraries are created by combinatorial variegation of residues within the three-helix bundle Z domain derived from staphylococcal protein A, and affibodies binding to the target of interest are selected using phage display or similar technologies. Affibodies to a wide range of other proteins have been identified and used for affinity chromatography of target proteins such as human IgA, factor VIII, Klenow DNA polymerase and the viral protease 3C (T. Graslund et al. (2002) *J. Biotechnol.* 96:93-102; K. Nord et al. (2001) *Eur. J. Biochem.* 268:4269-4277).

2.2.4. Isolating Antigen-Reactive SPCBPs

SPCBPs can, for example, be isolated using display-based antibody library technology, wherein antigen binding proteins are selected by exposing a library of proteins displayed on the surface of phage, yeast or other host cell, to the antigen of interest, and isolating those variants that bind to the antigen preparation. A display library is a collection of entities; each entity includes an accessible polypeptide component and a recoverable component that encodes or identifies the peptide component. Many proteins have been displayed on the surface of entities that carry the genetic material encoding the protein inside the entity, such as bacteriophages. This format is termed "phage display." Phage display is described, for example, in Ladner et al., U.S. Pat. No. 5,223,409; Smith (1985) *Science* 228:1315-1317; WO 00/70023; WO 92/18619; WO 91/17271; WO 92/20791; WO 92/15679; WO 93/01288; WO 92/01047; WO 92/09690; WO 90/02809; WO 00/70023; Fuchs et al. (1991) *Bio/Technology* 9:1370-1372; Hay et al. (1992) *Hum. Antibody Hybridomas* 3:81-85; Huse et al. (1989) *Science* 246:1275-1281; Griffiths et al. (1993) *EMBO J.* 12:725-734; Hawkins et al. (1992) *J. Mol. Biol.* 226:889-896; Clackson et al. (1991) *Nature* 352:624-628; Gram et al. (1992) *PNAS* 89:3576-3580; Garrard et al. (1991) *Bio/Technology* 9:1373-1377; Rebar et al. (1996) *Methods Enzymol.* 267:129-49; Hoogenboom et al. (1991) *Nuc. Acid. Res.* 19:4133-4137; and Barbas et al. (1991) *PNAS* 88:7978-7982. Phage display systems have been developed for filamentous phage (phage f1, fd, and M13), as well as other bacteriophage (e.g., T7 bacteriophage and lambdoid phages; see, e.g., Santini (1998) *J. Mol. Biol.* 282:125-135; Rosenberg et al. (1996) *Innovations* 6:1-6; Houshmand et al. (1999) *Anal. Biochem.* 268:363-370). The filamentous phage display systems typically use fusions to a minor coat protein, such as gene III protein, and gene VIII protein, a major coat protein, but fusions to other coat proteins such as gene VI protein, gene VII protein, gene 1x protein, or domains thereof can also been used (see, e.g., WO 00/71694).

Other display formats utilize peptide-nucleic acid fusions. RNA and the polypeptide encoded by the RNA can be physically associated by stabilizing ribosomes that are translating the RNA and have the nascent polypeptide still attached. Polypeptide-nucleic acid fusions can be generated by the in vitro translation of mRNA that includes a covalently attached puromycin group, e.g., as described in Roberts and Szostak (1997) *Proc. Natl. Acad. Sci. USA* 94:12297-12302, and U.S. Pat. No. 6,207,446. The mRNA can then be reverse transcribed into DNA and cross-linked to the polypeptide. Typically, high-divalent $Mg^{2+}$ concentrations and low temperature are used. See, e.g., Mattheakis et al. (1994) *Proc. Natl. Acad. Sci. USA* 91:9022 and Hanes et al. (2000) *Nat. Biotechnol.* 18:1287-92; Hanes et al. (2000) *Methods Enzymol.* 328: 404-30; and Schaffitzel et al. (1999) *J. Immunol. Methods* 231(1-2):119-35.

In another display format, the library is a cell-display library. Proteins are displayed on the surface of a cell, e.g., a eukaryotic or prokaryotic cell. Exemplary prokaryotic cells include *E. coli* cells, *B. subtilis* cells, spores; exemplary eukaryotic cells include yeast such as *S. cerevisiae, Hansenula polymorpha, P. pastoris, Kluyveromyces lactis,* insect cells and mammalian cells. Yeast surface display is described, e.g., in Boder and Wittrup (1997) *Nat. Biotechnol.* 15:553-557. Yeast display is particularly suitable for isolating SPCBPs. In one embodiment, variegated nucleic acid sequences encoding scaffold variants are cloned into a vector for yeast display. The cloning joins the variegated sequence with a domain (or complete) yeast cell surface protein, preferably Aga2, Aga1, Flo1, or Gas1. A domain of these proteins can anchor the polypeptide encoded by the variegated nucleic acid sequence by a transmembrane domain (e.g., Flo1) or by covalent linkage to the phospholipid bilayer (e.g., Gas1).

Yet another display format is a non-biological display in which the polypeptide component is attached to a non-nucleic acid tag that identifies the polypeptide. For example, the tag can be a chemical tag attached to a bead that displays the polypeptide or a radiofrequency tag (see, e.g., U.S. Pat. No. 5,874,214).

Methods for displaying SPCBPs and the construction of libraries in a variety of formats are well described in the literature and known to those skilled in the art. Alternatively, to display direct screening of SPCBP, variant libraries are sometimes feasible, for example, when the frequency of antigen-reactive clones is relatively high (as in libraries of VHH genes from immune camel, dromedary or llama), by high-throughput and automated screening methods.

Single-domain antibodies may be isolated from in vitro display repertoires made from single-domain repertoire of certain human variable region fragments, such as human VH or human VL repertoires. In another embodiment, single domain antibodies are isolated from non-immunized, immunized or synthetic VHH repertoires, based on antibody heavy chain domains naturally devoid of light chains (e.g., camel, llama or some shark antibodies).

Cited selection and screening technologies of SPCBP are well established in the field. Antigen-specific polypeptides can be identified from display libraries by direct screening of the library or can be first selected on antigen to increase the percentage of antigen-reactive clones. The selection process is accomplished by a variety of techniques well known in the art, including by using the antigen bound to a surface (e.g., a plastic surface, as in panning), or by using the antigen bound to a solid phase particle that can be isolated on the basis of the properties of the beads (e.g., colored latex beads or magnetic particles), or by cell sorting, especially fluorescence-activated cell sorting (FACS). As will be apparent to one of skill in the art, the antigen-specific affinity reagent is bound directly or indirectly (e.g., via a secondary antibody) to the dye, substrate, or particle. Selection procedures have been extensively described in the literature (see, e.g., Hoogenboom (1997) *Trends Biotechnol.* 15:62-70). Binding of SPCBPs to their respective antigens is carried out using antibody-based assay techniques, such as ELISA techniques, Western blotting, immunohistochemistry, Surface Plasmon Resonance (SPR) analysis, affinity chromatography and the like, according to methods known to those skilled in the art (see, for example, Sambrook et al. 1989 *Molecular Cloning: A Laboratory Manual* 2nd Ed., Cold Spring Harbor Laboratory Press). These techniques are viable alternatives to the traditional hybridoma techniques for isolation of "monoclonal" antibodies (especially when human antibodies are required), which are encompassed by the invention.

2.2.5. Binding Assays for SPCBPs and Mixtures of SPCBPs

The following are possible embodiments of assays for binding assays:

ELISA. Polypeptides encoded by a display library can also be screened for a binding property using an ELISA. For example, each polypeptide is contacted to a microtiter plate whose bottom surface has been coated with the target, e.g., a limiting amount of the target. The plate is washed with buffer to remove non-specifically bound polypeptides. Then, the amount of the polypeptide bound to the plate is determined by probing the plate with an antibody that recognizes the polypeptide, e.g., a tag or constant portion of the polypeptide. The antibody is linked to an enzyme such as alkaline phosphatase, which produces a calorimetric product when appropriate substrates are provided. The polypeptide can be purified from cells or assayed in a display library format, e.g., as a fusion to a filamentous bacteriophage coat. In another version of the ELISA assay, each polypeptide of a library is used to coat a different well of a microtiter plate. The ELISA then proceeds using a constant target molecule to query each well.

Surface Plasmon Resonance (SPR). The binding interaction of a molecule isolated from a library of diversity strands with a target can be analyzed using SPR. For example, after sequencing of a display library member present in a sample, and optionally verified, e.g., by ELISA, the displayed polypeptide can be produced in quantity and assayed for binding the target using SPR. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of surface plasmon resonance). The changes in the refractivity generate a detectable signal, which are measured as an indication of real-time reactions between biological molecules. Methods for using SPR are described, for example, in U.S. Pat. No. 5,641,640; Raether (1988) *Surface Plasmons*, Springer Verlag; Sjolander and Urbaniczky (1991) *Anal. Chem.* 63:2338-2345; Szabo et al. (1995) *Curr. Opin. Struct. Biol.* 5:699-705 and on-line resources provided by BIAcore International AB (Uppsala, Sweden). Information from SPR can be used to provide an accurate and quantitative measure of the equilibrium dissociation constant ($K_d$), and kinetic parameters, including $k_{on}$ and $k_{off}$, for the binding of a biomolecule to a target. Such data can be used to compare different biomolecules. For example, proteins encoded by nucleic acid selected from a library of diversity strands can be compared to identify individuals that have high affinity for the target or that have a slow $k_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $k_{off}$. This information can be combined with structural modeling (e.g., using homology modeling, energy minimization, or structure determination by crystallography or NMR). As a result, an understanding of the physical interaction between the protein and its target can be formulated and used to guide other design processes.

Homogeneous Binding Assays. The binding interaction of candidate polypeptide with a target can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). Another example of a homogenous assay is Alpha Screen (Packard Bioscience, Meriden, Conn.). Alpha Screen uses two labeled beads. One bead generates singlet oxygen when excited by a laser. The other bead generates a light signal when singlet oxygen diffuses from the first bead and collides with it. The signal is only generated when the two beads are in proximity. One bead can be attached to the display library member, the other to the target. Signals are measured to determine the extent of binding. Homogenous assays can be performed while the candidate polypeptide is attached to the display library vehicle, e.g., a bacteriophage. Other methods for determining binding affinities are also suitable such as the use of the Kinexa and Luminex-based systems.

Automated screening. The methods and compositions provided herein are also suitable for automated screening of diversity libraries for finding clones with antigen reactivity. For example, a display library of SPCBPs can be screened for members that bind to a target molecule. The library can be screened directly or first selected on antigen once or several times. Binders from a first round of screening can be amplified and rescreened one or more times. Binders from the second or subsequent rounds are individually isolated, e.g., in a multi-well plate. Each individual binder can then be assayed for binding to the target molecule, e.g., using ELISA, a homogenous binding assay, or a protein assay. These assays of individual clones can be automated using robotics. Sequences of the selected clones can be determined using robots and oligonucleotide primers that allow reading the variable region sequences of the selected clones. Results of the assay and the sequences can be stored in a computer system and evaluated by eye or by using software, e.g., to identify clones that meet particular parameters (e.g., for binding affinity and/or specificity, and for sequence homology).

2.3 The Production of Libraries of Mixture of SPCBPs

SPCBPs are highly suitable for making pharmaceutical compositions of binding proteins binding to multiple targets by co-expression in the same host cell.

2.3.1. Basic Expression Systems for Library Production

The expression vector or vectors comprising the SPCBP genes of interest contain regulatory sequences including, for example, a promoter, operably linked to the nucleic acid(s) of interest. Large numbers of suitable vectors and promoters are known to those of skill in the art and are commercially available for generating the recombinant constructs of the invention. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is hereby incorporated by reference. The following vectors are provided by way of example.

For high-level expression in eukaryotic hosts, for example, exemplary enhancer/promoter regulatory elements include elements derived from SV40, CMV, adenovirus and the like, such as a CMV enhancer/AdMLP promoter regulatory element or an SV40 enhancer/AdMLP promoter regulatory element. See, e.g., U.S. Pat. No. 5,385,839. Eukaryotic promoters include CMV immediate early, HSV thymidine kinase, ubiquitin, elongation factor-1α, early and late SV40, LTRs from retrovirus, mouse metallothionein-I, and various art-known tissue-specific promoters. Suitable promoters for obtaining expression in eukaryotic cells are the CAW-promoter, a mammalian EF1-alpha promoter, a mammalian ubiquitin promoter, or a SV40 promoter. Methods well known to those skilled in the art can be used to construct vectors containing a polynucleotide of the invention and appropriate transcriptional/translational and other regulatory control signals. Eukaryotic expression vectors include the following examples: pWLneo, pSV2cat, pOG44, PXTI, pSG (Stratagene) pSVK3, pBPV, pMSG, and pSVL (Pharmacia). Promoter regions can be selected from any desired gene using CAT (chloramphenicol transferase) vectors or other vectors with selectable markers. Two appropriate vectors are pKK232-8 and pCM7.

Certain of the expression vectors provided in this invention contain Internal Ribosome Entry Sites (IRES). IRES enable eukaryotic ribosomes to enter and scan an mRNA at a position other than the 5' $m^7$ G-cap structure. If positioned internally, e.g., 3' of a first coding region (or cistron), an IRES will enable translation of a second coding region within the same transcript. The second coding region is identified by the first ATG encountered after the IRES. Exemplary IRES elements include viral IRES such as the picornavirus IRES and the cardiovirus IRES (see, e.g., U.S. Pat. No. 4,937,190) and non-viral IRES elements found in 5' UTRs (e.g., those elements of transcripts encoding immunoglobulin heavy chain binding protein (BiP) (D. G. Macejak et al., *Nature*, 35390-4, 1991); *Drosophila Antennapedia* (S. K. Oh et al., *Genes Dev.* 6:1643-53, 1992) and Ultrabithorax (X. Ye et al., *Mol. Cell Biol.*, 17:1714-21, 1997); fibroblast growth factor 2 (S. Vagner et al., *Mol. Cell Biol.*, 15:35-44, 1995); initiation factor eIF4G (Gan et al., *J. Biol. Chem.* 273:5006-12, 1998); proto-oncogene c-myc (Nanbru et al., *J. Biol. Chem.*, 272: 32061-6, 1995; M. Stoneley, *Oncogene*, 16:423-8, 1998); and vascular endothelial growth factor (VEGF) (I. Stein et al., *Mol. Cell Biol.*, 18:3112-9, 1998).

Other regulatory elements are related to chromatin control. These include elements with various names and isolated in various procedures that provides long-term stability and tissue-specific or non-tissue-specific expression of the transgene(s). In general, chromatin control sequences insulate the transcription of genes placed within its range of action but which does not perturb gene expression, either negatively or positively. For example, they modulate (e.g., shield) the regulatory effects of chromatin and nearby sequences in a nuclear environment, typically a chromosomal environment. Thus, insulators can enable sustained and/or appropriate regulatory control of sequences integrated into heterologous regions of a chromosome.

Examples of regulatory elements are the following. Boundaries elements (BEs) or insulator elements define boundaries in chromatin and have a role in defining transcriptional domains in vivo. They lack intrinsic promoter/enhancer activity, but rather are thought to protect genes from the transcriptional influence of regulatory elements in the surrounding chromatin. S/MARs or scaffold-/matrix-attachment regions have been shown to interact with enhancers to increase local chromatin accessibility and can enhance expression of heterologous genes in cell culture lines, transgenic mice and plants. LCR of locus control regions are cis-regulatory elements required for the initial chromatin activation of a locus and sequent gene transcription in their native locations (reviewed by Grossveld 1999). LCSs generally confer tissue-specific expression on linked genes. There are also other elements (STARs or stabilizing anti-repressor elements, ubiquitous chromatin-opening elements or UCOs, etc.) that have been identified and that have some capacity to increase stable transgene expression in industrially relevant host cells such as CHO. Most of these elements function in cis to the transgene, but MARs have also been reported to function when co-transfected in trans with the transgene (Zahn-Zabel et al. (2001) *J. Biotechnology* 87:29-42). Exemplary insulators further include a DNA segment that encompasses the 5' end of the chicken α-globin locus and corresponds to the chicken 5' constitutive hypersensitive site as described in PCT Publication 94/23046, elements described in Bell et al. (2001) *Science* 291:447-50, and STAR from Chromagenics B.V. (Amsterdam, NL).

Figure 1B:
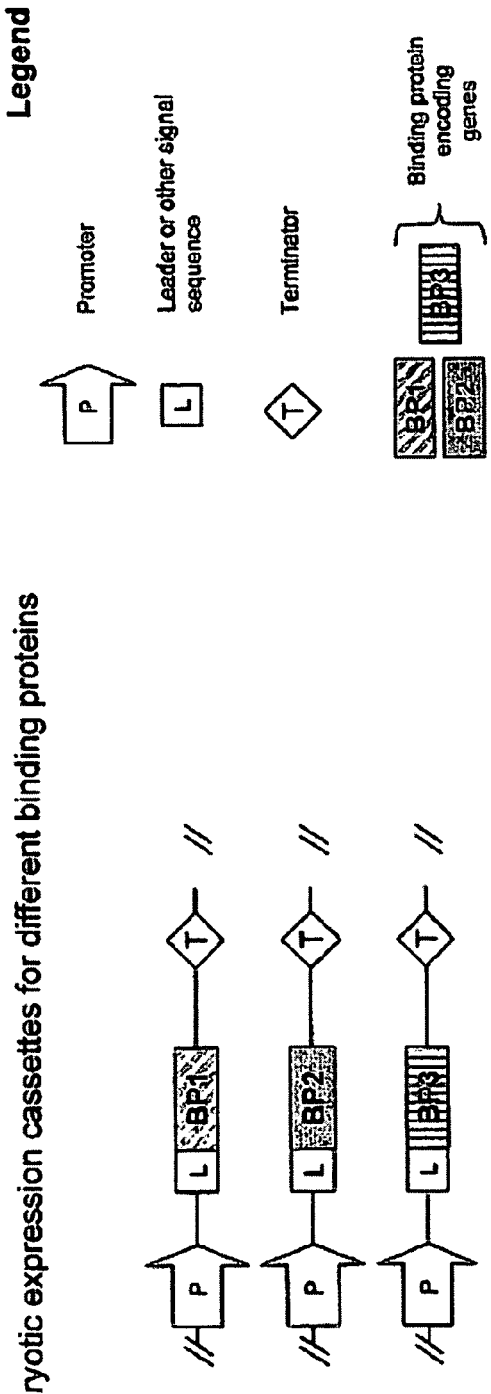
In FIG. 1B, the elements required for prokaryotic expression are depicted. Only the most relevant elements for the invention are indicated and some other features that are well known in the art to be required for expression were omitted (e.g., ribosome binding sites sequences, Shine Dalgamo regions, Kozak consensus sequences etc.).

Mammalian expression vectors will comprise an origin of replication, a suitable promoter and also any necessary ribosome-binding sites, polyadenylation sites, splice donor and acceptor sites, transcriptional termination sequences, and 5' flanking non-transcribed sequences. FIG. 1A presents a schematic picture of the vector backbone and of the expression cassettes for SPCBPs in eukaryotic and typically in mammalian cells. FIG. 1B describes the same for prokaryotic organisms such as *E. coli*. Expression regulatory sequences comprise promoters, enhancers, scaffold-attachment regions, negative regulatory elements, transcriptional initiation sites, regulatory protein binding sites or combinations of those sequences.

Alternatively, sequences that affect the structure or stability of the RNA or protein produced is replaced, removed, added, or otherwise modified by targeting, including polyadenylation signals, mRNA stability elements, splice sites, leader sequences for enhancing or modifying transport or secretion properties of the protein, or other sequences that alter or improve the function or stability of protein or RNA molecules, including RNAi. In addition to the nucleic acid sequence encoding the SPCBP proteins, the recombinant expression vectors can carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). It is typically a gene and/or protein whose presence can be detected directly or indirectly in a cell, for example, a gene and/or a protein that inactivates a selection agent and protects the host cell from the agent's lethal or growth inhibitory effects (e.g., an antibiotic resistance gene and/or protein). For example, the selectable marker gene typically confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification), the neo gene (for G418 selection), the zeocin resistance selectable marker protein (zeo) and the blasticidin selectable marker (bsd). For NSO cells, the Glutamine synthetase system has been extensively used and reviewed as an amplification system (Bebbington et al. 1991, *Bio/Technology* 10:169-175; Barnes et al. *Biotechnol. Bio. Eng.* 73:261). The one antibiotic that is particularly advantageous is zeocin, because the zeocin-resistance protein (zeocin-R) acts by binding the drug and rendering it harmless. Therefore, it is easy to titrate the amount of drug that kills cells with low levels of zeocin-R expression, while allowing the high-expressors to survive. Another possibility is that the selection marker induces fluorescence or a color deposit (e.g., green fluorescent protein and derivatives, luciferase, or alkaline phosphatase).

In an exemplary system for recombinant expression of a modified antibody or antigen-binding portion thereof, a recombinant expression vector encoding at least two SPCBP genes is introduced into dhfr-CHO cells by calcium phosphate-mediated transfection. Within the recombinant expression vector, the two SPCBP genes are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene that allows for selection of CHO cells transfected with the vector using methotrexate selection/amplification. The selected transformant host cells are cultured to allow for expression of the two SPCBP genes. Standard molecular biology techniques are used to prepare the recombinant expression vector, transfect the host cells, select for transformants, culture the host cells and recover the antibody from the culture medium.

Many SPCBPs, by virtue of their compact size and single domain structure, are ideal to be expressed unicellular hosts such as yeast cells or prokaryotic hosts. Fragments from llama dAb libraries have demonstrated excellent solution properties (Tanha et al. 2002, *J. Immunol. Methods* 263:97-969), also compared to mouse and human antibodies and VH regions (Ewert et al. 2002, *Biochemistry* 41:3628-36), and VHH antibody fragments have been produced to high levels in *S. cerevisiae* and *Pichia pastoris* (Thomassen et al. 2002, *Enzyme Microb. Technol.* 30:273-278; Frenken et al. 2000, *J Biotechnol.* 78:11-21; Holt et al. 2003, *Trends Biotechnol.* 11:484-90). Ample systems for the expression of heterologous proteins and, in particular, SPCBP-like antibody fragments, VHH proteins, dAbs, Kunitz domains, affibodies and fluorobodies, in prokaryotics and/or lower eukaryotes have been described. Further, the expression of multimeric proteins in these hosts has been reported.

Libraries of cells expressing SPCBPs are produced by introducing into cells one vector, multiple vectors, or artificial chromosomes (ACE; *Cytometry* 1999 Feb. 1; 35(2):129-33), into which multiple SPCBP-encoding genes have been cloned. After transfection, plasmids are integrated into the host cell genome or exist as an independent genetic element (e.g., episome, plasmids). Vectors, according to the invention, are either single copy vectors or multi-copy vectors. Preferred vectors of the invention include yeast expression vectors, particularly 2µ vectors and centromere vectors. Many of the preferred vectors for expression in eukaryotes are shuttle vectors, known in the art as vectors that can replicate in more than one species of organism. For example, a shuttle vector that can replicate in both *Escherichia coli* (*E. coli*) and *S. cerevisiae* (*S. cerevisiae*) can be constructed by linking sequences from an *E. coli* plasmid with sequences from the yeast 2µ plasmid.

The host of the invention is also a yeast or other fungi, such as *Aspergillus*. In yeast, a number of vectors containing constitutive or inducible promoters is used. For a review see, *Current Protocols in Molecular Biology*, Vol. 2, Ed. Ausubel et al., Greene Publish. Assoc. & Wiley Interscience, Ch. 13 (1988); Grant et al., "Expression and Secretion Vectors for Yeast" in *Methods in Enzymology*, Ed. Wu & Grossman, Acad. Press, N.Y. 153:516-544 (1987); Glover, *DNA Cloning*, Vol. II, IRL Press, Wash., D.C., Ch. 3 (1986); Bitter, "Heterologous Gene Expression in Yeast" in *Methods in Enzymology*, Eds. Berger & Kimmel, Acad. Press, N.Y. 152: 673-684 (1987); and *The Molecular Biology of the Yeast Saccharomyces*, Eds. Strathern et al., Cold Spring Harbor Press, Vols. I and II (1982).

A host of the invention is also a prokaryotic organism, such as *E. coli*. As a representative but non-limiting example, useful expression vectors for bacteria can comprise a selectable marker and bacterial origin of replication derived from commercially available plasmids comprising genetic elements of the well-known cloning vector pBR322 (ATCC 37017). Such commercial vectors include, for example, pKK223-3 (Pharmacia Fine Chemicals, Uppsala, SE) and pGEM1 (Promega, Madison, Wis., US). Other prokaryotic expression plasmids are provided as examples: Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, and pRIT5 (Pharmacia). Particular bacterial promoters include lacI, lacZ, T3, T7, gpt, lambda P, and trc.

Transcriptional control sequences are used to drive expression of transcripts encoding the SPCBP gene or genes. For yeast expression, the following expression plasmids are provided as examples. Expression vectors for use in yeast include YRp7 (Struhl et al., *Proc. Natl. Acad. Sci. U.S.A.* 76:1035-1039, 1979), YEp13 (Broach et al., *Gene* 8:121-133, 1979), pJDB248 and pJDB219 (Beggs, ibid.), and derivatives thereof. Such vectors will generally comprise a selectable marker, such as the nutritional marker TRP1, which allows selection in a host strain carrying a trp1 mutation, or the pOT1 selectable marker, which permits selection in a tpi strain grown in rich medium (Kawasaki and Bell, EP 171,142). Preferred promoters and terminators for use in yeast expression vectors include those from yeast glycolytic genes (Hitzeman et al., *J. Biol. Chem.* 255:12073-12080, 1980; Alber and Kawasaki, *J. Mol. Appl. Genet.* 1:419-434, 1982; Kawasaki, U.S. Pat. No. 4,599,311) or alcohol dehydrogenase genes (Young et al., in Hollaender et al. (eds.), *Genetic Engineering of Microorganisms for Chemicals*, Plenum, New York, 1982, p. 335; and Ammerer, *Meth. in Enzymology* 101:192-201, 1983), the galactose-inducible promoters, pGAL1, pGAL1-10, pGal4, and pGal10; phosphoglycerate kinase promoter, pPGK; cytochrome c promoter, pCYC1; and alcohol dehydrogenase I promoter, pADH1. For *Pichia* expression, as an example, the plasmid pPICZ from Invitrogen is cited as illustration; in this plasmid, the expression cassette for the protein of interest is driven by the methanol-inducible AOX1 promoter of *P. pastoris*. After transformation of *P. pastoris* KM71H cells, cells that have stably integrated a copy of the transgene are selected with zeocin.

Leader or signal sequences are designed for the translocation of nascent polypeptides from ribosomes in the cytoplasm directly into the lumen of the endoplasmic reticulum. Leader sequences, typically hydrophobic, include a sequence that is recognized and cleaved by eukaryotic signal peptidases. The cleavage event produces a mature polypeptide that, absent other signals, is secreted from the cell. Other optional signals that can be provided to the SPCBP genes are signals to target to subcellular compartments such as the nucleus, the plant cell vacuole, the mitochondria, ER-retention signals (e.g., KDEL at C-terminal region of the coding region), and membrane-spanning regions for directly anchoring the SPCBPs in the cell's membrane or equivalent GPI-anchors. Several leader or signal sequences operable in the invention are known to persons skilled in the art, including: Mfα1 prepro, Mfα1 pre, acid phosphatase Pho5, Invertase SUC2 signal sequences operable in yeast; pIII, Pe1B, OmpA, PhoA signal sequences operable in *E. coli*; gp64 leader operable in insect cells; IgK leader, honeybee melittin secretion signal sequences operable in mammalian cells. Particularly preferred eukaryotic signal sequences include those of α-mating factor of yeast, α-agglutinin of yeast, invertase of *Saccharomyces*, inulinase of *Kluyveromyces*, and most preferably, the signal peptide of the Aga2p subunit of α-agglutinin.

Introduction of the recombinant construct into the host cell can be effected, for example, by calcium phosphate transfection (Wigler et al., *Cell* 14:725, 1978; Corsaro and Pearson, *Somatic Cell Genetics* 7:603, 1981; Graham and Van der Eb, *Virology* 52:456, 1973), DEAE, dextran-mediated transfection, or electroporation (Neumann, *EMBO J.* 1:841-845, 1982 and L. Davis et al., *Basic Methods in Molecular Biology*, 1986).

DNA encoding the antibodies of the invention is readily isolated and sequenced using conventional procedures for cloning, DNA preparation and sequencing as described by Sambrook et al., in *Molecular Cloning: A Laboratory Manual, Second Edition*, Cold Spring Harbor, N.Y. (1989), the disclosure of which is hereby incorporated herein by reference. For sequencing, oligonucleotide probes can be used that are capable of binding specifically to the vector sequences surrounding the gene fragments, and the DNA sequence determined by dideoxy-based sequencing (F. Sanger et al. (1977) *PNAS* 74:5463-5467). Once isolated, the DNA-encoding appropriate region of the SPCBP gene is placed into one or more expression vectors as described here and below, which are then transfected into host cells. The host cell is a higher eukaryotic host cell, such as a mammalian cell, a lower eukaryotic host cell, such as a yeast cell, or the host cell is a prokaryotic cell, such as a bacterial cell.

In one embodiment, libraries of SPCBP proteins are made in mammalian cells. Preferred mammalian host cells for expressing the clone antibodies or antigen-binding fragments thereof include Chinese Hamster Ovary (CHO cells) (including dhfr-CHO cells, described in G. Urlaub et al. (1980) *PNAS* 77:4216-4220), used with a DHFR-selectable marker, e.g., as described in R. J. Kaufman et al. (1982) *J. Mol. Biol.* 159:601-621, lymphocytic cell lines, e.g., NS0 myeloma cells and SP2 cells, C127, 3T3, human epidermal A431 cells, Jurkat, U937, HL-60, HEK-293 cells, C2C12, mouse L-cells, Baby Hamster Kidney cells, COS or CV-1 cells, PER.C6 cells (M. G. Pau et al. (2001) *Vaccine* 19:2716-2721), other transformed primate cell lines, normal diploid cells, cell strains derived from in vitro culture of primary tissue, primary explants, and a cell from a transgenic animal, e.g., a transgenic mammal. For example, the cell is a mammary epithelial cell. Other cell types suitable for expression, in particular for transient expression, are simian COS cells (Y. Gluzman (1981) *Cell* 23:175-182) and Human embryonic kidney cells of lineages 293, 295T and 911 (Hek293, 295T, 911).

In another embodiment, libraries of cells expressing SPCBP protein mixtures are produced in lower eukaryotes, such as yeast, or in prokaryotes, such as bacteria (L. C. Simmons et al. (2002) *J. Immunol. Methods* 263:133-147). Potentially suitable yeast strains include *S. cerevisiae, Schizosaccharomyces pombe, Kluyveromyces* strains, *Hansenula polymorpha, P. pastoris, Candida*, or any yeast strain capable of expressing heterologous proteins. Potentially suitable bacterial strains include *Escherichia coli, Bacillus subtilis, Salmonella typhimurium*, or any bacterial strain capable of expressing heterologous proteins.

For some applications, it is required to modify the protein mix produced, for example, by phosphorylation or glycosylation of the appropriate sites, in order to obtain the functional protein. Such covalent attachments of the protein mixtures are accomplished using known chemical or enzymatic methods. Recombinant polypeptides and proteins produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine. The mix of recombinant polypeptides can then be purified using affinity chromatography. Microbial cells employed in expression of proteins can be disrupted by any convenient method, including freeze-thaw cycling, sonication, mechanical disruption, or use of cell lysing agents. Preferably, purification methods independent of antigen recognition are used.

Preferred embodiments of the scaffold of SPCBPs are single-domain antibodies (dAbs) with human antibody segments, preferably based on a human antibody germline segment and preferably DP47, and also camelid "heavy chain only" VHH antibodies, preferably from immunized animals and preferably with sites that are potentially immunogenic when used in humans removed. Other preferred embodiments for scaffolds are lipocalin-based scaffolds and ankryn-based scaffolds. Preferably, scaffolds encode a compact globular protein domain with preferably not more than 250 amino acids, preferably not more than 150 amino acids. Preferred methods of isolation of SPCBPs from libraries of scaffolds are phage and yeast display, expression library screening, ribosome display and enzyme-complementation strategies.

2.3.2. Producing Libraries of SPCBP Mixtures

In one embodiment, a collection of different SPCBP-encoding genes is identified, and this is cloned into appropriate expression vectors (see above and also below for details on specific formats). The library of SPCBPs contains multiple SPCBPs, at least two and preferably not more than 20 and preferably between two and ten. This collection of SPCBP genes is then introduced into host cells in such a manner that host cells will be making multiple and different SPCBPs.

The introduction is done either using conventional transfection techniques, including calcium phosphate or CaCl coprecipitation, DEAE-dextran-mediated transfection, lipofection, or electroporation. In addition, biological vectors, e.g., viral vectors such as retroviral and adenoviral (for eukaryotic cells) or such as filamentous phage or phage lambda (for bacterial cells such as *E. coli*) can be used. Suitable methods for transforming or transfecting host cells can be found in Sambrook et al., *Molecular Cloning: A Laboratory Manual*, 3rd ed., Cold Spring Harbor Laboratory (Cold Spring Harbor Laboratory Press, Cold Spring Harbor, N.Y., 2001), and other suitable laboratory manuals.

In one preferred embodiment, eukaryotic cells are used as host cells, preferably CHO or PER.C6 cells. In that case, transfection can be done in a transient manner, of clones identified that maintain the expression vectors stably inside the cell, this either via stable integration of the transgene into the cell's genome or via episomal vectors. If stable transfection is used, with the possibility to select transfected cell lines for stably integrated copies of the SPCBP-encoding DNAs, the relevant antibody or antibodies are preferably cloned via limiting dilution or cell picking. Also, for such transfection, often restriction-enzyme-digested, linearized plasmids are used to increase the number of transfectants.

Figure 2:
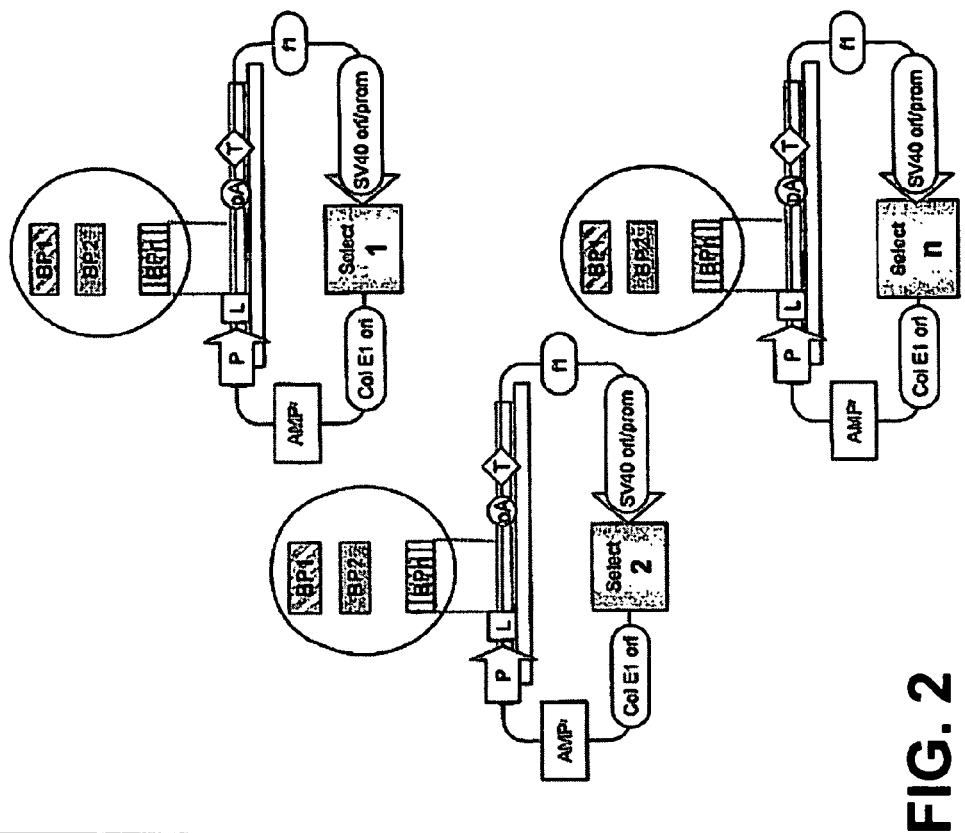
FIG. 2: Schemes depicting different starting points for making libraries of binding proteins. In panel A, multiple genes encoding different binding proteins are cloned into one and the same expression vector that carries one selection marker. In panel B, the binding protein encoding genes are cloned into three different expression vectors, each different in their selection marker (examples for these are illustrated in the text).
Figure 2:
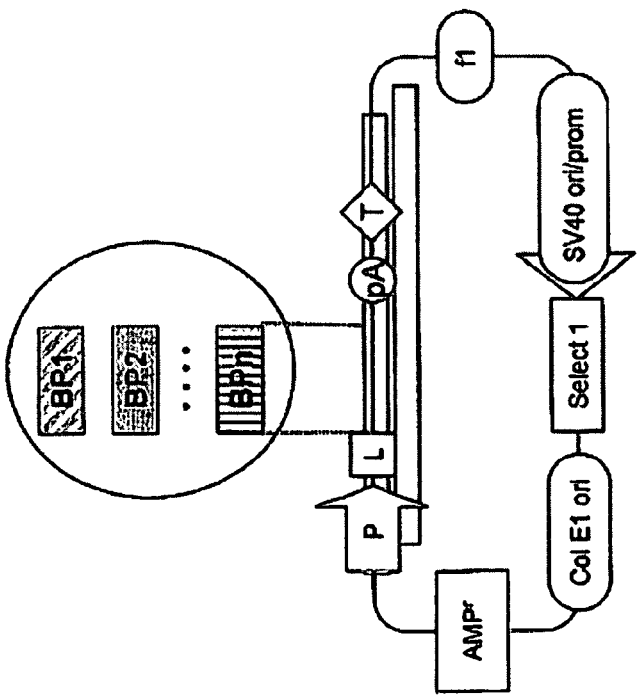
Figure 3:
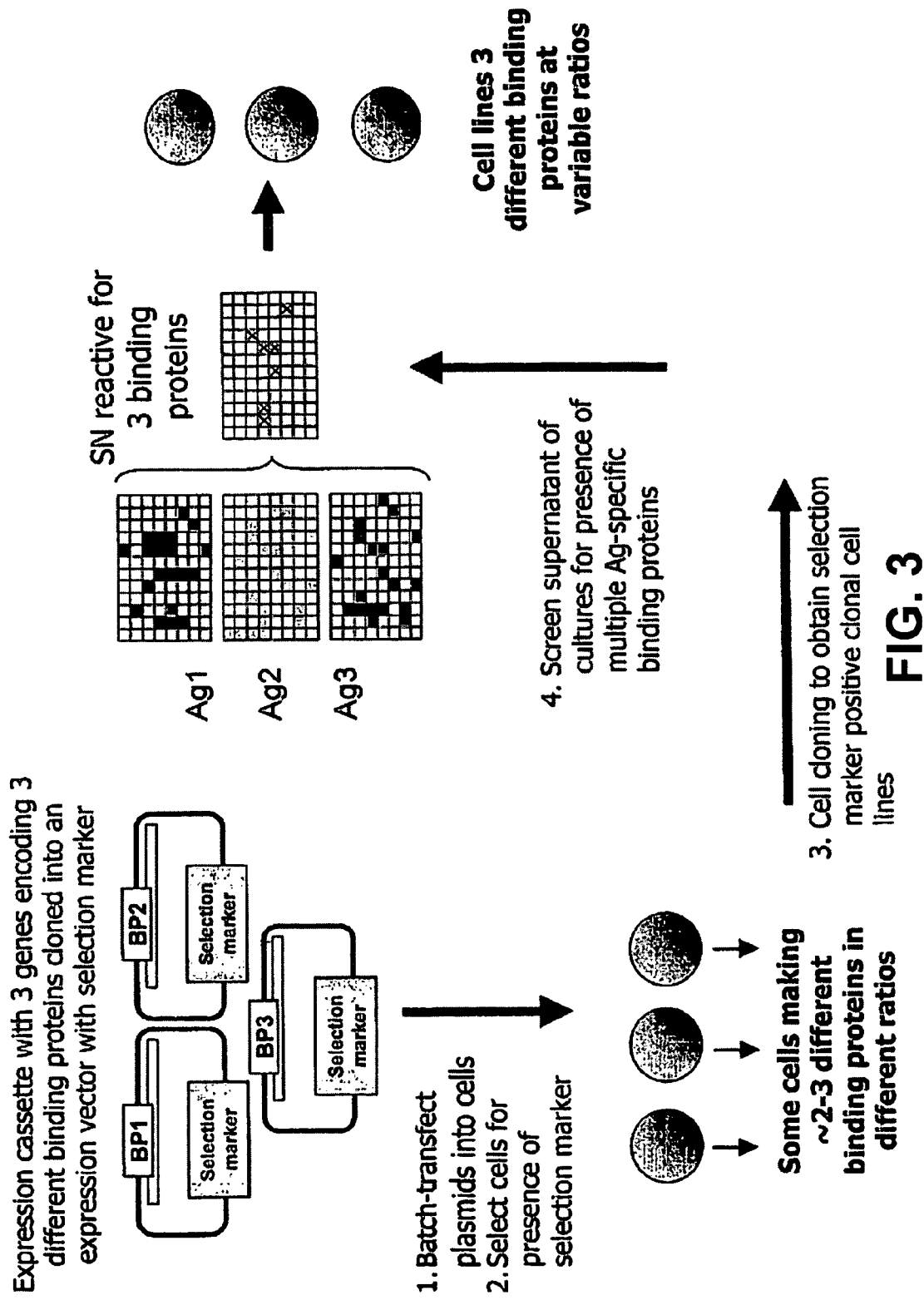
FIG. 3: Route to libraries of three different SPCBPs at different expression ratios based on random integration and screening the supernatant of clonal cell lines by antigen binding (indicated with X on the ELISA plate grid are cell lines that express the three different binding proteins above a certain selection criterion, for example, signal higher than 3× the background signal of the assay). Mixtures are made by transfecting binding protein encoding genes encoding the binding proteins of interest (here number is three), followed by cloning of cell lines, selecting stably producing cell lines, and eventually screening the resulting antibody mixtures for optimal bio-activity.

In one embodiment of this invention, depicted in FIG. 2A and FIG. 3, multiple SPCBP genes (three are indicated in FIG. 3) are cloned into an appropriate expression vector and are then, as a mix of two DNAs, introduced into the host cell. The host cells are transfected and grown under conditions that allow selection for integration of the plasmid into the host's genome. In a preferred embodiment, cells are subjected to a cloning step, in which cells are manipulated and cultured in such manner that populations of cells that are genetically identical with regards to the insertion of the SPCBP-encoding nucleic acids and their place of insertion are obtained. Thus, cell clones are expanded in tissue culture wells in such a manner that the tissue culture wells will contain single clones, with some of the clones expressing SPCBP genes.

Antigen-specific SPCBP secretion can be determined amongst these clones and wells by various methods, preferable by ELISA or equivalent test of the protein mixtures of each well (see also earlier description of binding assays). In FIG. 3, three different ELISA plates representing the reactivity of the same supernatant on three different antigens, is depicted; wells that are reactive with all three antigens thus contain cells that secrete the three SPCBPs. The more extensive screening procedures are described below.

The composition of the SPCBP mixture is influenced by manipulating any one of the parameters that affect the expression level achieved in the host cell and its stability over time. The expression level of a given component is a function of many factors including the regulatory sequences that drive the expression of the component, the choice of the host cell, the method of expression (transient or stable), and, for stable expression, the copy number and site of integration. The expression levels can further be affected by many parameters including choice of the transcriptional regulatory elements (including choice of promoter, enhancer, insulators, anti-repressors, etc).

Thus, the frequency in the library of cell clones expressing single or multiple SPCBP genes will depend on many parameters, including the place of insertion of the transgene(s), the amount of DNA used, the presence of the SPCBP genes on the same plasmid, the transfection frequency, etc. A high likelihood exists that the transgene will become inactive due to gene silencing (McBurney et al., 2002), resulting, for conventional technologies, in a fraction of the recombinant host cells that produce one or multiple SPCBPs. In order to construct a cell line that produces multiple polypeptides at high levels, the different transgenes are generally integrated independently, but that will lead to a reduction in the frequency of cell clones that express SPCBPs.

If two transgenes are transfected simultaneously on two separate plasmids, the proportion of cells that will produce both polypeptides at high levels will be the product of the proportions for single transgenes; if 33% of the cells express one binding protein to a minimal set level that is above a certain selection criterion (for example, three times the background signal in ELISA), only approximately 10% will express two at this level, 3% will express three at the set level, etc. The more SPCBP genes are used for making the library, the more important it will to use an efficient transfection protocol. For example, the expression cassettes with the SPCBP genes can also be part of a viral system such that high levels of transfection/infection efficiency and multiple infections per cell can be achieved.

An important advantage of using SPCBPs is that many of these proteins tend to be single-domain molecules of limited size (average size of 100 to 130 amino acids, and mostly below 200 amino acids). With such relatively small coding regions, on average 300 to 400 nucleotides per SPCBP (without the optional leader and tags), it will be much easier to build expression vectors that incorporate these nucleic acids than, for example, IgG-encoding antibody genes. The coding regions for the latter are approximately 600 and 1400 nucleotides for the two chains, respectively, but many expression vectors utilize genomic Ig DNAs that are even larger in size. Thus, SPCBPs are ideally suited for combining into one expression plasmid, and the invention describes embodiments with two, three, and four to ten different SPCBPs per plasmid. Hence, there is a list of possibilities to combine the various SPCBPs, regulatory elements and procedures, for making libraries of cells expressing multiple SPCBPs and their compositions.

Figure 1B:
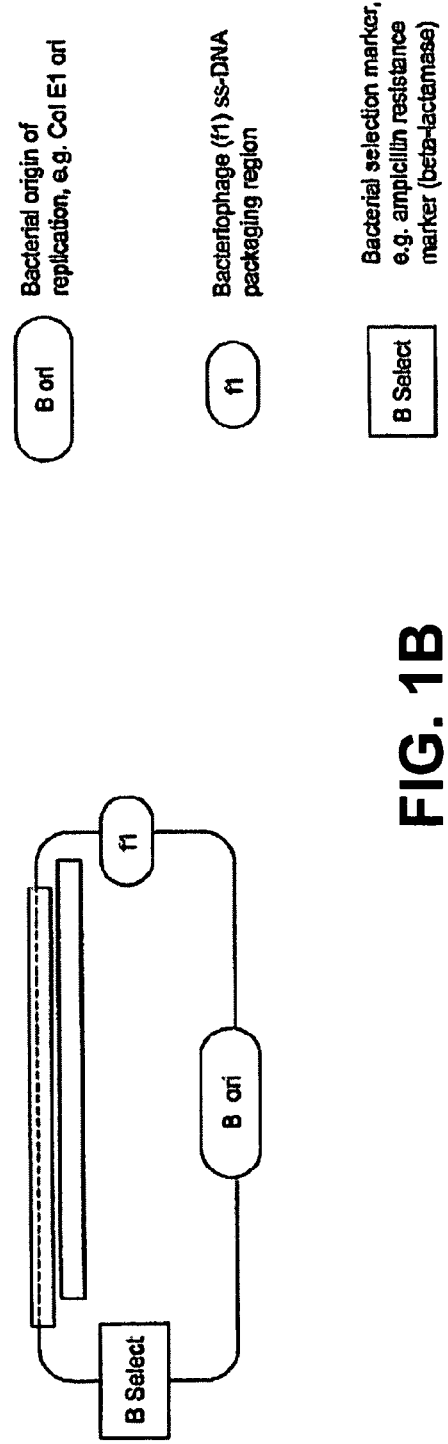
Figure 4:
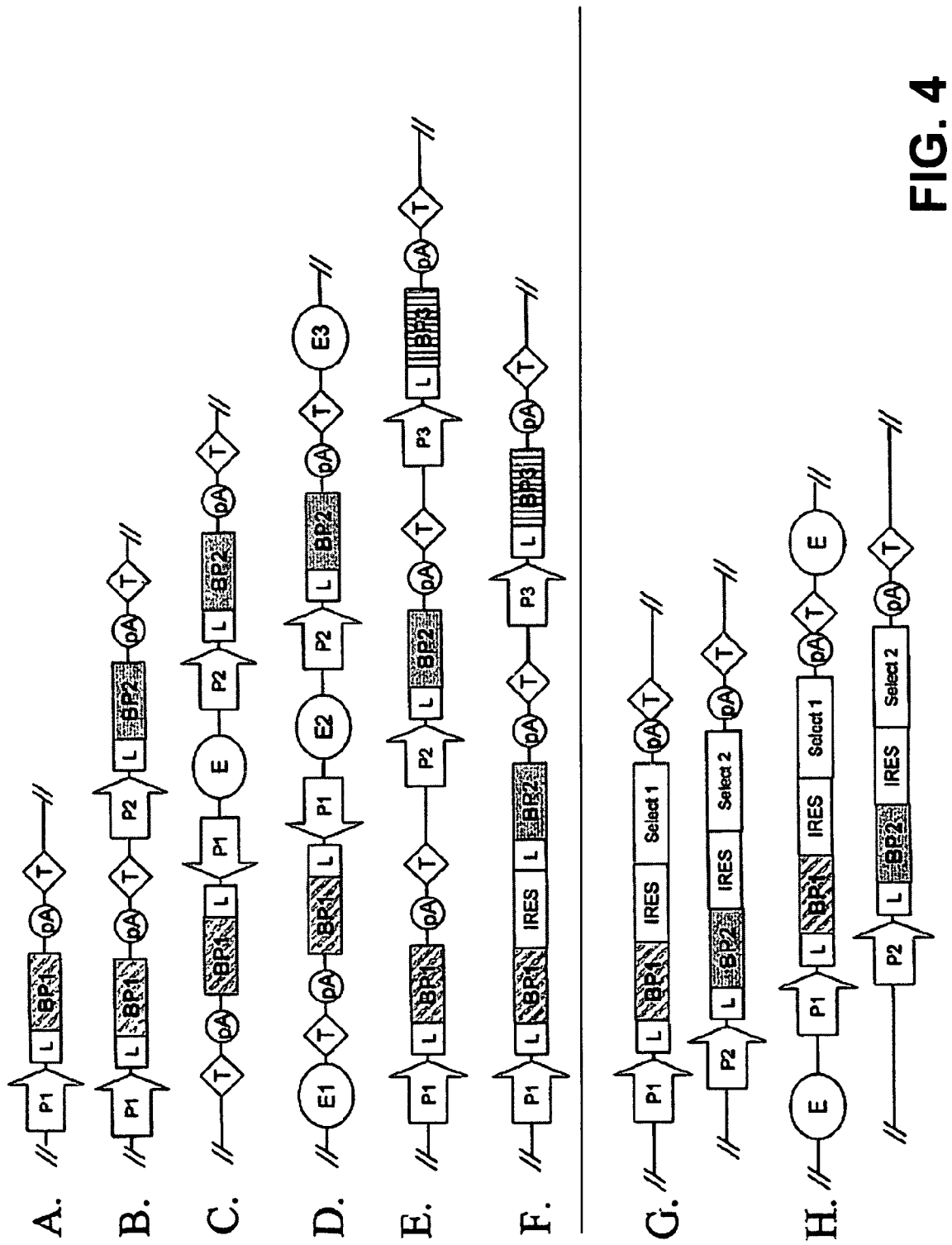
FIG. 4: Expression cassettes for SPCBP genes in the same host cell. Lane A, the basis individual cassette, depicted for one binding protein; Lane B, this cassette contains two BP genes cloned in tandem, but their expression is individually regulated via two different promoters, P1 and P2; Lane C, the two BP genes are cloned into transcriptionally opposite directions and in this example separated by an element that influences the expression/stability/integration frequency (further examples are given in the text); Lane D, same as Lane B, but now additional E-elements are included at the 3' end of each of the two transcriptional units; Lane E, the cassette contains three BP genes cloned in tandem, each with their own promoter, leader, polyadenylation signal and terminator; Lane F, for cases in which two binding proteins should be present in the mixture at roughly similar quantities, an IRES is inserted between two BP genes; in this cassette, the expression of a third BP gene is independently regulated via a different promoter; Lanes G and H, expression cassettes for mediating the expression of two binding proteins, in which the binding protein gene is linked via an IRES element to a selection marker (which is then selected for instead of using the vector backbone-based marker), without Lane G or with additional elements in one cassette to influence expression in Lane H.

In a first embodiment, to obtain libraries with a higher frequency of multiple expressed SPCBPs, the nucleic acids encoding these proteins are cloned into one and the same plasmid that carries one selection marker to select for stable integration. FIG. 4, Lanes A to H, describes suitable protein expression cassettes with multiple SPCBP genes with different orientations that fit into the vector backbone of FIG. 1 or equivalent vectors. Some of these versions carry in cis one or two expression control elements. In a preferred embodiment, "Stabilizing Anti-Repressor elements" (STARs, Kwaks et al. 2003, *Nat. Biotechnol.* 21:553) are cloned at one or both ends of the SPCBP genes (FIG. 4, Lanes A to D). Such elements confer stable and high-level expression of a given transgene as shown in this citation and in WO03106674A2 and WO03004704A2. In this invention, we describe their use to mediate stable and high-level expression for each individual copy of the transgene (see also below, 2.3.3).

In an embodiment of this invention, vectors incorporating any one of these expression cassettes can be combined with vectors that incorporate the same or different expression cassettes listed in FIG. 4, for as long as the mix of vectors when used for transfection introduce multiple SPCBP coding regions into the host cells.

In another embodiment, different vectors are used that each carry a different selection marker (FIG. 2, Panel B; three different markers are described as Select 1-3), cells co-transfected using a highly efficient transfection/transduction/infection method, and dual or triple selection regimens applied. This reduces the total number of surviving cell clones but ensures that each surviving cell will have taken up DNA for each of the three binding proteins. Selection markers are described in the previous section. Another embodiment is to place the selectable marker on the same plasmid and under control of the same promoter as the SPCBP gene, the latter arrangement producing what is known as a dicistronic or polycistronic message.

In a preferred embodiment, selectable marker genes are linked via an IRES sequence downstream of the SPCBP genes (FIG. 4, Lanes G and H). This direct genetic linkage between SPCBP and selection marker provides a guarantee that cell lines selected for the marker will also express the SPCBP protein (as also described in Rees et al. *Biotechniques* 20:102-10). Instead of using an IRES sequence, alternative splicing can be used (Lucas et al. *Nucleic Acids Res.* 1996, 24:1774-9).

Figure 5:
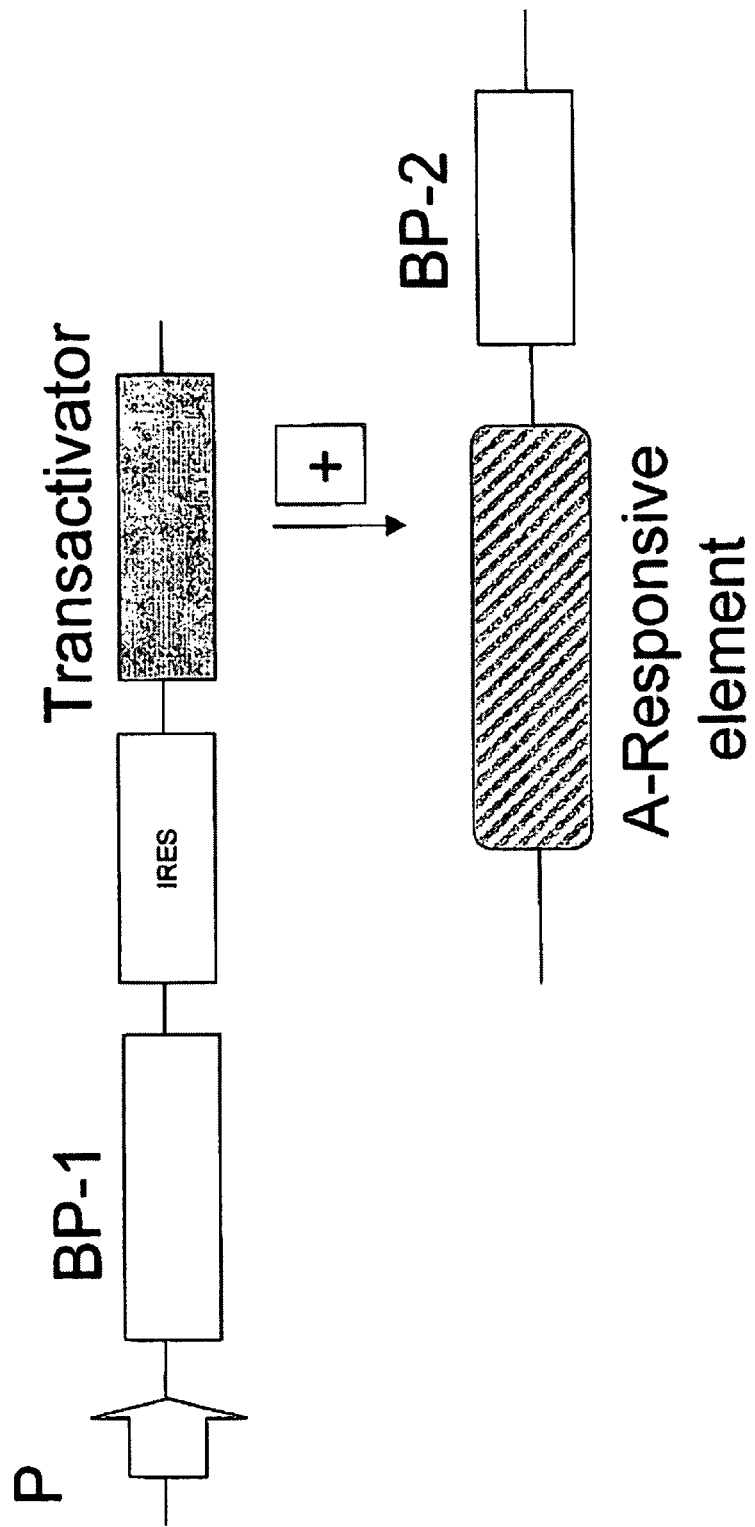
FIG. 5: Dependent expression of SPCBP genes. BP-1 is a first SPCBP that is in under control of a promoter (P). The IRES sequence links the expression of the heavy chain with that of a transactivator; this activates a responsive promoter to induce expression of a second SPCBP, BP-2 (see text for details).

In two other embodiments, the expression of two SPCBPs is made dependent on one another in one of the following ways (FIG. 4, Lane F, and FIG. 5). In the first embodiment, the nucleic acid encoding the first SPCBP is cloned into an expression cassette, such that it will be under the control of a given promoter (typically the strong CMV promoter or other), and such that its coding sequence is followed by an Internal Ribosome Entry Site (IRES). This is immediately followed by a second SPCBP coding region (as depicted in FIG. 4, Lane F). The P1 promoter will now drive the expression of BP-1 and BP-2, leading to an approximate 1:1 expression ratio between these two proteins, even though the second coding region is slightly less well expressed. Thus, if the expression ratio has to be stirred towards a predefined level, the use of IRES sequences is particularly useful. This predefined level is influenced among other factors by the nature of the IRES sequence, and different IRES sequences will mediate different final ratios. Similarly, the expression ratio between three SPCBPs can be linked to one another by using a tricistronic expression cassette, in which the previously described cassette is followed by another IRES and SPCBP coding region. Examples of tricistronic expression systems and of IRES sequences and configurations are described for other systems in the literature (Li et al. *J. Virol. Methods* 115:137-44; When et al. *Cancer Gene Therapy* 8:361-70; Burger et al. 1999, *Appl. Microbiol. Biotechnol.* 52:345-53). Thus, libraries of this invention can also be produced by variegation of the IRES sequences.

In the second approach to influence the expression ratios, which is depicted in FIG. 5, the bicistronic cassette contains, as a first coding region, the first SPCBP and then the IRES sequence is followed by the coding sequence of the transactivator of the tet responsive element (TRE) fused to the activation domain of the herpes simplex VP16 protein (tTa). The nucleic acid encoding the second SPCBP is cloned into an expression cassette such that its expression is regulated via an inducible promoter, for example, the tet-responsive element (TRE), existing of seven copies of the prokaryotic tetracycline operator site fused to a minimal CMV promoter. When introducing both expression cassettes into the same cell (on different vectors or on the same vectors, at the same time or one before the other), the following relation between the expression of the two variable regions will exist: expression of the first SPCBP, which is under control of, for example, a constitutive promoter, will lead to the expression of the tTa protein. This protein activates the TRE-based promoter that drives the second SPCBP's expression. Thus, the second SPCBP's production depends on the first SPCBP's production.

In another embodiment, the production of one set of SPCBPs is made dependent on the production of another set of SPCBPs. In this embodiment, the first collection of SPCBP genes is cloned under control of the TRE element, while a second collection of other SPCBP genes is provided with the IRES and tTa gene, as described above. Similarly as above, every individual SPCBP expressed then triggers the production of another SPCBP. The library is now a library of cells expressing two binding proteins dependably. Other promoter-transactivator systems have been described and are applicable in this concept also. In the same application field, in those cases where the ratios of two particular SPCBPs need to be controlled or fixed, this method of dependent-expression is used to link the expression of two SPCBPs.

In another embodiment, SPCBP genes are sequentially transfected into the host cell. If a library of a limited number SPCBPs needs to be made such that a large number of variants of a small number of binding proteins can be sampled (two to four), the following procedure is used. First, we consider the embodiment for libraries of cells that produce mixes of two SPCBPs. Cells are transfected with the two SPCBP genes cloned into different vectors but the transfection is done sequentially in time. In this embodiment, a second SPCBP gene is transfected into a host cell that already expresses a first SPCBP gene at high level. This is useful for making a library in which only one of the two binding proteins is variegated.

Figure 6:
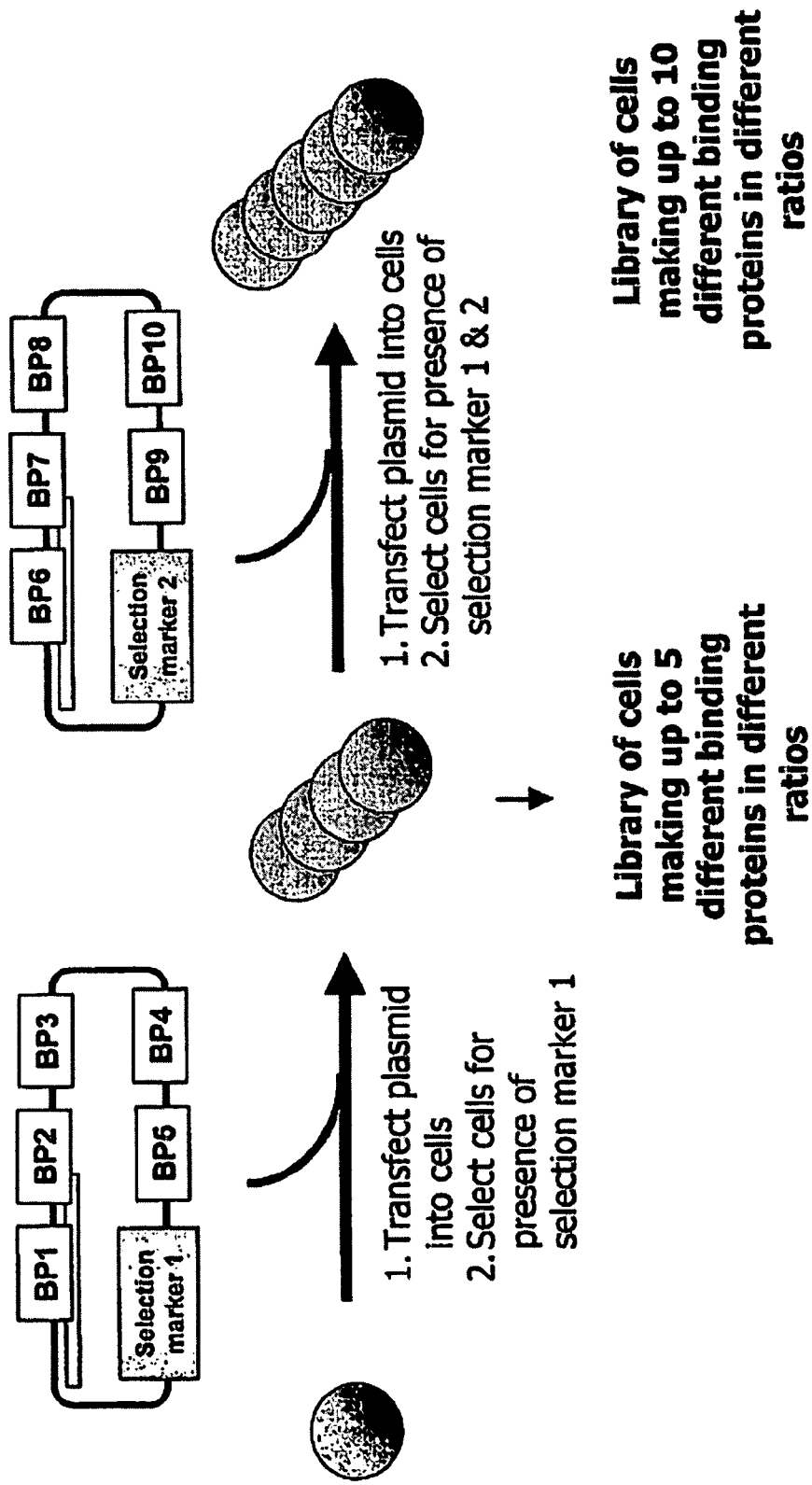
FIG. 6: Method for sequential (introduction of collections of five BP genes into host cells; for each set of five, a different selection marker is selected for. For simplicity, details only for SPCBP genes and selection marker box on plasmids are shown. See text for details.

In another approach, the first SPCBP gene is transfected and not one cell clone but a collection of cells that express a minimal quantity of the SPCBP proteins (but at variable concentration) is identified. These cells are then transfected with the second SPCBP gene as before, and cell clones expressing multiple ratios of the two SPCBPs identified. For making the mixture of two SPCBPs, the DNA encoding the two SPCBs can also be encoded onto the same plasmid (see below). This procedure of carrying out sequential transfections (and, if appropriate, selections of integration in between) is also suitable for making collections of mixture with up to ten different SPCBPs. In this embodiment, cells are transfected with a first collection of maximally five SPCBP genes and cells that express a minimal quantity of the SPCBP proteins (but at variable concentration) isolated. To boost the number of cell clones expressing multiple SPCBPs, the collection of genes is preferably based on the same plasmid, which also carries a first selection marker (see below for a description of such expression cassettes). The selected cell population is subsequently transfected with a plasmid containing the second collection of maximally five SPCBP genes and a second selection marker (FIG. 6). The resulting cells now express libraries of up to ten different binding proteins at highly variable ratios and in many different combinations.

As an alternative embodiment for making cells that express similar or larger diversity, the following procedure is used. First, as before, cell populations are produced that each express up to five different SPCBPs and are resistant based on one selection marker. In parallel, multiple cell populations are produced by transfecting each with plasmids, each carrying five different SPCBP genes and a different selection marker (for example, neo, gpt, zeo, bdl, etc). Second, these cell populations are then fused and selected for the presence of both of the selective markers. These hybrid cells have the potential to express up to ten different SPCBPs. Similarly, this procedure can be repeated if collections of 15 or 20 SPCBPs have to be made. Methods for cell fusion are extensively described in the literature and known to those working in the field; they are similar to those described in Norderhaug et al. 2002 (*Eur. J. Biochem.* 269:3205-10), albeit that here, no subunits but SPCBPs are co-expressed.

In another antibody embodiment, the SPCBP genes are provided via genetic fusion to an appropriate element that provides an anchor onto the host cell surface. Anchors described for the display technology procedures described above are also suitable as anchors for multiple SPCBPs expressed and anchored by same host cell. Preferably, anchor signals include membrane-based proteins, membrane-associated proteins, viral coat proteins and cell wall components that are successfully used for display of protein libraries on host cells, including Lpp-OmpA, lamb and PhoE fusions for display on *E. coli* surface and Aga-2p for display on *S. cerevisiae*.

This is particularly interesting for cell therapy applications, for example, in adoptive transfer of human lymphocytes that have been genetically engineered to express multiple SPCBPs on their cell surface and, as such, are retargeted towards virally infected or tumor cells. At present, an approach in which a single specificity is grafted onto such cells are investigated in the clinic (Wang et al. *Nat. Med.* 1998, 4:168-72). Instead of using a genetic fusion, alternative splicing can be used to obtain a fraction of the binding protein as cell-surface linked (similar to what was described for human antibody genes; and Lucas et al. *Nucleic Acids Res.* 1996, 24:1774-9). This setup also allows a direct screening for antigen binding on the host cell surface, for example, via flow cytometry with fluorescently labeled antigen(s) or target epitopes or SPCBP mimotopes (see further), or a direct selection of cells expressing multiple antigens and at different levels, for example, via cell sorting methods.

In many applications, the SPCBP genes will be provided with a localization signal. The preferred embodiment is to provide a secretion or leader signal, which mediates the secretion of the proteins to the medium (for eukaryotic cells) or periplasmic space (for gram-negative bacteria such as *E. coli*). In another embodiment, libraries of cells expressing SPCBPs that are directed towards an intracellular compartment of the cell are provided. This is done by providing in the expression cassette appropriate localization signals, at either end of the SPCBP coding region, or no signal (for the cytosol), in a similar manner as has been described for antibody scFv fragments and single-domain antibodies (Rabbits, *Trends Mol. Med.* 2003, 9:390-6; Marasco, *Curr. Top. Microbiol. Immunol.* 2001; 260:247-70). Such libraries are particularly useful in target identification and validation studies in which, for example, intracellular targets in the host cell itself are knocked out by one or multiple SPCBPs. For example, for knocking out a complete or redundant pathway, libraries of SPCBPs can be produced that will bind multiple proteins of that pathway. Although particularly interesting as a research tool, this approach is to be considered for gene therapy research and applications, in which one or more gene products have to be knocked out, and the methods of the invention are used to determine the optimal combination of SPCBPs that mediate this effect. For example, by targeting a particular combination of SPCBPs to an intracellular target, it is possible to sequester this molecule, or via the binding of multiple SPCBPs, label it for degradation and removal out of the cytosol. The precise combination of SPCBPs and inter-SPCBP ratios that can mediate this effect without being toxic to the cell, for example, can only be determined by producing a library according to the methods of this invention.

In another embodiment, transient expression protocols are used, which are particularly useful for initial functional testing of SPCBP combinations. Cells, e.g., HekT and COS cells, are transfected with plasmid DNA encoding the multiple SPCBPs. The SPCBP mix is then retrieved from the medium in which the cells are grown. In such cases, the preferred embodiment is to use the SPCBP genes cloned on separate plasmids (e.g., as in FIG. 2, Panel A, and FIG. 3); the ratio between the input plasmid DNAs then also grossly influences and presets the ratios between the expressed SPCBPs. A library of protein mixtures is then made by transfecting in separate experiments different quantities of plasmids into cells and harvesting the products, with multiple plasmids used for a longer time culturing copy numbers.

Expression of mixtures of SPCBPs in some cases is achieved without integrating the DNA into the host cell's genome. In one embodiment, expression plasmids for directing the expression in higher eukaryotes are fitted with elements such as the ori/EBNA-1 from Epstein Barr virus, which allows long-term episomal maintenance in mammalian cells (see, for example, Bode et al. 2001, *Int. J. Gene Ther. Mol. Biol.* 6:33-46). In one embodiment, such plasmids are equipped with multiple SPCBP genes, for example, using the expression cassettes depicted in FIG. 4, Lanes B to F. It is the preferred embodiment that in this case, the SPCBP coding regions are cloned onto the same plasmid. In another embodiment, multiple SPCBP genes are introduced into artificial chromosomes that do not integrate into the host cell genome but independently replicate. This is achieved by site-directed insertion from an ACE-targeting vector by an integrate and requires the plasmid to incorporate recognition sites (see, for example, *Nat. Biotechnol.* 2003 June; 21(6):652-9).

In lower eukaryotes, plasmids that can autonomously replicate plasmids have been described. In one embodiment, preferably two or three expression units (with each one or multiple SPCBP coding regions) are cloned into one of such autonomously replicating expression vectors, preferably a pUC19 or pBr322-based expression plasmid. In another embodiment, the cloning of the preferred two or three expression units (with each one or multiple SPCBP coding regions) is done into two separate plasmids that belong to different compatibility groups and thus replicate in the host cell without interference. Preferred *E. coli*-based plasmids are pBR322-based plasmids (with the Col E1 ori) on the one hand and compatible plasmids, such as those from the pSC101 series (Manen et al. *Gene*, 1997 86(2):197-200), on the other. A preferred set includes pBLUESCRIPT derivatives with oris that mediate low copy number and are compatible, e.g., pBR322 Col E1 ori and p15A oris (Mayer, *Gene* 1995, 163 (1):41-6). Such plasmids preferably bear different selectable markers (kanamycin (KmR) or tetracycline (TcR)). Variability between SPCBPs is achieved here by using plasmids that are maintained at different copy numbers, thus providing a low or high gene dosage to the expression host cell. Combinations between such plasmids are preferred if relative large differences between particular SPCBPs is desirable (10:1 ratios or more).

Transient expression systems of eukaryotic cells are useful for quickly verifying the activity of a SPCBP mix with particular ratios of SPCBPs. The SPCBP coding regions are preferably cloned into separate plasmids (as in FIG. 2, Panel A), and libraries of cells that express different binding proteins and at different ratios are then made by mixing the plasmid DNAs in different combinations and quantities. Overall, the amount of DNA introduced will affect the amount of protein made. Such setups have a number of disadvantages (see earlier) and are not useful for making large collections of SPCBPs; however, transient expression is useful for rapid production of certain binding site combinations.

In one embodiment, the SPCBP coding region is flanked by sequences that mediate site-directed integration into the host cell genome (FIGS. 1A and 1B). Without these, integration of transgenes occurs at random and, usually, several copies of the transgene are integrated at the same time, sometimes in the form of a head-to-tail tandem, with the site of integration and the number of copies integrated varying from one transfected cell to another. The use of recombination sites as depicted in FIGS. 1A and 1B allows the precise site of integration to be targeted by homologous recombination between vector and host cell genome. This provides a means to insert the coding region into a site of high transcriptional activity, with the option to provide a promoter in the transgene or use the one that is present at the site of integration. With "random or homologous recombination-mediated insertion of the SPCBP encoding nucleic acids" is meant any insertion into the genome of the host cell, into the nucleic acids in a subcellular organel, or into an artificial chromosome.

In some of the embodiments, vector format expression cassettes, elements with identical or highly homologous sequence, are used on the same plasmid, preferably, different elements (such as different promoters, different IRES sequences), both for creating libraries with maximally variable ratios between the SPCBP compounds and also to minimize effects of homologous sequences on the stability of the overall construct once introduced into the host cell. If necessary, such elements are provided with non-homologous regions, for example, by replacing or deleting non-vital pieces of the element. In one other embodiment, libraries of cells with highly variable ratios of a limited set of SPCBPs are created by combining variegated regulatory elements with this limited set of SPCBPs. For example, certain nucleotides within the promoter(s) or IRES sequence are variegated, which in some cases, will lead to altered expression of the SPCBP coding region that is under control of such element (s).

In all of these cases, large numbers of cell lines can be screened using automated cell picking devices and cell sorting procedures.

In a further embodiment, preferably, at least two SPCBPs obtained by the methods of the invention are combined with an antibody with paired domains, preferably a single-chain Fv fragment with paired VH and VL domains or a Fab domain, with paired heavy chain Fd and light chains, preferably in such manner that these binding proteins share similar features that provide a single path for purification of the mixture.

In another embodiment, one SPCBP obtained by the methods of the invention is combined with an antibody with paired domains, preferably a single-chain Fv fragment with paired VH and VL domains or a Fab domain, with paired heavy chain Fd and light chains, preferably in such manner that these binding proteins share similar features that provide a single path for purification of the mixture.

2.3.3. Regulating the Stability of SPCBP Gene Expression in the Context of the Production of Multiple Binding Proteins in the Same Host Cell Nucleic acids encoding single polypeptide chains can be co-expressed in the same cell to make mixtures of different functional binding sites. It will, however, also be important to control the expression of the individual variable regions and their expression ratios, because this will effect the composition of the final binding protein mixture.

The expression level and the stability of the expression is, among others, a function of the site of integration of the transgene: if the transgene is integrated close to or within inaccessible chromatin, it is likely that its expression will be silenced. In this invention, we describe the use for the production of mixtures of SPCBP in the same cell, of elements that, when flanking the antibody genes, will increase the predictability of the expression level, the yield, and improve stability. A STAR (STabilizing Anti-Repressor) sequence (or anti-repressor, or STAR element; the terms will be used interchangeably herein) is a naturally occurring DNA element that was isolated from eukaryotic genomes on the basis of its ability to block transgene repression. Preferably, the STAR elements are derived from the human genome. A STAR sequence comprises the capacity to influence transcription of genes in cis and/or provide a stabilizing and/or an enhancing effect. It has been demonstrated that when STAR elements flank transgenes, the transgene expression level of randomly selected recombinant cell lines can be increased to levels approaching the maximum potential expression of the transgene's promoter. Moreover, the expression level of the transgene is stable over many cell generations and does not manifest stochastic silencing. Therefore, STAR sequences confer a degree of position-independent expression on transgenes that is not easily possible with conventional transgenic systems. "Position independence" means that transgenes that are integrated in genomic locations that would result in transgene silencing are, with the protection of STAR elements, maintained in a transcriptionally active state. Thus, anti-repressor elements provide a high level of predictability of expression, high levels of expression and stable expression over time (Kwaks et al. 2003, *Nat. Biotechnol.* 21:553). Such elements confer stable and high-level expression of a given transgene as shown in this citation and in this invention, we describe its use to mediate stable and high-level expression for each individual copy of a mixture of transgenes, encoding multiple SPCBPs. A variety of such elements and other systems to achieve a similar result have been identified in the art, including locus control regions (LCRs), chromatin-opening elements, artificial chromosomes (e.g., ACE technology from Chromos Molecular Systems Ltd.), matrix-attachment regions (MAR), scaffold-attachment region and ubiquitous chromatin-opening (UCO) elements. For example, LCRs are transcriptional regulatory elements that possess a dominant chromatin-remodeling and transcriptional-activating capability conferring full physiological levels of expression on a gene linked in cis when integrated into the host cell genome. In the following section, the invention is described for "anti-repressor elements" but other, different control elements, such as the ones mentioned, and inasmuch as they provide the opportunity to regulate the high-level expression of multiple genes, is equally suitable to achieve a controlled expression of the different SPCBP genes.

In one embodiment, at least one of the SPCBP genes is flanked by one anti-repressor element or by two identical or two different anti-repressor elements located at either end of the SPCBP gene (FIG. 4, Lanes B and C). In another embodiment, more than one or possibly all of SPCBP genes that need to be expressed are flanked by anti-repressor elements. In one embodiment, all of the maximally five different SPCBP genes are based on the same plasmid; in another they are on separate plasmids. In another embodiment, CHO cells are used as host; in another embodiment, PER.C6 cells are used.

The manufacture of mixtures of SPCBPs expressed in the same cell line will require a stable ratio of the various chains, in such manner that the resulting SPCBP mixture after manufacture, even at GMP conditions, has a stable composition. Such stable compositions can then translate into stable biological activity and stable toxicity profile. If the expression of only one SPCBP would change, it could affect the composition and, therefore, also alter its biological activity. The provision of elements that yield a more predictable, and copy number-associated, expression level is also important to build cell lines that express stable levels of different SPCBPs. If, for example, in the library a total five SPCBPs have to be expressed, the anti-repressor elements is used to border those SPCBP genes, the relative ratios of which should be approximately equimolar. By using such elements, a higher number of SPCBP genes can be introduced without compromising the stability of the resulting cell line. Thus, multiple SPCBP genes can be introduced, where the number of integrated copies for each SPCBP gene will also, to some level, reflect its absolute expression level. With such elements, it will be much easier and more rapid to alter or predetermine the ratios of expression levels of some or all of the SPCBP genes, for example, by manipulating the ratios of the DNAs encoding the SPCBP genes at the time of the transfection.

This also explains the preferred incorporation of such anti-repressor elements in vectors to be used for creating SPCBP-expressing cell libraries; anti-repressor elements preferably inserted are the STAR elements cited above.

Another embodiment utilizes, as expression control elements, matrix-attachment regions, or MARs. MARs have been shown to be associated with remodeling of the surrounding chromatin, thus promoting transgene expression in the form of an active artificial transcriptional domain. MAR elements are highly active when a transgene cassette is co-integrated within the chromosome of the eukaryotic host cell, but also when a transgene cassette is not integrated. MARs function by insulating nearby genes from the effect of surrounding chromatin, thereby increasing copy-number dependent, position-independent, expression of genes. For this reason, MARs increases the number of independently transformed cells that express the protein and promotes a higher amount of recombinant protein produced by these cells. Overall, MARs accelerates clone isolation and allows higher production rates. Examples of MARs can be found in Zahn-Zabel et al. (2001) *J. Biotechnology* 87:29-42 and in WO02074969A2. The chicken lysozyme 5' MAR has been described to significantly improve stable transgene expression in CHO cells.

MARs and STARs can be positioned on either side of the DNA sequence to be transcribed. For example, the elements can be positioned about 200 bp to about 1 kb, 5' from the promoter, and at least about 1 kb to 5 kb from the promoter, at the 3' end of the gene of interest. In addition, more than one element can be positioned 5' from the promoter or at the 3' end of the transgene. For example, two or more elements can be positioned 5' from the promoter. The element or elements at the 3' end of the transgene can be positioned at the 3' end of the gene of interest, or at the 3' end of a 3' regulatory sequence, e.g., a 3' untranslated region (UTR) or a 3' flanking sequence. Chromatin-opening elements can be flanking on both ends of the expression cassette (FIG. 4, Lane D) or placed 5' of the expression cassette (FIG. 4, Lane C). In particular, when multiple SPCBPs expression cassettes and multiple regulatory elements, such as STAR and UCOs, have to be introduced into one and the same plasmids, there are size limitations, and preferably, elements are used that have activity towards both ends of the element such that they can be provided in the middle of an expression cassette (FIG. 4, Lane C). Since MARs have also been reported to function when co-transfected in trans with the transgene (Zahn-Zabel et al. (2001) *J. Biotechnology* 87:29-42), they have the advantage that no DNA-cloning step is required to physically link them to SPCBP expression cassette(s). In that case, size of the MAR element or of the expression vector carrying the SPCBP cassettes is no longer a limitation. Nevertheless, MAR elements as small as 1.3 kb have been described, thus multiple in cis inclusions are feasible. MARs have also been reported to be added both in cis and in trans, and in this configuration, increase expression levels of antibodies in CHO cells 14-fold. One other function of these elements, besides their effect on stability, is that they will also increase the number of independently transformed cells that express the protein and promotes higher amounts of the recombinant protein. Clone isolation and production levels are higher overall, thus, in the preferred embodiment, this invention is practiced by using these elements for making cell lines producing multiple SPCBPs and libraries thereof.

Preferred embodiments are to employ per expression vector used in the library construction not more than five binding protein coding regions and preferably three per vector. Preferably, per plasmids do not contain more than three promoters and three IRES sequences and not more than six STAR or MAR elements.

It is preferred to limit the expression vector's size to 20 kb and if more binding proteins than five are required in the mix, these cannot be functionally encoded in a plasmid that is less than 20 kb in size to use two different plasmids. The preferred route to libraries with more than five binding proteins is to use two sets of expression vectors and the preferred route is depicted in FIG. 6.

The starting SPCBP for constructing the library are preferred to display affinity values for binding to their target of at least 1 micromolar, preferably at least 100 nanomolar, preferably at least 10 nanomolar, and preferably between 0.1 and 10 nanomolar. A target epitope for a SPCBP is the region on the target that is recognized or bound by the SPCBP. Two or more SPCBPs can have overlapping yet different target epitopes, for example, if the binding proteins compete for binding with one another but display a different binding site chemistry for recognition of the target due to the use of different amino acids in the binding site. For example, two SPCBPs that recognize TNF and neutralize this cytokine and compete with one another for binding to TNF, are defined to recognize different target epitopes on TNF if the amino acids that are located in or near the binding site of the SPCBP are different between the two SPCBPs.

Libraries contain preferably less than 10 binding proteins that are present on preferably less than 5 different plasmids, preferably between 3 and 5 different plasmids. Preferred compositions selected for optimal activity contain SPCBP mixtures with preferably not more than 10 separate binding proteins. Preferred are at least 2 and not more than 5 separate binding proteins, and preferably three separate binding proteins. Libraries are preferably not more than 100,000 cell clones in size, preferably between 10 and 1,000 cell clones in size.

2.3.4 Screening and Analysis of Protein Mixtures

The invention is also suitable for the screening of mixtures of proteins that have a defined binding specificity. The genes encoding these compounds are introduced as a mixture into a host cell as above (in FIG. 3, an example is given of three different SPCBP proteins), and individual clones that have integrated some or multiple copies of the genes encoding the various variable regions expanded. In a first embodiment, a binding assay is used to screen these libraries. In the way described above, applied to antibodies, the supernatants of the resulting cell lines are screened for reactivity towards the various antigens or in a bioassay, as was described ELISA, SPR, etc. For this, large numbers of cell lines can be screened using robots for manipulating tissue culture and ELISA plates. Besides binding in an in vitro assay, it is also described that the mixtures of SPCBPs are tested in functional, activity and bio-assays. The following assays are described by way of example, but many more will be applicable to this screening stage.

Mixtures of SPCBPs are assayed for functional activity either in vitro or in vivo.

Immunological and Efficacy Assays. Some functional assays can monitor an activity that depends on an arm of the immune system. Mostly, SPCBPs will lack the Fc-mediated effector functions, but if these are provided, for example, by engineering of the scaffold itself, by combination with another SPCBP or with an Fc region or anti-SPCBP antibody, following immunological assays are feasible. In vitro assays for immunoglobulin effector domain activity, e.g., cytotoxic activity, are used to detect the ability of SPCBPs to deliver immune effector functions against a target. For example, cell culture assays can be used to assay complement-dependent cytotoxicity (CDC) or antibody-dependent cell-mediated cytotoxicity (ADCC) mediated by a SPCBP mix. One ADCC assay is described below. The Cr-release assay can be used to assay cell-mediated cytotoxicity. Peripheral blood lymphocytes (PBL) are prepared as effector cells, while target cells that express the targeted molecule are loaded with $^{51}$Cr. The target cells are washed and then seeded into a flat bottom microtiter plate. PBLs are added to the target cells in combination with the SPCBPs. Maximum release is determined by the addition of Tween-20 to target cells, whereas minimal release is determined in the absence of PBLs. After overnight incubation, $^{51}$Cr released into the supernatant is counted in a scintillation counter. In vivo assays include injecting a SPCBP mix into an animal, e.g., an animal model of a diseased state. For example, the animal can be a transgenic animal, e.g., expressing an oncogene in a particular tissue. In another example, the animal is a mouse with a xenograft of tumor cells (e.g., human tumor cells). The efficacy of the SPCBP mix (or other ligand) can be assayed by comparing time, size, and number of tumors formed compared to untreated or control-treated animals. In an implementation in which the xenografted mouse is a nude mouse, the mouse can be injected with human PBLs to reconstitute the immune system. Other physiological parameters of the SPCBP mix can also be monitored including immunogenicity, clearance, and so forth.

Cellular Activity Assays. Other cellular activity assays include assessments of cellular pH and calcium flux, and assessments of a cellular behavior, e.g., apoptosis, cell migration, cell proliferation, and cell differentiation.

Numerous cell culture assays for differentiation and proliferation are known in the art. Some examples are as follows:

Assays for embryonic stem cell differentiation (which will identify, among others, proteins that influence embryonic differentiation hematopoiesis) include, e.g., those described in: Johansson et al. (1995) *Cellular Biology* 15:141-151; Keller et al. (1993) *Molecular and Cellular Biology* 13:473-486; McClanahan et al. (1993) *Blood* 81:2903-2915.

Assays for lymphocyte survival/apoptosis (which will identify, among others, proteins that prevent apoptosis after superantigen induction and proteins that regulate lymphocyte homeostasis) include, e.g., those described in: Darzynkiewicz et al., *Cytometry* 13:795-808, 1992; Gorczyca et al., *Leukemia* 7:659-670, 1993; Gorczyca et al., *Cancer Research* 53:1945-1951, 1993; Itoh et al., *Cell* 66:233-243, 1991; Zacharchuk, *Journal of Immunology* 145:4037-4045, 1990; Zamai et al., *Cytometry* 14:891-897, 1993; Gorczyca et al., *International Journal of Oncology* 1:639-648, 1992.

Assays for proteins that influence early steps of T-cell commitment and development include, without limitation, those described in: Antica et al., *Blood* 84:111-117, 1994; Fine et al., *Cellular Immunology* 155:111-122, 1994; Galy et al., *Blood* 85:2770-2778, 1995; Toki et al., *Proc. Nat. Acad. Sci. USA* 88:7548-7551, 1991.

Dendritic cell-dependent assays (which will identify, among others, proteins expressed by dendritic cells that activate naive T-cells) include, without limitation, those described in: Guery et al., *J. Immunol.* 134:536-544, 1995; Inaba et al., *Journal of Experimental Medicine* 173:549-559, 1991; Macatonia et al., *Journal of Immunology* 154:5071-5079, 1995; Porgador et al., *Journal of Experimental Medicine* 182:255-260, 1995; Nair et al., *Journal of Virology* 67:4062-4069, 1993; Huang et al., *Science* 264:961-965, 1994; Macatonia et al., *Journal of Experimental Medicine* 169:1255-1264, 1989; Bhardwaj et al., *Journal of Clinical*

*Investigation* 94:797-807, 1994; and Inaba et al., *Journal of Experimental Medicine* 172:631-640, 1990.

Assays for T-cell or thymocyte proliferation include without limitation those described in: *Current Protocols in Immunology*, Ed. by J. E. Coligan, A. M. Kruisbeek, D. H. Margulies, E. M. Shevach, W. Strober, Pub. Greene Publishing Associates and Wiley Interscience (Chapter 3,—In vitro assays for Mouse Lymphocyte Function 3.1-3.19; Chapter 7, Immunologic studies in Humans); Takai et al., *J. Immunol.* 137:3494-3500, 1986; Bertagnolli et al., *J. Immunol.* 145: 1706-1712, 1990; Bertagnolli et al., *Cellular Immunology* 133:327-341, 1991; Bertagnolli, et al., *I. Immunol.* 149:3778-3783, 1992; Bowman et al., *I. Immunol.* 152:1756-1761, 1994.

Assays for cytokine production and/or proliferation of spleen cells, lymph node cells or thymocytes include, without limitation, those described in: *Polyclonal T cell stimulation*, A. M. Kruisbeek and E. M. Shevach, In *Current Protocols in Immunology*, Coligan eds. Vol. 1 pp. 3.12.1-3.12.14, John Wiley and Sons, Toronto, 1994; and *Measurement of mouse and human interleukin gamma.*, R. D. Schreiber, In *Current Protocols in Immunology*, Coligan eds. Vol. 1 pp. 6.8.1-6.8.8, John Wiley and Sons, Toronto. 1994.

Assays for proliferation and differentiation of hematopoietic and lymphopoietic cells include, without limitation, those described in: *Measurement of Human and Murine Interleukin* 2 *and Interleukin* 4, K. Bottomly, L. S. Davis and P. E. Lipsky, In *Current Protocols in Immunology*, J. E. e.a. Coligan eds. Vol. 1 pp. 6.3.1-6.3.12, John Wiley and Sons, Toronto, 1991; de Vries et al., *J. Exp. Med.* 173:1205-1211, 1991; Moreau et al., *Nature* 336:690-692, 1988; Greenberger et al., *Proc. Natl. Acad. Sci. U.S.A.* 80:2931-2938, 1983; Measurement of mouse and human interleukin-6, R. Nordan, In *Current Protocols in Immunology, J. E. e.a. Coligan eds. Vol.* 1 pp. 6.6.1-6.6.5, John Wiley and Sons, Toronto, 1991; Smith et al., *Proc. Natl. Acad. Sci. U.S.A.* 83:1857-1861, 1986; *Measurement of human Interleukin*-11, F. Bennett, J. Giannotti, S. C. Clark and K. J. Turner, In *Current Protocols in Immunology*, Coligan eds. Vol. 1 pp. 6.15.1 John Wiley and Sons, Toronto, 1991;

Assays for T-cell clone responses to antigens (which will identify, among others, proteins that affect APC-T cell interactions as well as direct T-cell effects by measuring proliferation and cytokine production) include, without limitation, those described in: *Current Protocols in Immunology*, Ed. by J. E. Coligan, A. M. Kruisbeek, D. H. Margulies, E. M. Shevach, W. Strober, Puh. Greene Publishing Associates and Wiley-Interscience (Chapter 3, In vitro assays for Mouse Lymphocyte Function; Chapter 6, Cytokines and their cellular receptors; Chapter 7, Immunologic studies in Humans); Weinberger et al., *Proc. Natl. Acad. Sci. USA* 77:6091-6095, 1980; Weinberger et al., *Eur. J. Immun.* 11:405-411, 1981; Takai et al., *J. Immunol.* 137:3494-3500, 1986; Takai et al., *J. Immunol.* 140:508-512, 1988.

Other assays, for example, can determine biological activity with respect to endothelial cell behavior, nerve cell growth, nerve cell migration, spermatogenesis, oogenesis, apoptosis, angiogenesis, endocrine signaling, glucose metabolism, amino acid metabolism, cholesterol metabolism, erythropoiesis, thrombopoeisis, and so forth.

Cell Binding Assays. The functionality of a SPCBP mix can also be used in a cell binding assay. The SPCBP mix can be labeled bound to a population of cells that includes cells that present a target recognized by the SPCBP mix. The population can also include cells that do not present the target, or that present a related molecule that is discriminated by the SPCBP mix.

In a first example, the SPCBP mix is tested using FACS analysis. The SPCBP mix is labeled with a fluorophore, either directly or using a secondary antibody and bound to cells. Then, the cells are passed through a FACS apparatus to count the number of cells bound by the SPCBP mix. The cells can also be contacted with another antibody labeled with a fluorophore that is detectable using a different channel. Binding of the mix can be correlated on a cell-by-cell basis with binding of the SPCBP mix (e.g., using a 2D scatter plot).

In a second example, the SPCBP mix is assayed using immunohistochemistry. The SPCBP mix is contacted to a histological section. The section is washed, and bound SPCBP mix is detected, e.g., using standard methods.

In a third example, the SPCBP mix is assayed in vivo, e.g., in a subject organism. The SPCBP mix is labeled, e.g., with a NMR contrast reagent or other traceable reagent. The SPCBP mix is administered to the subject and, after an appropriate interval, its localization within the subject is detected, e.g., by imaging the subject organism.

Any one of the assays described above can be used to determine the mixture with the most optimal efficacy and, thus, the cell clone producing this mixture. Mixtures of SPCBPs have antagonistic, agonistic (or activating) effects on certain ligands, and effects are additive or synergistic compared with the individual components. The mixture can contain SPCBP that negates a positive effect exerted by another SPCBPs, thus, it is important to screen for net functional activities rather than adding the activity of individual compounds of the mix. The presence of additive and synergic effects also implies that certain SPCBPs that are below a certain selection criterion when tested as individual compounds and that are normally not pursued, in combination with other SPCBPs show a strong and significant biological effect. The preferred use of SPCBP mixtures in inflammatory and infectious diseases is in applications in which the different protein compounds of the mix exert antagonistic effect, such as inhibition of a receptor-ligand interaction due to steric hindrance or indirect effects, such as interference with the ligand-binding site on the receptor or the receptor-binding site on the ligand.

Other preferred uses include the use of SPCBP mixtures with per mass more potency or activity when compared with antibodies with paired domains such as scFv, Fab and IgG molecules. Such increased potency is due to synergistic effects between the individual components of the mixture. Single-domain antibodies have been described to be particularly suitable for recognizing viral canyon sites, in particular, also of conserved sites that are normally hidden deep inside the pathogen's genetically variable coat protein. Preferred applications, therefore, include the neutralization of viruses and pathogens that are more readily recognized by SPCBPs than by antibodies with paired domains such as scFv, Fab and IgG molecules. Similarly, the inhibition of enzymes is a preferred use for SPCBPs. Since SPCBPs based on the immunoglobulin scaffold (dAbs, camel antibodies) are produced in lower eukaryotes at higher levels than antibody fragments with paired domains such as scFv, Fab and diabody molecules, the preferred production host for SPCBP mixtures based on such scaffolds are lower eukaryotes such as *Pichia pastoris, Hansenula Polymorpha* and *S. cerevisiae*. For the production of mixture of SPCBPs that are fused too glycosylated domains, the preferred host is CHO.

In one embodiment, the library of cells expressing multiple SPCBPs that are also associated with the cell surface (see above), is subjected to FACS sorting. Similarly, cell sorting can be used for more rapid cloning of cell clones. With respect to FACS, the cells are sorted using a fluorescent-activated cell sorter (e.g., a sorter available from Becton Dickinson Immunocytometry Systems, San Jose Calif.; see also U.S. Pat. Nos. 5,627,037; 5,030,002; and 5,137,809). As each cell passes through the sorter, a laser beam excites fluorescent compounds that are attached to the cell. A detector assesses the amount of light emitted by such fluorescent compound, if present. The amount of label bound to each cell is quantified and, if at least a set level of amount of label is detected, an electrostatic field is generated to deflect the cell from its default path. Deflected cells are thus separated and collected. As a result, cells with low or no SPCBP expression can be discarded and cells that demonstrate high-level SPCBP expression can be harvested and cultured. The expression of multiple SPCBPs can be detected on the same host cell using different fluorescent labels and multidimensional analysis.

For antibodies, there has been described a relative quantitative correlation between levels of cell surface and secreted protein, a feature that has been used for selecting cell line transfectants with improved antibody expression levels (Brezinsky et al., *J. Immunol. Methods* 277:141-55). In one embodiment, SPCBP cell libraries are subjected to FACS sorting after transfected cells such as CHO cells have been cultured in a low-permeability media. The low-permeability media can be Phosphate Buffered Saline (PBS) containing about 40% gelatin with or without fetal calf serum. The low-permeability media reduces diffusion of the secreted proteins into the culture, thereby allowing the secreted proteins to bind to the surface of the CHO cell from which they are expressed rather than diffuse and bind to another cell. The cells are then removed from the low-permeability media and exposed to labeled antibodies that selectively bind a portion of the secreted SPCBPs that is not bound to the surface of the cell. The labeled antibody (which binds the secreted/surface associated SPCBP) can be conjugated with a fluorophore or a metalized label. The cells are sorted based on detection of the labeled antibody, e.g., by using fluorescence-activated cell sorting (FAGS) or magnetic cell sorting, respectively. Using FACS or magnetic cell sorting, the level of SPCBPs secreted and attached to the CHO cell is detected and those cells that secrete high levels of SPCBPs are selected, or those that express SPCPBs in specific relative ratio.

Alternatively, the cells of the library are encapsulated in affinity matrices in gel microdrops. In the first case, the cells are incubated in a matrix that is specific for the secreted product of interest. Secreted products bind to the affinity matrix on the surface of the secreting cell and are subsequently labeled with specific fluorescent reagents for flow cytometric analysis and cell sorting. The matrix itself is created by linking, for example, an avidinylated-specific capture antibody to the previously biotinylated cell surface. The use of a medium of low permeability (as earlier) prevents product cross-feeding (Frykman et al. 1998, *Biotechnol. Bioeng.* 59:214-226 and Holmes and Al-Rubeai, 1999, *J. Immunol. Methods* 230:141-147). In another approach gel, microdroplets are used (as in Gray et al. 1995, *J. Immunol. Methods* 182:155-63). In such systems, the cells of the library are individually encapsulated in agarose beads that contain specific capture reagents. Cells are grown for a short period of time while they produce the SPCBPs and the beads harvested and sorted in a flow cytometer.

Once an optimal ratio is established, the presence of individual binding proteins in this mix may be determined as follows. The identity of the SPCBP is revealed by a binding assay if all of the input SPCBP genes, encoded proteins binding to different targets and the targets are available for testing. Lacking some or all of the targets for the binding assay, the identity is determined by analyzing the presence of the SPCBP genes in the host cell's genome, for example, by Southern blot or by PCR with SPCBP-specific probes and oligonucleotides, respectively. Or, the DNA encoding the SPCBP genes can be retrieved by amplifying with oligonucleotides designed to bind to all SPCBP genes, and the material cloned and sequenced.

In another embodiment, SPCBP-specific reagents are made (see Example 5) and "surrogate" binding tests employed for this analysis. Thus, the invention provides many methods to quickly screen hundreds of mixtures of different protein mixtures.

2.3.5. Purifying Protein Mixtures

Traditionally, before use for human therapy, protein drugs are expressed and purified to homogeneity, consisting of one major molecular species. In some cases, therapy is more efficacious with combinations of proteins or other drugs. This invention describes methods to make a proteinaceous mixture that will contain at least two major molecular species composed of at least two SPCBPs. The large-scale manufacturing of the proteinaceous mixture is a prerequisite for their clinical use and a simple purification procedure is an important feature of the development process. For purifying biopharmaceutical proteins and, in particular, antibodies, research-grade material is often purified by using antigen-affinity chromatography. Since this at industrial scale and for biopharmaceutical production is a not a commercial option and, in particular, for SPCBP mixtures that recognize multiple targets would not be a commercially viable route to therapeutic protein mixtures, it is a preferred embodiment of this invention to use purification methods that are not dependent on the antigen or target that is recognized by the SPCBP component or components. In one embodiment, the genes encoding the components of the two proteinaceous compounds are co-expressed in the same host cell and the different major molecular species that are present in the mixture have a functional binding specificity purified using biochemical/biophysical techniques well known in the art.

In one embodiment, the method is used to make a mixture of a defined number of binding proteins at a selected ratio. In one embodiment, the major molecular species that comprise one or more different binding specificities share a minimal proportion of their encoding genetic information (e.g., an Fc region, a common tag, or another shared domain or feature); such shared feature will provide a common mechanism/assay for following the individual compounds in the mixture. In another embodiment, the major molecular species are preferentially co-purified due to a similar biophysical/biochemical behavior which arise due to a homology between the nucleic acids encoding the various SPCBPs. For example, some chimaeric molecules such as immunoadhesins display a charge dipole due to the different pI of one domain versus the other (Wurm et al. in *Antibody Fusion Proteins*, p. 281; Ed. Wiley, New York, 1999). Such molecules behave non-ideally in separation techniques based on ionic charge. SPCBPs in the mix are preferably related to one another by sequence and preferably are based on the same protein scaffold. Although their binding site will be different, the overall structure, charge distribution and size of such molecules will be highly similar. Therefore, preferably, the SPCBP coding regions have a sequence homology of at least 70%. Further, preferably, SPCBPs in the mix preferably have pI values that do not differ by more than 2 pH units.

The invention also provides biopharmaceutical mixtures produced using this method. Methods for purification of proteins are well known in the art, and include affinity chromatography based on matrices of protein A, protein G, protein L, albumin and other substances, immobilized metal affinity chromatography (IMAC, for Histidine-tagged binding proteins), thiophilic gel-chromatography, preparative gel-filtration, FPLC and HPLC, ion-exchange chromatography etc. In addition, partitioning via aqueous two-phase extraction or chromatography recovery in expanded beds is applicable. Preferably the proteinaceous compounds share physicochemical features, such that they can be co-purified using the same procedures. The reason for this is that, since for therapeutic applications often multiple purification steps are required, a preferred embodiment of the invention is to use binding proteins that have a minimal sequence homology of 70% such that the same physicochemical purification methods can be used to purify all of the binding proteins in the mix. Examples of this are to use binding proteins that all bind generic affinity matrices ligands such as protein A (many human dAbs that contain a human VH segment bind protein A (B. Akerstrom et al. (1994) *J. Immunol. Methods* 177:151-163)), or protein L (for human VL domains (L. J. Holt et al. (2003) *Trends Biotechnol.* 21:484-490)), or albumin (certain affibody-variants), or to use a custom-selected antibody or antibodies or other binding protein or proteins that recognized all of the binding proteins in the mixture. Methods to provide generic binding ligand sites on all members of a library of binding proteins have been described (WO9920749A1).

The sequence homology between the nucleic acids encoding the single polypeptide chains of the binding proteins minimizes the number of purification steps required to obtain the active component of the protein mixture, and provides a means to simultaneously recover the different binding proteins from the same recombinant host cell source. For example single domain binding units such as variable domains derived from Camelids are readily and conveniently produced in lower eukaryotic hosts as described above and in WO94/25591 (Unilever), in production and purification systems tuned toward the particular SPCBP product. If the basis scaffold for a set of SPCBPs is identical the chances are also high that many features of the binding proteins in the mix that are determined by this scaffold will be similar. For example many VHH are extremely heat stable, which allows pasteurization or other heat treatments without loss of antigen binding capacity of mixtures of such VHHs. The higher the percentage of homology between the SPCBPs, the higher the chance that the proteins share similar physico-chemical characteristics and can be co-purified with multiple methods. Preferably the proteins share a homology of 70%, more preferably of 80%, preferably 90%. Preferably the regions within the scaffold of the SPCBP that are not used as permissive site in library construction are 85%, preferably 95% homologous. The percentage of homology is determined either by scoring the differences in the nucleic acid between SPCBP coding regions, or parts thereof, or by empirical methods, for example via hybridization experiments in which one SPCBP coding region or part thereof is used as a probe to determine under set conditions of stringency whether it hybridizes with the other SPCBP coding regions. For this methods in the art have been extensively described.

A simple method of purification is also preferable before carrying out many bioassays. It thus will sometimes be necessary to remove contaminants that interfere with the bioassay, and/or to concentrate the binding proteins in the mixture prior to the assay.

The library and composition screening identifies certain optimal mixtures of SPCBPs associated with a particular expression format and cell lines that produce such optimal mixture. In one embodiment the information that is generated using the methods and compositions of the invention are utilized to develop a cell line or production cell or cell line, for example which produce an equivalent mixture of SPCBPs. In another embodiment SPCBP expressing cells with selected compositions, either as whole cells or as nucleic acid containing fragments thereof, are used to produce a production cell that expresses the SPCBP coding regions. For example cell fusion is used to combine features of the production cell with those of the SPCBP-expressing cell.

3. Applications of Compositions of SPCBP Mixtures

Most experiments to date have been carried out with antibodies, and in particular with monoclonal antibodies. The next section describes applications of mixture of proteins, exemplified by the use of MoAbs, but similarly, mixtures of SPCBPs can be envisaged. For many therapeutic applications the use of binding proteins that recognize different epitopes combined into one molecule has been envisaged. For example molecules targeting two different targets, such as a cancer cell and an effector lymphocyte, are being developed in the field of cancer immunotherapy (R. Repp et al. (2003) *Br. J. Cancer* 89:2234-2243). Single binding proteins have been combined via recombinant technology to provide bispecific reagents, using direct fusion or fusion to multimerization domains. However, particularly recombinantly produced fusion proteins have shown major constrains in their stability, e.g., due to proteolytic degradation and often display reduced expression levels when compared to the individual components. Compared to monoclonal antibodies and interferons for example, their biopharmaceutical development is often a lengthy, more risky and much more difficult process. In addition, it is not always desirable to retain a physical link between the binding sites, and to obtain multiple binding proteins as separate entities not associated with other binding proteins in the mixture. It is our invention to utilize cocktails of separate binding proteins that are produced in the same cell. One application of this invention is to build collections of binding proteins directed to the same target, in which the different binding proteins recognize different epitopes on the target. Another application of this invention is to build collections of binding proteins directed to epitopes on different targets. By way of example we describe examples in which mixtures of antibodies have been used; similarly to antibody mixtures, there are applications for mixtures of different SPCBPs on the same target or antigen, for mixtures of different SPCBPs on different targets or antigens, for mixtures of SPCBPs on different targets or antigens on the same or different target or antigen.

Neutralizing Viruses

Mixtures of anti-viral MoAbs increase the clinical efficacy of the treatment when compared to MoAb therapy. In addition, the probability of emerging viral escape mutants and the likelihood of viral resistance with prolonged therapy are reduced. Antibodies are included that bind to multiple different epitopes or subtypes of the virus. Anti-viral antibodies directed to linear epitopes may be used, that are less prone to the effect of escape mutants than conformation-dependent antibodies. The effect of multiple binding specificities present in the antibody mixture provides a stronger signal for viral clearance than when a MoAb is used.

Mixtures of MoAbs have shown superior effects in the neutralization and elimination of a number of viruses:

Human Immunodeficiency virus (HIV). Infection with HIV-1 will lead to the development of the Acquired Immunodeficiency Syndrome (AIDS) if left untreated. During infection with HIV-1, neutralizing antibodies that are directed against diverse epitopes on the HIV-1 envelope glycoprotein molecules gp41 and gp120 develop. In recent years, a number of human monoclonal anti-HIV antibodies have been isolated and extensively characterized. These MoAbs have been tested independently and in combination in non-human primates for their efficacy in blocking HIV viral transmission. In a clinical trial published in 1992, the administration of HIV-1 seropositive plasma containing high titers of HIV neutralizing antibodies, was associated with a reduction in HIV-1 viremia and a number of opportunistic infections. Several groups have subsequently published that administration of HIV-1 seropositive plasma results in delay of the first AIDS-defining event and improvement of clinical symptoms. However, enthusiasm for passive immunotherapy declined when it was found that antibodies failed to eliminate the virus and resulted in the emergence of neutralization escape variants in patients. It was demonstrated that the antibodies that are induced during natural HIV-1 infection poorly neutralize the virus, resulting in a low potency of hyperimmune sera used for passive immunotherapy of HIV-1 infection. In addition, it was demonstrated that some antibodies that arise during natural infection can even enhance the infection. It was realized that for antibody therapy of HIV-1, potent and well-characterized neutralizing monoclonal antibodies were needed. These early findings spurred the development of human monoclonal antibodies against HIV-1 envelope glycoproteins. In recent years, a number of human monoclonal antibodies against the HIV-1 gp41 and gp120 viral coat glycoproteins have been isolated and characterized for their virus neutralizing activity in vitro. Subsequent experiments in non-human primate models of HIV infection and transmission have shown that human monoclonal antibodies targeting different HIV-1 envelope glycoprotein epitopes exhibit strong synergy when used in combination. It has been suggested that combinations of human anti-HIV monoclonal antibodies can be exploited clinically for passive immunoprophylaxis against HIV-1. These experiments unequivocally demonstrate that mixtures of three to five anti-HIV MoAbs efficiently prevent peri- and postnatal HIV transmission[v].

Rabies virus. Rabies is an acute, neurological disease caused by the infection of the central nervous system with rabies virus. Almost invariably fatal once clinical symptoms appear, rabies virus continues to be an important threat to human and veterinary infection because of the extensive reservoirs in diverse species of wildlife. For passive immunotherapy IgG from pooled serum of rabies immune individuals or immunized horses is used; anti-rabies immunoglobulin is expensive and is either in short supply or non-existent. There is therefore a need for compositions and methods for producing mixes of antibodies, preferably human antibodies, to use in passive immunotherapy of Rabies infections. A mixture of three human MoAbs has been shown to be as effective as polyclonal human anti-rabies Ig in protecting mice against a lethal rabies infection[vi].

Hepatitis B virus. Recombinant HBV vaccines provide a safe and effective means for prevention of HBV conferring long-term immunity through active immunization. In contrast to the slow onset of protection following this vaccination, passive immunotherapy with antibodies to HBV provides immediate but short-term protection against viral transmission and infection. Treatment of chronic hepatitis B infection with anti-viral drugs is characterized by lack of viral clearance, loss of response or emergence of drug-resistant mutants. The importance of neutralizing antibodies in clearing persistent virus infection has been demonstrated and combination treatment of chemotherapeutic drugs and antibodies leads to an additive therapeutic effect. Antibodies are believed to inhibit infection by blocking HBV from entering into cells. Such passive immunotherapy is advisable for individuals who were exposed to HBV-positive material (needle or cut injuries) and for newborns to mothers who are HBV carriers, for patients undergoing liver transplantation. At present such treatment is carried out with Hepatitis B immunoglobulin, a plasma derived, polyclonal antibody preparation obtained from donors who were anti-hepatitis B surface antigen antibody-positive. The availability of this serum is limited and further pricing and safety concerns regarding the use of blood products, make the development of an alternative treatment necessary. A human monoclonal antibody would be advantageous by presenting a stable and reproducible source for prolonged immunotherapy. However, studies show that a monoclonal antibody directed to the S antigen and neutralizing capacity against HBV in chimpanzees delayed but not prevented the infection with HBV. In part this may be caused by the emergence of escape variants, mutants in the S-antigen that can no longer be bound by the monoclonal antibody. Similarly, escape mutants arise in patients after liver transplantation in clinical trials with monoclonal antibodies. Therefore treatment with a single monoclonal antibody may be inefficacious and insufficient. Two human MoAbs against the hepatitis B virus surface antigen were tested in a murine and chimpanzee model of chronic hepatitis B infection (R. Eren et al. (2000) *Hepatology* 32:588-596). Administration of a mixture of these two antibodies into both models resulted in an immediate reduction of viral load. The combination of antibodies worked better in both reducing the viral load and inhibition of liver infection then a commercial polyclonal antibody preparation from pooled human serum. The mixture of two antibodies has been tested in a Phase I clinical trial in patients with chronic HBV infections and shown to be safe and reduce viral load and hepatitis B surface antigen levels (E. Galun (2000) *Hepatology* 35:673-679).

In general for viral diseases, the functional assembly of mixes of anti-viral SPCBPs may increase the clinical efficacy of the treatment when compared to monoclonal therapy, by decreasing the probability of viral escape mutants resistant to treatment, and by reducing the likelihood of viral resistance with prolonged therapy. In the mixture, antibodies can be included that bind to many different epitopes of the virus. It is also feasible to include antibodies to different subtypes of the virus, to broaden the utility of the drug for a wider patient population. Further anti-viral SPCBPs directed to linear epitopes can be added, which are less prone to the effect of escape mutants than conformation-dependent SPCBPs. The effect of multiple binding specificities present in the SPCBP mix can provide a stronger signal for viral clearance than when a monoclonal antibody is used. There are also applications for mixtures of essentially one binding site with different fine-specificities for binding its antigen. For example, when the antigen is prone to mutation as is the case with many viral antigens, in the course of a treatment the epitope on the antigen may be altered such that the binding of a first binding protein is lost. When using a mixture, e.g., based on the same scaffold but with minimal changes from the first and with the similar binding activity but that provide a range of amino acid alterations in the binding site, there is possibility that the mutations will affect the binding of some species in the mixture, but not of others with a different binding chemistry yet similar strength. In such a case it will be preferable to use distinct binding chemistries for the interaction with the antigen, thus the SPCBP should be as unrelated as possible in sequence.

Neutralizing Toxins

Passive immunization has long been established as a valuable prophylactic and therapeutic approach against toxins. In spite of decreasing general acceptance due to the prevalence of infectious diseases among plasma donors, and the inflating safety and efficacy control requirements, imposed on the manufacturers by regulatory authorities, conventional human plasma-derived polyclonal antibody preparations in many cases remain the only products available to the patients.

Tetanus toxin (A. B. Lang et al. (1993) *J. Immunol.* 151: 466-472). A mixture of three human anti-tetanus toxoid MoAbs was shown to act synergistically and gave full protection against the toxin in an animal model. Only 0.7 mg of the human monoclonal antibody mixture gave the same potency as 170 mg of commercially available human polyclonal antiserum used for passive immunization.

Botulinum toxin (A. Nowakowski et. al., *Proc. Natl. Acad. Sci.* 2002, 99, 11346-11350). The botulinum toxins cause the paralytic human disease botulism and are one of the high risk agents for bioterrorism. Three different MoAbs generated against one of the toxins failed to significantly neutralize the toxin as single agents. In contrast, combinations of two MoAbs completed blocked at doses of 20 times the LD50. A combination of three MoAbs neutralized 450,000 50% lethal doses of the toxin in animal experiments: a potency 90 times greater then human hyperimmune globulin. Importantly, it was found that mixing the antibodies caused a large increase in functional binding avidity. These studies show that the potency of the natural polyclonal immune response can be deconvoluted to only three antibodies, suggesting that equally potent activities can be expected from SPCBP mixtures comprising only a limited number of antibodies.

Killing Tumor Cells

Antibody-mediated killing of tumor cells involves a number of different mechanisms. Binding of antibodies to the tumor cell surface may recruit components of the complement system and/or immune effector cells that attack the malignant cells. It is assumed that these killing processes benefit from a high density of antibody molecules on the cell surface. A high density of cell surface-bound antibodies can be achieved by targeting molecules that are up-regulated on the tumor cell surface. In fact, the successful anti-tumor MoAbs Herceptin and Rituximab bind to tumor targets that are highly expressed and it is thought that this is pivotal to their efficacy. A high density of cell surface-bound antibodies can also be achieved by targeting multiple molecules on the tumor cell surface. Individual targets do not need to be highly expressed because multiple targets contribute to the high-density antibody decoration. Thus, tumor targets that have been considered suboptimal for antibody therapy are valuable in the context of mixtures of binding proteins.

Binding of antibodies to the tumor cell surface may also directly exert an effect such as induction of apoptosis (programmed cell death). The processes that govern antibody-induced apoptosis are not fully understood but it has been shown that higher order cross-linking of many different cell surface molecules induces apoptosis. Similarly to some monovalent antibody fragments, some SPCBP mixtures efficiently induce apoptosis.

Breast cancer (C. I. Spiridon et al., *Clin. Can. Res.* 2002, 8:1720-1730). Herceptin™ is a humanized MoAb registered for the treatment of women with breast carcinomas that overexpress the Her-2/neu receptor. In preclinical studies, it has been shown that a mixture of three MoAbs against different epitopes of the Her-2/neu receptor proved more potent than individual MoAbs in preventing tumor outgrowth in animal studies.

Non-Hodgkin's lymphoma (NHL). Rituximab is a chimeric monoclonal antibody that binds to the CD20 molecule overexpressed on B cell tumors including NHL. Recently, Amgen has initiated Phase II clinical trials combining its human anti-CD22 monoclonal antibody epratuzumab with rituximab. Like CD20, CD22 is a cell surface molecule expressed by B cells and B cell tumors. Although the trial is still ongoing, available data show that the combination therapy of the two MoAbs is safe and increases the number of responding patients and complete remissions. These results show that the combination of two MoAbs increases the potency of the anti-tumor treatment as measured with objective clinical endpoints.

Neutralizing Cytokines

The proinflammatory cytokine tumor necrosis factor alpha (TNF-α) is critically involved in the pathogenesis of several chronic inflammatory diseases. MoAbs against TNF-α are currently used for the treatment of rheumatoid arthritis (RA) and Crohn's disease and from both a clinical and commercial point of view belong to the most successful biopharmaceuticals generated by the biotechnology industry.

Interleukin 1 (Il-1) is another cytokine that plays a dominant role in mediating the progression of RA. IL-1 appears to be mostly responsible for cartilage destruction whereas TNF-α is an important mediator of the inflammatory reaction. It has been shown in animal models that blockade of either TNF-α or IL-1 partially controls RA, whereas the combination of anti-TNF-α and anti-IL-1 molecules achieves superior efficacy (U. Feige et al. (2000), *Cell. Mol. Life Sci.* 57:1457-1470). Thus, mixtures of binding sites that simultaneously block TNF-α and IL-1 or other combinations of cytokines may be developed that interfere in two apparently independent pathological pathways in chronic inflammatory diseases such as RA.

Although data are still scarce, it has been shown that combinations of anti-TNF MoAbs synergistically neutralize TNF through complementary effects of competitive and allosteric TNF blocking mechanisms. Thus, cooperative anti-TNF binding proteins present in SPCBP mixtures will most efficient neutralize, resulting in reduced dosing and cost.

Thus, mixtures of SPCBPs are suitable to fight pathogens including viruses like HIV and Rabies, bacteria, fungi and parasites. Other examples where a polyclonal serum or gamma-globulin is currently used that could be replaced with a defined SPCBPs mixture, include such diseases as Rabies, Hepatitis, Varicella-Zoster Virus, Herpes or Rubella. Bacterial diseases that can be treated with SPCBP mixtures include Meningitis, diseases caused by *Staphylococcus, Streptococcus. Hemophilus, Neisseria, Pseudomonas* and the *Actinomycetes*. Targets also include those involved in bacterial sepsis such as lipopolysaccharide (LPS), lipid A, tumor necrosis factor alpha or LPS-binding proteins. Some of these pathogens occur in multiple serotypes and not one but multiple SPCBPs are required to neutralize the various serotypes. A mixture of SPCBPs will provide, by the choice of the binding specificities, a wider coverage of serotypes that are treated and therefore more patients can be treated with the same SPCBP mixture. For this and other reasons, the mixtures can also form suitable diagnostics and part of diagnostic kits for the detection of a disease or disorder in patients.

Mixtures of SPCBPs can be more effective than monoclonal antibodies also in the treatment of ontological diseases such as non-Hodgkin's lymphoma (NHL) and epithelial cell tumors like breast and colon carcinoma. Targeting both CD20 and CD22 on NHL with antibodies has already been proven to be more effective than targeting the tumor cells with the individual antibodies. Suitable target antigens for SPCBPs mixtures in ontological diseases are many, including CD19, CD20, CD22, CD25 (IL-2 receptor), CD33, the IL-4 receptor, EGF-receptor, mutant EGF receptor, Carcino-Embryonic Antigen, Prostate-specific Antigen, ErbB2/HER2, Lewis$^y$ carbohydrate, Mesothelin, Mucin-1, the transferrin receptor, Prostate-specific Membrane Antigen, VEGF and receptors, EpCAM and CTLA-4. In particular, for those antigens which upon targeting by a mixture of SPCBPs can be modulated without necessarily relying on antibody-Fc region mediated effector function, this will be useful. Examples include the efficient blocking of multiple ligand-receptor interactions, or of inter-receptor interactions and pairing such as in the EGFR-family of receptors, or the induction of agonistic effects on receptors, or the induction of apoptosis.

Synergistic effects can be seen when using mixes of SPCBPs that bind different targets and pathways in the disease, such as SPCBPs with anti-angiogenesis and anti-proliferative effects. Applications also exist in this field for a mixture of essentially highly related SPCBPs that all bind to one target epitope but with slightly different binding chemistries which translates into different affinities for binding to antigen. This mix is, e.g., one isolated SPCBP combined with point mutation variants thereof with altered (improved or reduced) affinities. The efficiency of in vivo solid tumor penetration is limited for high-affinity antibodies due to the binding site barrier, yet a minimal affinity is required to achieve a substantial accumulation in the tumor. With the methods described in this document, a mixture of SPCBPs can be established. Such mixtures can be used to increase the accumulation in the tumor, and the best balanced cocktail found by choosing the components and their expression levels. Such mixtures are preferably more active than the individual components, and act synergistically.

Mixtures of SPCBPs are also suitable to neutralize multiple different targets, for example in the field of inflammatory diseases, where multiple factors are involved one way or another in mediating the disease or aggravating its symptoms. Examples of these diseases are rheumatoid arthritis, Crohn's disease, multiple sclerosis, insulin-dependent diabetes, mellitus and psoriasis. Optimal treatment of many of these diseases involves the neutralization or inhibition of circulating pathological agents and/or those on the surface on cells targeted in the specific inflammatory response in the patient. In autoimmunity and inflammatory diseases suitable targets are generally interferons, cytokines, interleukins (IL), chemokines and specific markers on cells of the immune system, and in particular alpha interferon, alpha interferon receptor, gamma interferon, gamma interferon receptor, tumor necrosis factor alpha, tumor necrosis factor receptor, HLA-class II antigen receptor, IL-1 beta, IL-1 beta receptor, IL-6, IL-6 receptor, IL-15, IL-15 receptor, IgE or its receptor, CD4, CD2, and ICAM-1.

Mixtures are also suitable for the neutralization of effects mediated by agents of biological warfare, including toxins such as *Clostridium botulinum* derived botulinum neurotoxin, Anthrax, smallpox, hemorrhagic fever viruses and the plague. The neutralization of the botulinum toxins is discussed here as an example. The botulinum toxins, the most poisonous substances known, cause the paralytic human disease botulism and are one of the high-risk threat agents of bioterrorism. Toxin neutralizing antibody can be used for pre- or post-exposure prophylaxis or for treatment. Small quantities of both equine antitoxin and human botulinum immune globulin exist and are currently used to treat adult and infant botulism. Recombinant monoclonal antibody could provide an unlimited supply of antitoxin free of infectious disease risk and not requiring human donors for plasmapheresis. A panel of human and murine monoclonal antibodies was generated from the B lymphocytes of hyperimmune donors and immunized mice using phage antibody display technology. Single monoclonal antibodies and combinations were tested for their capacity to protect mice from lethal doses of neurotoxin (A. Nowakowski et al. (2002) *PNAS* 99:11346-11350). Whereas single monoclonal antibodies showed no significant protection of the mice against lethal doses of toxin, combinations of only three monoclonal antibodies against different epitopes on the toxin gave very potent protection. The combination of three monoclonal antibodies neutralized 450,000 lethal doses of botulinum toxin, a potency 90 times greater then human hyperimmune globulin. Importantly, the potency of the monoclonal antibody mixture was primarily due to a large increase in functional antibody binding affinity. Thus, methods that allow the cost-effective, controlled and efficient production of mixtures of SPCBPs against botulinum neurotoxin provide a route to the treatment and prevention of botulism and other pathogens and biologic threat agents. As shown in this study, a mix of three antibodies that bound non-overlapping epitopes on botulinum neurotoxin, had a synergistic effect on toxin neutralization due to a increased overall avidity.

Mixtures of binding proteins may be further applied to delay the onset of anti-idiotype responses in patients, by providing multiple idiotypes of an SPCBP family, all binding to the same target, in the simplest form amino acid mutants of the same SPCBP with a resulting similar binding specificity and affinity, to a more complex mixture of multiple SPCBPs directed to the same epitope.

Mixtures of binding proteins can also be applied to develop derivatives of the protein mixtures, including immunotoxins, immunoliposomes, radio-isotope labeled versions, immunoconjugates, antibody-enzyme conjugates for prodrug-therapy (ADEPT), an immunopolymer (Allen (2002) *Nat. Rev. Cancer* 2:750-763). The mixes of the antibodies can either be modified in batch with the appropriate substances, or can be genetically fused to a toxin or enzyme or effector encoding gene as described in the art for monoclonal antibodies.

EXAMPLES

Example 1

Mammalian Expression Vector for Directing the Co-expression of Two Anticalins

A starting point for making a mixture of two SPCBPs by expression from a single mammalian expression vector, is plasmid pRRV (a derivative of VHExpress and described in US 20030224408A1). pRRV (FIG. 7B) is a plasmid that is used for the expression of antibodies in the IgG format, by co-expression of light and heavy chains under control of a single CMV promoter and the two coding regions separated by an IRES sequence. The plasmid contains a series of unique restriction sites for cloning of SPCBP genes.

Two SPCBP genes are cloned by directional cloning of the coding regions into the ApaLI & AscI and BssHII & BclI restriction sites of pRRV. As an example the cloning of two anticalins is described, but equally well other SPCBPs can be cloned with the same procedure. If internal sites for the restriction enzymes are found in the SPCBP gene of interest, they can be swiftly removed by site-directed mutagenesis. The two anticalins are the following:

AC-1: Engineered Lipocalin. Flua, an anti-fluorescein anticalin, selected from an engineered lipocalin library and the structure of which in complex with antigen was solved (pdb number 1N0S) (I. P. Korndorfer et al. (2003) *Proteins* 53:121-129).

AC-2: DigA16 is an artificial digoxigenin-binding protein, which was derived from the bilin-binding protein, a lipocalin of *Pieris brassicae*, via reshaping of its natural ligand pocket.

The crystal structures of DigA16 in the presence of either digoxigenin or digitoxigenin and for the apo-protein was determined at 1.9 A resolution (I. P. Korndorfer et al. (2003) *J. Mol. Biol.* 330:385-396). PCR reactions are carried out with the template AC-1 and AC-2 genes, for 25 cycles, denaturation at 94° C. for 30 seconds, annealing at 50° C. for 60 seconds, and elongation at 72° C. for 90 seconds, using Taq DNA polymerase (Promega, Madison, Wis.) with primers that are designed to anneal to 5' and 3' coding regions, with the latter providing also a stop codon after the last codon to be translated. These primers also incorporate the restriction enzyme sites that were just cited at both ends, and at the 5' end of the genes in such manner that the reading frame is maintained upon directional cloning of the genes into pRRV (as indicated on FIG. 7A). The resulting AC-1 product is purified, digested with the restriction enzymes ApaLI and AscI, and cloned into pRRV, resulting in p2-I-AC-1. The two AC-2 coding region is then amplified from its template for cloning as a BssHII-XbaI fragment. In the oligonucleotides used for the PCR both poly-His tags and a stop codon is provided following the AC-coding regions and prior to the AscI and XbaI positions to ensure that the AC-1 and Ac-2 coding region are correctly translated as soluble, separate products and can be detected with polyHis antibodies. The two genes are cloned stepwise into the vector, to yield first vector p2-I-AC1 and then vector p2-I-AC1xAC2. The integrity of the sequences is confirmed by using the AmpliTaqs cycle sequencing kit (Perkin-Elmer, Foster City, US) with specific primers based in the vector backbone just adjacent to the anticalin encoding inserts; the DNA sequences of the insert are checked to maintain the correct sequences of the anticalin coding regions and the junctions with the expression plasmid.

Example 2

Expression Vectors for the Co-expression of Three Camelid VHH Proteins

In this example, the expression vectors for simultaneous expression of three binding proteins derived from a dromedary/camel heavy chain only antibodies and all having specificity for lysozyme of different species is described.

cAb-1. Antibody cAb-Lys3 is a "VHH" that inhibits hen egg-white lysozyme and its structure in complex with antigen was determined by crystallography (A. Desmyter et al. (1996) *Nat. Struct. Biol.* 3:803-811; T. R. Transue et al. (1998) *Proteins* 32:515-522).

cAb-2. The second antibody is cAb-TEM02 described in K. Conrath et al. (2001) *J. Biol. Chem.* 276:7346-7350.

cAb-3. The third binding protein is a VHH antibody, clone cAb-HuL6, a fragment derived from a dromedary "heavy chain" antibody with high specificity for native human lysozyme and its amyloidogenic variants (M. Dumoulin et al. (2002) *Protein Sci.* 11:500-515). The protein was shown to inhibit the formation of amyloid fibrils by human lysozyme (M. Dumoulin et al. (2003) *Nature* 424:783-788). It has a $k_a$ value for lysozyme of 8.6 ×$10^5$ $M^{-1}s^{-1}$ and a kd of $5.9\times10^{-4}s^{-1}$. Its amino acid sequence is QVQLQESGGGS-VQAGGSLRLSCSASGYTYISGW-FRQAPGKEREGVAAIRSSDGTTYYAD SVKGRFT-ISQDNAKNTVYLQMNSLKPEDTAMYYCAATEVAGW PLDIGIYDYWGQGTEV TVSS (SEQ ID NO:8). Further its structure in complex with lysozyme was determined (structure name in pdb is 1OP9).

Figure 7A:
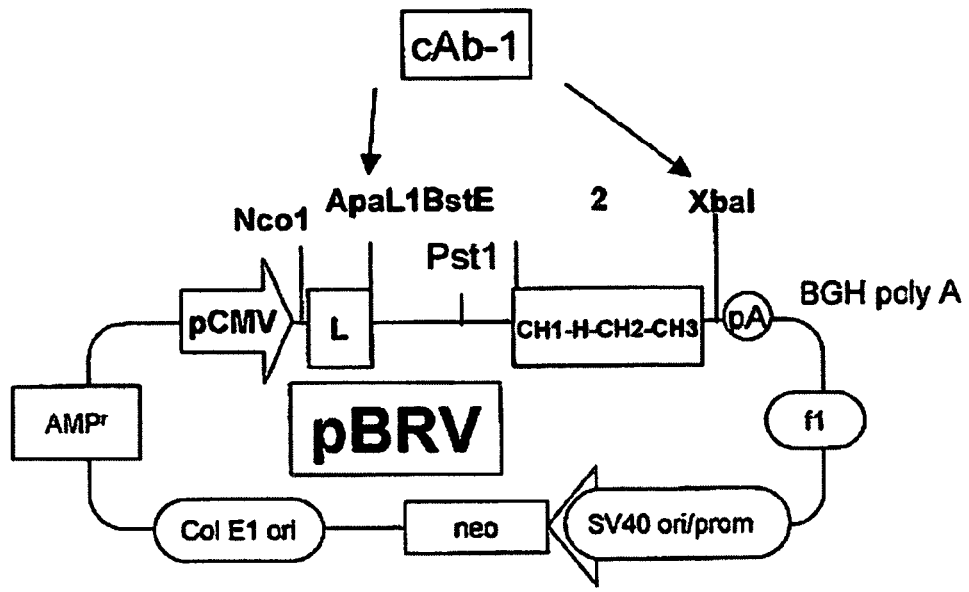
FIG. 7A pBRV.
Figure 7B:
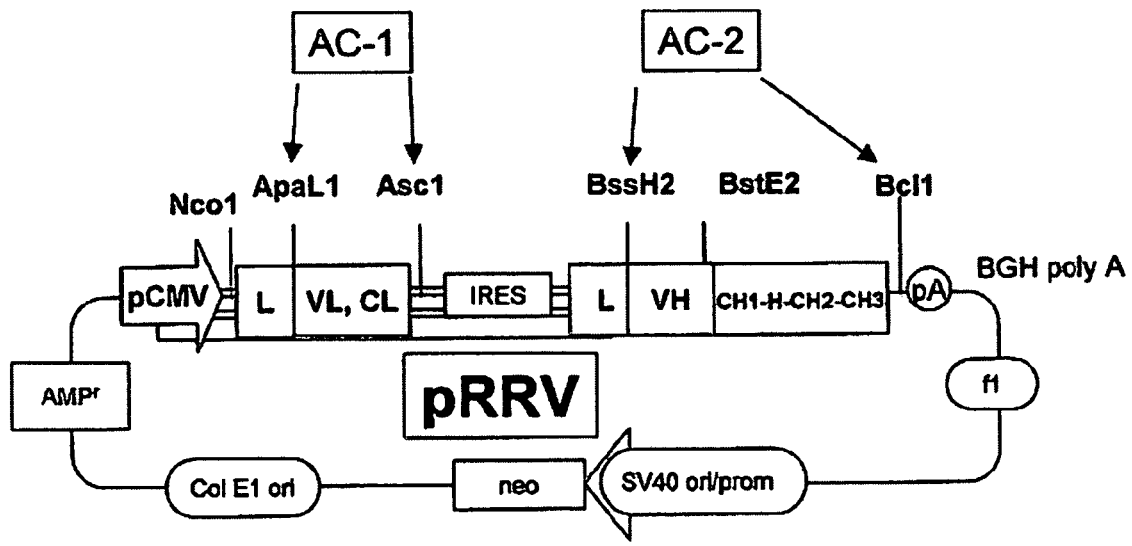
FIG. 7B pRRV, FIG. C pABExpress40; cloning sites for directional insertion of domain antibodies and anticalins are indicated (see text for further details).

The first starting point for expressing of these three cAbs in a mammalian cell as secreted proteins is plasmid pBRV, a derivative of VHExpress described in US 20030224408A1 (schematically depicted in FIG. 7A). Mixtures of these plasmids are be used to build libraries (as in FIG. 2, Panel A). The cloning is done for pBRV with cAb-coding regions being amplified while appending ApaLI and XbaI sites at the 5' end 3' end of the gene, respectively. The 3'-based primer also introduces a polyHis-tag. This is carried out for cAb-1, yielding plasmid p1-cAb-1. This plasmid directs the expression of the soluble cAb1 fragment which carries a poly-His-tag that is recognized by several monoclonal antibodies of commercial source as well as can be used for IMAC purification.

Figure 7C:
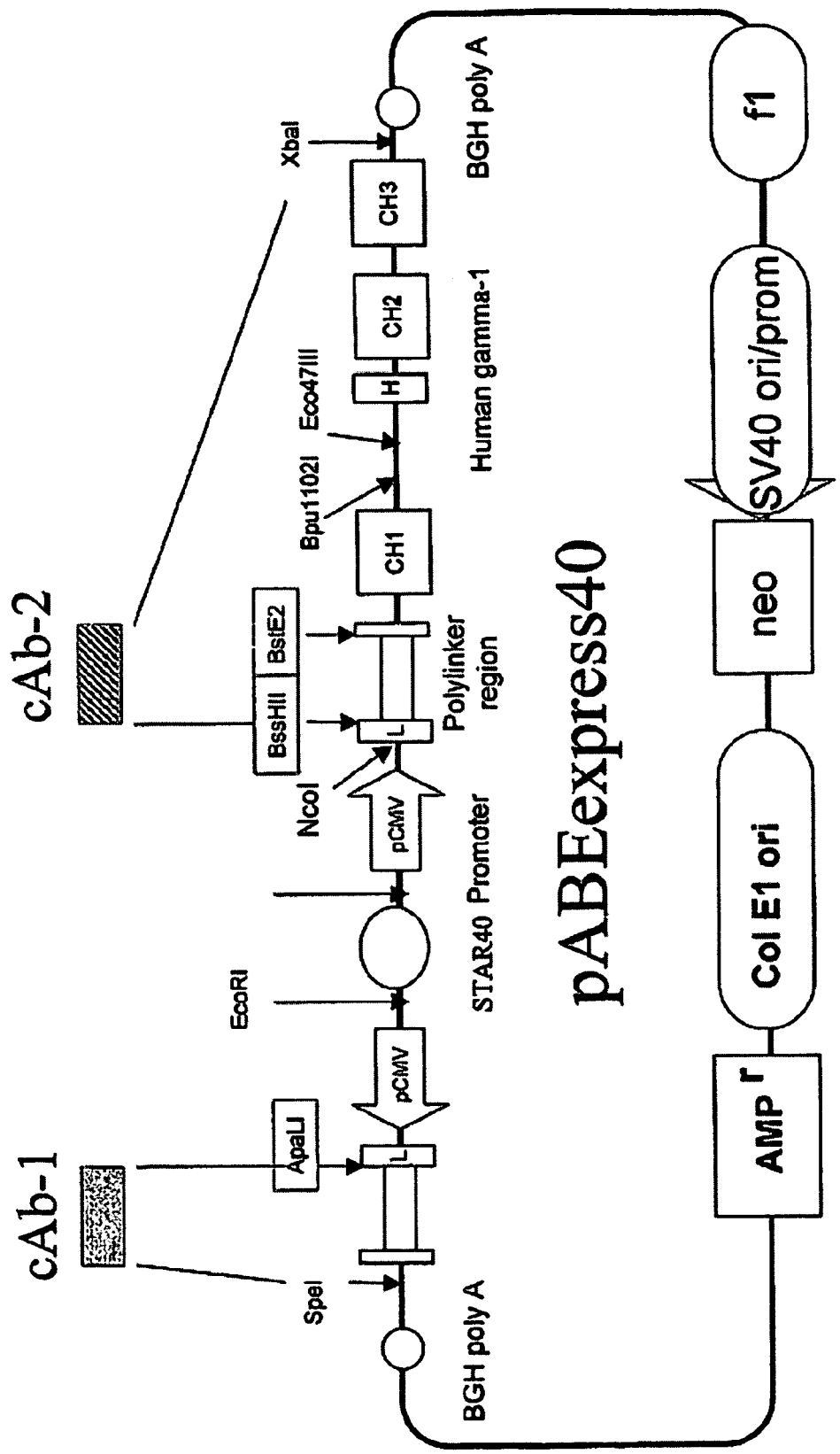
FIG. 7: Plasmids for expression of multiple SPCBPs in mammalian cells.

The other two cAb genes are cloned into a vector that will direct non-IRES-linked expression of the two coding regions. In addition, a STAR element is introduced. STAR elements confer high level and stable expression of proteins in mammalian cells in a copy number-dependent fashion (Kwaks et. al. (2003), *Nat. Biotechnol.* 21:553-558). The vector used for this, pABExpress40, is described in European patent application no. 03076671.1 and depicted in FIG. 7C. pABExpress40 contains both heavy and light chain cassettes with their respective transcriptional orientation in opposite directions, and the anti-repressor element positioned in the middle of the two transcription units. This plasmid, pABExpress40 is used first in the cloning of the first chosen binding protein gene, cAb-2 (using ApaLI and SpeI cloning sites which are appended to the coding region of the cAb-2 gene using oligonucleotides designed for directional cloning and maintaining in the resulting construct the reading frame in the binding protein's gene following the vector's leader sequence), resulting in pABExpress40-cAb-2. This plasmid is used to receive the second binding protein encoding gene, cAb-3 (as BssHII-XbaI fragment) (all of these four sites are unique in pABExpress40; generally, if restriction enzyme recognition sites are endogenous to the binding protein encoding gene, it can either be first removed by site-directed in vitro mutagenesis, or the PCR product can be subjected to a partial digest with this enzyme (and a full digest with the other enzyme), then the full-length material is gel-purified and this fragment cloned; in addition other unique restriction sites equivalent in their use for this cloning experiment are available in the vector, see Table 5 in Persic et al., *Gene* (1997) 187:9-18). In the PCR reaction, the 3'-based oligonucleotide also incorporates a stretch of six histidines followed by a stop codon, such that the proteins can be purified by IMAC as described earlier. After sequential cloning of the two binding protein genes, cAb-2 and cAb-3, the plasmid that contains both VHH genes is designated p2-ST-cAb2/3, is identified by restriction analysis and sequencing, and its DNA prepared for transfection experiments.

For constructing a library of cells expressing three different binding proteins, alternatively a tricistronic vector can be built. Such vectors were described for other applications and utilize different IRES sequences and cloning sites. In order to speed up the cloning of multiple SPCBP genes, it is important to provide in such vector unique restriction enzyme sites bordering the SPCBP coding regions, such that three different genes can be readily cloned into such vector, sequentially in two steps or faster via three-way ligation. A tricistronic retroviral and adenovirus vectors co-expressing IL-12 (IL-12p40 plus IL-12p35) and CD80 were described by utilizing two internal ribosome entry site (IRES) sequences to link the three cDNAs. A murine stem cell virus (MSCV)-based retroviral vector (MSCV-hIL12.B7) utilized distinct IRES sequences from the encephalomyocarditis virus (EMCV) and the foot-and-mouth disease virus (FMCV), whereas Ad5-based adenovirus vectors contained transcriptional units with two EMCV IRES sequences under the control of murine (AdMh12.B7) or human (AdHh12.B7) cytomegalovirus promoters. By combining different promoter and IRES sequences such as the ones listed here and earlier in the text, plasmids that can mediate the expression of three SPCBPs can be built.

Example 3

Production of a Library of Cells Expression Two and Three Different Cabs in Different Ratios Plasmids p1-cAb1 and p2-ST-cAb2/3 are used for making multiple stable transfectants. Plasmid p2-ST-cAb2/3 is transfected alone or in combination with plasmid p1-cAb1. By selection using the neo-resistance gene and culturing and screening methods known to those in the art, stable PER.C6 derived cell lines expressing the two or three cAb-s and in different ratios are obtained. Essentially $5 \times 10^6$ PER.C6™ cells are transfected using Lipofectamine according to the manufacturer's instructions, and 3 micrograms of DNA of the plasmid (or 2+1 microgram if the two are used together). After five hours, the cells are washed and the medium is exchanged with non-selective medium. The next day the medium is replaced with fresh medium containing 500 microgram/ml G418 (Sigma-Aldrich) and also every next two to three days the culture medium is refreshed until clones appear (15 to 20 days after seeding). Clones are picked and cloned out to limiting dilution conditions, such that two to three weeks later clonal cell lines start appearing. These are expanded to larger wells and flasks, and eventually the selective medium is omitted. The first analysis of the cell lines is to analyze the presence of the two or three different cAb-genes in the cell lines created, by amplifying the genomic DNA of these cell lines with specific (vector and coding region-based) oligonucleotides for cAb-1 and cAb-2 and cAb-3, and confirming the presence by sequencing the amplified material. The copy number of the expression cassettes (putatively the same for both cAb-1 and cAb-2) is determined by Southern blot or Fluorescent In Situ Hybridization (FISH). The supernatant of these cell lines is harvested for analysis of the secreted cAb-mixtures. The cAb proteins are purified from the supernatant by IMAC according to the manufacturer's instructions. cAb-mixtures are isolated, purified and tested in a series of assays. Secondly, the mixture is biochemically characterized using SDS-PAGE and Western blot (for unpurified supernatant) and using SDS-PAGE and iso-electric focusing with IMAC-purified proteins. Thirdly, lysozyme binding and lysozyme neutralization assays are carried out, by ELISA assay as described above and catalytic assay for lysozyme. Since the cAbs bind to different species of lysozyme, the presence of the multiple binding proteins in the mix is also detected using lysozyme from different species including from hen egg-white and from humans. Relative intensities of the signals, on gels or in ELISA reveal differential relative ratios of the cAbs in different cell lines.

Example 4

Production of Libraries of CHO Cells Producing Various Protein Mixtures

Plasmids p2-I-AC1×AC2 (Example 1) and p1-cAb-1 (Example 2) are used in a 2:1 co-transfection experiment of CHO.K1 cells essentially as described for PER.C6 cells (Example 3). Stably transfected cell lines are generated by selecting cells on G418 and the supernatant of clones obtained in limiting dilution tested for the presence of the anticalins or the cAb by solid-phase ELISA using the three different antigens, Digoxigenin, Fluorescein and lysozyme as coated antigens. Relative intensities of in ELISA reveal differential relative ratios of the ACs and cAb in different cell lines.

Example 5

Detailed Analysis of Mixtures of Binding Proteins Using ELISA and the Use of Binding-site-specific Reagents The three cAbs of example 3 and the mix of anticalins and one cAb are analyzed in more detail as follows. The culturing of individual cell clones expressing a mixture is expanded and the binding protein fragments isolated via their Histidine tags using IMAC. The resulting protein mixtures are analyzed as follows.

First instance we consider the case of a mixture composed of multiple binding proteins each directed to different epitopes but all present on the same target antigen (the mix of cAb1, 2 and 3). The following methods are available for analyzing the mixture. The binding site region on each binding protein will yield different amino acid compositions and allows the following, antigen-independent, analysis:

(1) Size-based gel electrophoresis such as SDS-PAGE: for relative small sized binding proteins such as cited in Example 1, the differences in molecular weight caused by the unique amino acid composition in or near the binding site may be revealed by gel electrophoresis. By using high-resolution methods (for example gels with gradients), small differences in molecular weight results in a change in mobility and thus the presence of the individual binding proteins in the mixture revealed.

(2) Isoelectric focusing gel analysis: this analysis relies on a different pI value for the different binding proteins. Each molecule will display a unique iso-electric point. Proteins with a different pI are separated via electrophoresis in a pH gradient. The method is semi-quantitative. If two binding proteins in the mixture have only a minimal difference in their pI value, it will be difficult to separate them using this test, and the other tests cited are used.

(3) Mass-Spectrometry analysis: this analysis relies on the differential amino acid composition (or other changes that alter the molecular weight and/or composition) of the binding proteins, which, after digestion with proteolytic enzymes, yields a unique spectrum of peptides in MassSpec analysis. This method is predominantly qualitative, but can be combined with other analytic methods.

(4) Binding analysis based on "anti-idiotype" antibodies: this analysis requires the availability of reagents that specifically recognize one binding protein binding site in the presence of the other binding sites in the mixture. Suitable for this analysis are "anti-idiotype" antibodies, antibodies which uniquely recognize the area on the binding protein that is equivalent to the idiotype of and antibody. Since the binding proteins are different in amino acids sequence, they will also have other "idiotypes" and thus reagents can be obtained that recognize them. In the example with anticallins, the binding proteins share a high level of sequence homology and thus the unique features of the idiotype are formed mainly by the regions that were originally diversified. Anti-idiotype antibodies are selected using the individual binding protein as antigen in a selection of a large phage displayed binding protein library using methods known to those in the art. Typically used are a non-immune antibody library (H. J. de Haard et al. (1999) *J. Biol. Chem.* 274:18218-18230), which yields Fab fragments, and a semi-synthetic scFv phage antibody library (de Kruif et al. (1995) *J. Mol. Biol.* 248:97). Anti-idiotype antibodies are selected on immobilized or biotinylated AC-1 and AC-2 binding proteins from the cited non-immune binding protein library, Using ELISA screening of the selected phage antibodies on these two proteins used for the selection, anti-idiotype antibodies that uniquely recognize the "idiotype" of one of the two binding proteins are identified. The respective Fab and scFv reagents selected from these libraries are expressed as antibody fragments and purified using standard methods, for example, described in these citations and in *Antibody Engineering* (2001), Eds. Konterman and Dubel, Springer Lab Manual). The fragments are used in ELISA to determine which idiotype is present in the binding protein mixture, which is carried out in a quantitative assay. The anti-idiotype antibodies specific for the binding sites of AC-1 and AC-2 are also used in antigen competition experiments with the preparation made in Example 4, to delineate the contribution of an individual binding site to the biological activity of the binding protein mixture.

(5) Binding analysis based on binding-protein binding peptides: Alternatively, the individual binding proteins are used to derive idiotype-associated peptides, linear or conformational peptides derived from the sequence of the antigen and still reactive with the binding protein, for example via PepScan analysis, as was demonstrated for the rabies virus neutralizing antibody MAb 6-15C4 (van der Heijden et al. (1993), *J. Gen. Virol.* 74:1539-45). An alternative is to isolate peptide mimotopes, with sequences unrelated to the original antigen yet specifically binding to the sequences associate with the binding site of the binding protein. Provided the reaction is specific for a given binding protein in the context of the other or others in the mixture, such peptides are also suitable for a specific analysis of the binding protein mixture. Peptides with such unique reactivity to a given binding protein are selected from phage display peptide libraries using methods essentially similar to those for phage binding protein libraries. The binding test with the anti-idiotype antibodies and peptide-mimotopes is qualitatively or quantitatively, and a large series of binding tests are feasible, including ELISA, RIA, Flow cytometric analysis, BIAcore etc.

Also disclosed is the analysis of a mixture comprising multiple binding proteins in which each of the original binding proteins binds to a different antigen (as in the mixes generation in Example 4). This resembles the situation in which the binding proteins recognize the same antigen or target, and anti-idiotype reagents or peptide mimics are available. The analysis of multiple specificities in a mixture is carried out as follows (while keeping in mind that antigen is synonymous for anti-idiotype). The reactivity to individual antigens is tested in ELISA on all antigens separately, with standardized assays using the monoclonal antibodies and quantitative IgG ELISA test. Antigen is coated directly or indirectly, the plates incubated with the binding protein mixture, and bound binding protein detected with a reagent that recognizes all of the binding proteins. For example anti-tag antibodies are particularly useful for this, or reagents that recognize the region within the binding proteins that is shared between them due to the level of identify between the proteins. This leads to a "specific" activity of the preparation, that is a reactivity in relative units of activity per binding protein quantity.

Example 6

A Mix of Three VHH Domains Expressed in One *E. Coli* Host Cell

Figure 9:
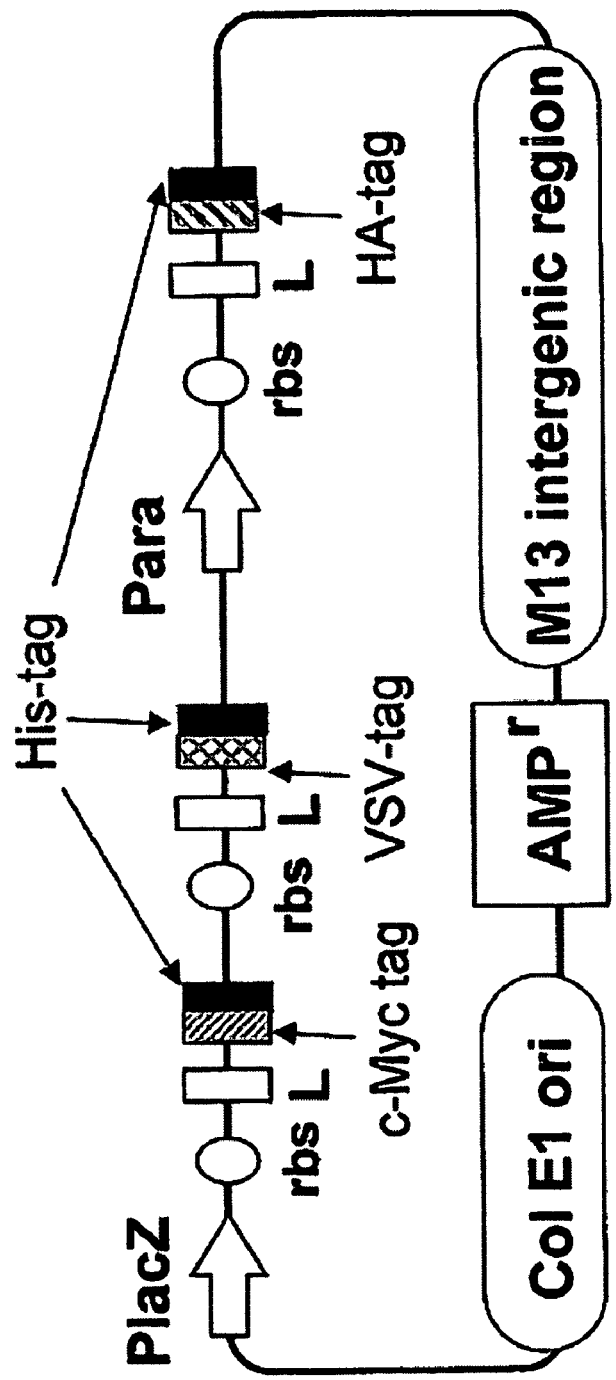

The three cAb-genes, cAb-1, 2 and 3 are cloned into a prokaryotic expression vector, using cloning methods as before. First the coding region genes are amplified with oligonucleotides that hybridize to the 5' and 3' ends of the nucleotide sequences and provide appropriate restriction enzyme sites for cloning. Standard cloning techniques are described in Sambrook et al., *Molecular cloning*, second edition, Cold Spring Harbor Laboratory Press (1987). CAb genes are amplified by the polymerase chain reaction using methods well known in the art. The receptor plasmid is pSCFV-3 which was described in European patent application no. 03076671.1, and contains three sites for insertion of the cAb coding regions (FIG. 9). pSCFV-3 carries unique restriction sites for cloning cAb genes, two behind the same lacZ promoter and separated via a new ribosome-binding site (rbs) and signal sequence (L), and one behind an arabinose-inducible promoter, rbs and L. It also carries different tags, one for each of the cAb cassettes, c-myc (sequence EQKLISEEDL (SEQ ID NO:9)), the VSV-tag (sequence YTDIEMNRLGK (SEQ ID NO:10)) and the influenza Hemagglutinin (HA)-tag (sequence YPYDVPDYA (SEQ ID NO:11)), and all followed by a stretch of three Ala and five His. This setup provides a method for detection of the individual antibodies in the mix, and a generic method for purification, based on immobilized metal affinity chromatography (IMAC) using methods well known in the art. All three cAb coding regions are sequentially cloned into this plasmid, downstream of a bacterial leader sequence, and in frame with the tag sequence.

The expression of the mix of cAbs is done as follows. Soluble cAb fragments are expressed upon induction with isopropyl-$\beta$-D-thiogalactopyranoside (IPTG) from the lacZ promoter that drives the expression of the cAb in pSCFV-based plasmids and with and without the arabinose promoter inducer, and the cAb protein mixtures harvested from the periplasmic space of *E. coli* TG1 cells. To confirm binding of the individual cAbs, an ELISAs is performed using Polysorb plates (Nunc) coated with hen-egg white and human lysozyme. By induction with IPTG, the expression of a mixture of two functional cAb fragments is achieved. By further induction with arabinose, an additional cAb fragment is co-expressed. The contribution to the binding in the mix of each of the cAb fragments is confirmed using one of three anti-tag antibodies (the mouse monoclonal antibody 9E10 binding to human c-Myc epitope tag (product code from abcam, www.abcam.com: ab32), and polyclonal antibodies to the HA-tag (ab3413) or VSV-tag (ab3556). To verify whether the production is carried out by one bacterium and its progeny and not by three clones that each produce one of the antibody fragments, the culture is colony-purified after four hours in the induction phase and the production tested of three independent clones, confirming that the expression is clonal.

For detailed analysis, the cAb mixture is purified and concentrated. To determine the percentage of cAbs correctly, the cAb mixture is first purified from the *E. coli* periplasmic extract using IMAC. Briefly, an IPTG and arabinose induced 500 ml culture (kept for 4 hours at 30° C.), is spun at 4600×g for 20 minutes at 4° C., and the bacterial pellet resuspended in phosphate buffered saline (PBS) containing protease inhibitors (phenyl-methyl-sulfonyl fluoride and benzamidin). The solution is sonicated at 24° C. using an ultrasonic desintegrator (MSE Scientific Instruments), and the suspension centrifuged at 50,000×g for 30 minutes at 4° C. The supernatant fraction is incubated with TALON™ resin according to the instructions of the manufacturer (Clontech). After extensive washing, proteins are eluted using 100 mM imidazole. Afterwards, cAb fragments are further purified by gel filtration using a Superdex 75 column (Amersham Pharmacia Biotech) connected to a Biologic instrument (Biorad). CAb concentrations are quantitated using the bicinchoninic acid kit (Pierce).

Alternatively to the use of one plasmid, the three cAb expression cassettes can also be cloned in separate plasmids, for example into compatible plasmids such as pBR322 and pACYC and maintained in the same host cell before induction.

Example 7

Isolation of Single-domain Antibodies Against a RABIES GLYCoprotein from a VL Phage Library, Production of a Library of Cells Expressing Multiple VLs and Screening the Mixtures for the Most Optimal Neutralization Mixture Rabies-specific single domain VL antibody fragments are selected from a phage displayed repertoire isolated from human PBLs and diversified by DNA-shuffling, as described in van den Beucken et al. (2001), *J. Mol. Biol.* 591-601 (libraries B and C). Phage particles are made from cultures of these two libraries. The rescue of phagemid particles with helper phage M13-KO7 is performed according to (Marks et al. (1991), *J. Mol. Biol.* 222:581-597) on a 1-L scale, using representative numbers of bacteria from the library for inoculation, to ensure the presence of at least ten bacteria from each clone in the start inoculum. For selection of VLs, rabies G-protein is used. Virus purification and glycoprotein purification have been described elsewhere (Dietzschold et al. (1996) *Laboratory Techniques in Rabies*, Eds. Meslin, Kaplan and Korpowski, World Health Organization, Geneva, p. 175). For selections, $10^{13}$ cfus (colony forming units) are used with 10 microgram/ml Rabies glycoprotein coated in immunotubes (Maxisorp tubes, Nunc) or with 250 nM soluble biotinylated G protein. Antigen is biotinylated at a ratio of one to five molecules NHS-Biotin (Pierce) per molecule antigen according to the supplier's recommendations. Three rounds of selection are carried out with these libraries. Detailed protocols for culturing and selecting phage display libraries have been described elsewhere (as in Marks et al. (1991), *J. Mol. Biol.* 222:581-597) and are well known to those working in the art. Briefly, the selection with the biotinylated antigen is carried out as follows. Phage particles are incubated on a rotator wheel for one hour in 2% M-PBST (PBS supplied with 2% skimmed milk powder and 0.1% Tween-20). Meanwhile, 100 microliters Streptavidin-conjugated paramagnetic beads (Dynal, Oslo, Norway) are incubated on a rotator wheel for two hours in 2% M-PBST. Biotinylated antigen is added to the pre-incubated phage and incubated on a rotator wheel for 30 minutes.

Next, beads are added and the mixture is left on the rotator wheel for 15 minutes. After 14 washes with 2% M-PBST and one wash with PBS, phage particles are eluted with 950 μM triethylamine for five minutes. The eluate is immediately neutralized by the addition of 0.5 ml Tris-HCl (pH 7.5) and is used for infection of log-phase *E. coli* TG1 cells. The TG1 cells are infected for 30 minutes at 37° C. and are plated on 2×TY (16 g Bacto-trypton, 10 g Yeast-extract and 5 g NaCl per liter) agar plates, containing 2% glucose and 100 μg/ml ampicillin. After overnight incubation at 30° C., the colonies are scraped from the plates and used for phage rescue as described (Marks et al. (1991), *J. Mol. Biol.* 222:581-597). Culture supernatants of individually selected clones harboring either rescued phage or soluble VL fragments are tested in ELISA with directly coated antigen or indirectly captured biotinylated antigen via immobilized biotinylated BSA-streptavidin. Here described is the procedure with biotinylated antigen for the detection of soluble VL fragments. For capture of biotinylated Rabies glycoprotein, first biotinylated BSA is coated at 2 μg/ml in PBS during one hour at 37° C. After three washes with PBS-0.1% (v/v) Tween 20 (PBST), plates are incubated during one hour with streptavidin (10 μg/ml in PBS/0.5% gelatin) (24). Following washing as above, biotinylated antigen is added for an overnight incubation at 4° C. at a concentration of 3 μg/ml. The plates are blocked during 30 minutes at room temperature with 2% (w/v) semi-skimmed milk powder (Marvel) in PBS. The culture supernatant is transferred to these wells and diluted one- or five-fold in 2% (w/v) Marvel/PBS and incubated for two hours; bound VL is detected with anti-myc antibody 9E10 (5 μg/ml) recognizing the myc-peptide tag at the carboxyterminus of the VL1 chain, and rabbit anti-mouse-HRP conjugate (DAKO). Following the last incubation, staining is performed with tetramethylbenzidine (TMB) and $H_2O_2$ as substrate and stopped by adding half a volume of 2 N $H_2SO_4$; the optical density is measured at 450 nm. Clones giving a positive signal in ELISA (over 2× the background), are further analyzed by sequencing. It would be a lot of work to purify each individual reactive VL clone and test them individually for virus neutralization. Instead, five antigen-reactive VLs that are also reactive with protein L (L. J. Holt et al. (2003) *Trends Biotechnol.* 21:484-490) are identified, and are picked for directly making mixtures using the methods of the previous examples, and the neutralization behavior of the mixes tested. Protein L purification makes the provision of tags obsolete and provides a generic purification scheme for all selected VLs.

Example 8

A Library of CHO Cells Expressing a Mixture of Parasite-Neutralizing SPCBPs

The single polypeptide chain binding proteins used in this experiment are five camelid antibody fragments described to bind the variant-specific surface glycoprotein (VSG) dimer of the African trypanosomes (B. Stijlemans et al. (2004) *J. Biol. Chem.* 279:1256-1261). The five antibody fragments were selected from a phage display library of $5 \times 10^7$ different lymphocytes of immunized dromedary by panning on purified VSG. Of the five protein, there is one, cAb-An33, which binds to a conserved epitope on the surface exposed Asn-linked carbohydrate present on VSG (B. Stijlemans et al. (2004) *J. Biol. Chem.* 279:1256-1261). This small antibody fragment, unlike larger lectins or conventional antibody fragments, is able to penetrate variant surface glycoproteins (VSG) which are common to multiple VSG classes.

The clones with original names cAb-An02, cAb-An33, cAb-An04, cAb-An05 and cAb-An06 are taken for creating a mixture of cells that express different levels these SPCBPs. The sequences of these SPCBPs are described at GenBank™ accession numbers AY263486, AY263490, AY263487, AY263488 and AY263489, respectively.

The cAb coding regions are amplified from their template by oligonucleotides that bind to the equivalent regions in the DNA encoding N- and C-terminal regions for these SPCBPs. For cAb-AN33, the plasmid containing the cAb-An33 gene as obtained after the pannings (B. Stijlemans et al. (2004) *J. Biol. Chem.* 279:1256-1261) is used as template in a PCR reaction with primers

```
SEQ ID NO:1:
5'-AGTGTACAGG CGCGCACTCC GATGTGCAGCTGGTGGAGTC-3'
and
```

SEQ ID NO:2:
5'-TGAGGAGAC<u>G GTGACC</u>TGGG TCCC-3'.

This amplifies the VHH coding region and in one primer appends a restriction site (in this case BssHII) for cloning, in this case outside of the coding region itself, and relies on the natural unique restriction site in the other (BstEII). The design of the primers for these and the other primers for cloning is done such that the reading frame is maintained with the preceding eukaryotic leader sequence, and the following tag encoding sequence.

Three cAbs, cAb-An02/33 and 04 are cloned in several steps into one plasmid that will mediate the expression of three SPCBPs. First cAb-An33 is amplified and cloned into pAbExpress as BssHII-BstEII fragment into pABExpress40 (FIG. 7C), to yield pAn33. Secondly a PCR fragment is prepared from pRRV, to amplify the IRES sequence in this plasmid while appending at the 5' end a BstEII site, followed with a sequence encoding the 3' end of the An33 coding region, followed with the sequence encoding the myc-tag, as used in many phage display vectors such as pHEN1 (Hoogenboom et al., *Nucl. Acids Res.* 1991), a "taa" stop codon, followed by 35 nucleotides the 5' annealing sequence of the IRES element (this all with one primer, which will start as follows:

SEQ ID NO:3: 5'-GATAAATCTG GTCACCGTCT CCTCAGAACAAAAACTCATCTCAGAAGAGGAT <u>CTGAAT TAATAA</u>- . . . (myc-tag encoding region underlined, this sequence followed by the IRES-based 35 nucleotides).

The 3' primer for the IRES amplification is based in the human constant region CH1 domain. This amplification yields an IRES containing PCR fragment that is cut with BstEII and BssHII. This fragment is ligated together with a BssHII-XbaI-digested PCR fragment that itself is made by amplification of the cAb-An04 template with the following two primers:

SEQ ID NO:4: 5'-AGTGTACAGGGCGCGCACTCC CAGGTGCAGC TGGTGGAGTC-3', and

SEQ ID NO:5: 5'-ATACGCTCTAGATTAGCTGG AGACGGTGAC CTGGGTCC<u>CC GG</u>-3' (restriction sites are underlined).

These two DNA fragments are ligated into BstEII-XbaI digested pAn33 in a three-way ligation step. Clones that have inserted both the IRES and cAb-An04 are identified and the clone after sequence confirmation designated pAn33×04. Finally cAb-An02 is amplified from its template with two primers that append an ApaLI site at the 5' end and a stop codon and AscI restriction site at the 3' end with primers:

SEQ ID NO:6:
5'-GCATTATCTG GC<u>GTGCAC</u>TC TGATGTGCAGCTGGTGGAGTC-3'
and with

SEQ ID NO:7:
5'-TACAGATAT<u>G GCGCGCC</u>TTA TGAGGAGACGGTGACCTGGG

TCCCCT-3'.

Figure 8:
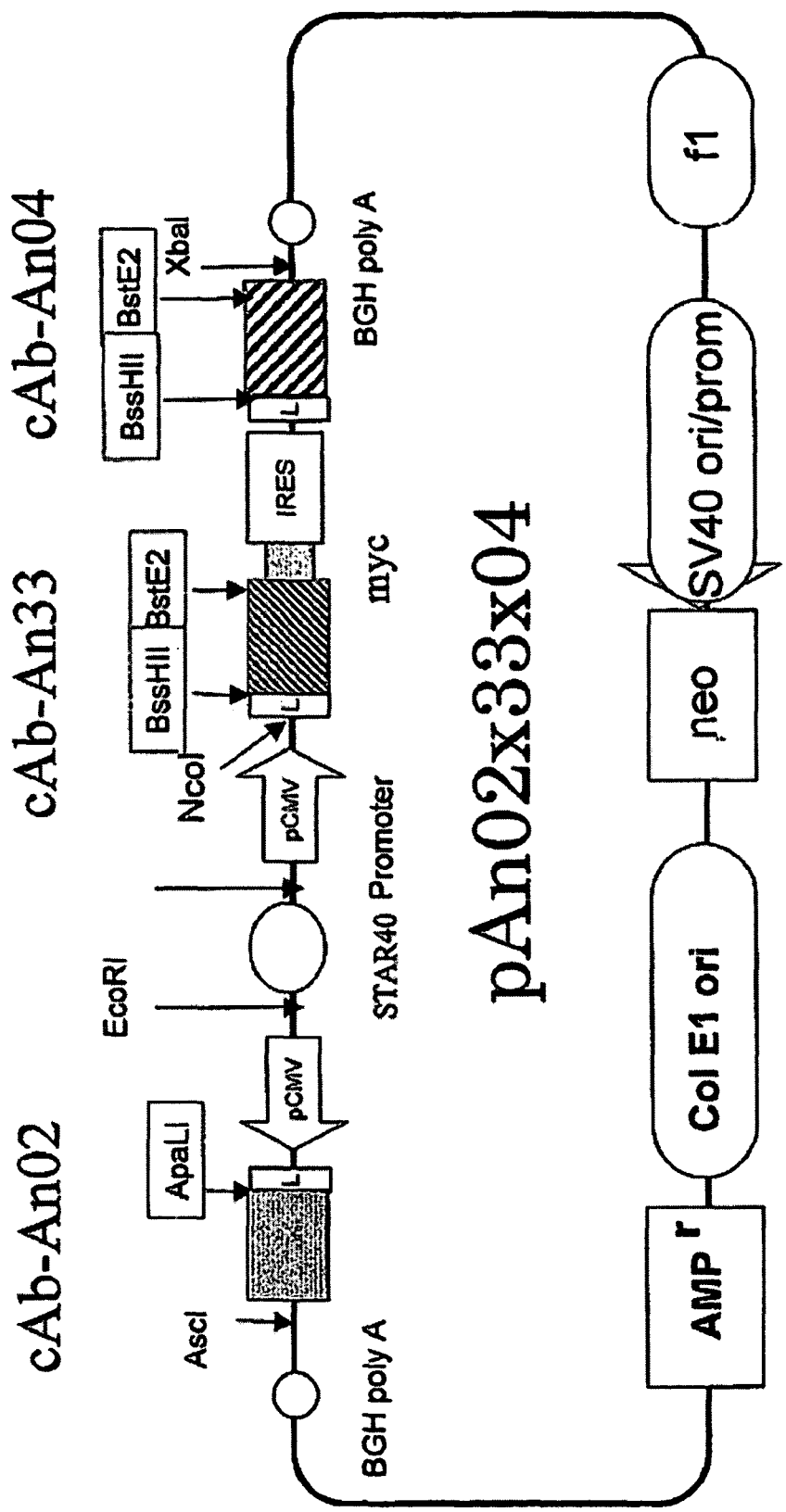
FIG. 8: Plasmid pAn02×33×04 that directs the expression and secretion of three different camelid antibody fragments.

The PCR fragment is digested with ApaLI and AscI and cloned into similarly digested pAn.33×04, to yield now a plasmid with the three camelid SPCBPs, pAn02×33×04, in which cAb-An02 is under control of a separate CMV promoter as the two other cAb coding regions, of cAb33-An04, and in which the expression of these two latter coding regions is linked via an IRES sequence. One of the cAbs, cAb-An33, is also equipped with a myc-tag for rapid detection of the expression of this protein. The plasmid is schematically depicted in FIG. 8.

This plasmid is used for transfection of CHO cells as described in Examples 3 and 4 and cell clones obtained by limiting dilution isolated via the neo-selection marker. Cells expressing at least one cAb are identified by ELISA using coated VSG material. VSG is prepared as follows. Frozen stabilates of *Trypanosoma* brucei brucei bloodstream parasites expressing the respective VSG are expanded by infection of rats (Charles River). Rats with systemic parasitaemia (typically four to five days post infection) are exsanguinated, and parasites are purified from heparinized blood by DEAE-cellulose (DE52, Whatman) chromatography. VSG is then isolated via ion-exchange chromatography and gel filtration (as in B. Stijlemans et al. (2004) *J. Biol. Chem.* 279:1256-1261). For ELISA, VSG (at 1 µg/ml 0.1 M NaHCO$_3$, pH 8.2) is coated overnight (4° C.) to 96-well plates. After blocking (two hours, room temperature) with 5% FCS in PBS, cell supernatants are loaded in 1:2 serial dilutions and bound cAb-An33 is detected using a mouse anti-myc-tag antibody (9E10, Roche, code 1667149) and a goat anti-mouse IgG antibody conjugated to horseradish peroxidase. Thirty minutes after adding peroxidase substrate, the reaction is stopped with 0.1 N H$_2$SO$_4$ and the optical density is measured at 450 nm. Clonal cells reactive with the 9E10 antibody and thus expressing at least cAb-An33, are mixed and expanded for the following transfection. Rather than analyzing the expression of the other 2 cAbs, the cell pool is directly used to introduce additional cAbs via another plasmid transfection.

CAbsAn-05 and -06 are cloned as explained earlier via directional cloning of a PCR fragment equipped with appropriate cloning sites. The cloning vector now is pRRVzeo, which is pRRV in which the neo selection marker has been exchanged by the zeo selection marker from pEM7-zeo (Invitrogen) to be able to select for a new selection marker. In this case both cAbs are provided with a tag, cAb-An05 with a stretch of six histidines (already provided in the phage-display-selected plasmid as tag to all cAbs), and the cAb-An06 with an HA tag (hemagglutin). Antibodies to both of these tags are available by commercial suppliers (Roche, Pharmacia). The resulting plasmid that carries both cAb-An05 and cAb-An06 is designated p05×06. The cell pool that expresses the set of cAbs33/02 and 04 is transfected with p05×06, and clones selected for zeo resistance, while they are also grown on G418-containing medium to select for the presence of the first three cAb coding regions. Multiple stable clones identified after limiting dilutions are expanded. Antigen binding is done as before, but detection is now done in with three different antibodies in parallel, anti-myc (cAb-An33 detection), anti-His (cAb-An05 detection) and anti-HA (cAb-An06 detection). The ELISA result indicates which of the cells are expressing at least one, two or three cAbs (as schematically depicted in FIG. 3). In order to analyze the presence of the other cAbs, Further experiments can first introduce Histidine-tags to all SPCBP coding regions (as done in the earlier examples), such that the group of proteins can be purified by IMAC and analyzed. This will confirm the expression of multiple and up to five different SPCBPs.

What is claimed is:

1. A method for producing a single cell expressing at least two separate a single polypeptide chain binding protein (SPCBP) recognizing a first target epitope and a SPCBP recognizing a second target epitope, wherein binding of each SPCBP to its target epitope is mediated by a single protein domain, wherein the first target epitope and the second target epitope are different from one another, wherein the SPCBP recognizing a first target epitope and a SPCBP recognizing a second target epitope comprise a scaffold domain selected from lipocalin and DigA16, and wherein at least one of the SPCBPs is able to antagonize a function of a target molecule comprising at least one of the first target epitope or the second target epitope, the method comprising:

providing a first library of nucleic acid molecules encoding SPCBPs that recognize the first target epitope, wherein the nucleic acid molecules encoding the SPCBPs are known;

providing a second library of nucleic acid molecules encoding SPCBPs that recognize the second target epitope, wherein the nucleic acid molecules encoding the SPCBPs are known the SPCBP recognizing a first target epitope and a SPCBP recognizing a second target epitope comprise a scaffold domain selected from lipocalin and DigA16;

transfecting cells with the first and second libraries of nucleic acids;

selecting cells from the transfected cells having integrated therein a nucleic acid molecule encoding a SPCBP from the first library and a nucleic acid molecule encoding a SPCBP from the second library into their genomes, thereby producing a first library of cells, wherein each cell in said first library comprises genomic polynucleotides encoding at least a SPCBP recognizing the first target epitope and a SPCBP recognizing the second target epitope;

contacting the first library of cells, or supernatants thereof, with the first target epitope and with the second target epitope;

screening for and selecting cells from the contacted first library of cells, or supernatants thereof, expressing SPCBP able to bind the first target epitope and expressing SPCBP able to bind the second target epitope; thereby producing a second library of cells, wherein each cell in the second library of cells expresses an SPCBP able to bind the first target epitope and expresses a SPCBP able to bind the second target epitope performing a bioassay on the second library of cells, or supernatants thereof, so as to measure antagonistic activity of the SPCBPs against a molecule comprising at least one of the first target epitope or the second target epitope; and selecting based upon the results of the bioassay a cell from the second library that expresses a SPCBP able to antagonize a function of a target molecule comprising at least one of the first target epitope or the second target epitope.

2. A method for producing a single cell expressing at least two separate a single polypeptide chain binding protein (SPCBP) recognizing a first target epitope and a SPCBP recognizing a second target epitope, wherein binding of each SPCBP to its target epitope is mediated by a single protein domain, wherein the first target epitope and the second target epitope are different from one another, wherein the SPCBP recognizing a first target epitope and a SPCBP recognizing a second target epitope comprise a scaffold domain selected from lipocalin and DigA16, and wherein at least one of the SPCBPs is able to activate a function of a target molecule comprising at least one of the first target epitope or the second target epitope, the method comprising:

providing a first library of nucleic acid molecules encoding SPCBPs that recognize the first target epitope, wherein the nucleic acid molecules encoding the SPCBPs are known;

providing a second library of nucleic acid molecules encoding SPCBPs that recognize the second target epitope, wherein the nucleic acid molecules encoding the SPCBPs are known the SPCBP recognizing a first target epitope and a SPCBP recognizing a second target epitope comprise a scaffold domain selected from lipocalin and DigA16;

transfecting cells with the first and second libraries of nucleic acids;

selecting cells from the transfected cells having integrated therein a nucleic acid molecule encoding a SPCBP from the first library and a nucleic acid molecule encoding a SPCBP from the second library into their genomes, thereby producing a first library of cells, wherein each cell in said first library comprises genomic polynucleotides encoding at least a SPCBP recognizing the first target epitope and a SPCBP recognizing the second target epitope;

contacting the first library of cells, or supernatants thereof, with the first target epitope and with the second target epitope;

screening for and selecting cells from the contacted first library of cells, or supernatants thereof, expressing a SPCBP able to bind the first target epitope and expressing a SPCBP able to bind the second target epitope; thereby producing a second library of cells, wherein each cell in the second library of cells expressing a SPCBP able to bind the first target epitope and expresses a SPCBP able to bind the second target epitope;

performing a bioassay on the second library of cells, or supernatants thereof, so as to measure activating activity of the SPCBPs against a molecule comprising at least one of the first target epitope or the second target epitope; and based upon the results of the bioassay, selecting based upon the results of the bioassay a cell from the second library that expresses a SPCBP able to activate a function of a target molecule comprising at least one of the first target epitope or the second target epitope.

3. The method according to claim 1, wherein each cell in the first library of cells expresses the SPCBP recognizing a first target epitope and the SPCBP recognizing a second target epitope at a different ratio.

4. The method according to claim 2, wherein each cell in the first library of cells expresses the SPCBP recognizing a first target epitope and the SPCBP recognizing a second target epitope at a different ratio.

5. The method according to claim 1, wherein the first target epitope and the second target epitope are present on the same target molecule.

6. The method according to claim 2, wherein the first target epitope and the second target epitope are present on the same target molecule.

7. The method according to claim 1, wherein the first target epitope and the second target epitope are present on different target molecules.

8. The method according to claim 2, wherein the first target epitope and the second target epitope are present on different target molecules.

\* \* \* \* \*

SEQUENCE LISTING

<160> NUMBER OF SEQ ID NOS: 11

<210> SEQ ID NO 1
<211> LENGTH: 40
<212> TYPE: DNA
<213> ORGANISM: Artificial Sequence
<220> FEATURE:
<223> OTHER INFORMATION: Primer - SEQ ID NO:1

<400> SEQUENCE: 1
agtgtacagg cgcgcactcc gatgtgcagc tggtggagtc                         40

<210> SEQ ID NO 2
<211> LENGTH: 24
<212> TYPE: DNA
<213> ORGANISM: Artificial Sequence
<220> FEATURE:
<223> OTHER INFORMATION: Primer - SEQ ID NO:2

<400> SEQUENCE: 2
tgaggagacg gtgacctggg tccc                                          24

<210> SEQ ID NO 3
<211> LENGTH: 64
<212> TYPE: DNA
<213> ORGANISM: Artificial Sequence
<220> FEATURE:
<223> OTHER INFORMATION: Primer - SEQ ID NO:3

<400> SEQUENCE: 3
gataaatctg gtcaccgtct cctcagaaca aaaactcatc tcagaagagg atctgaatta   60
ataa                                                                64

<210> SEQ ID NO 4
<211> LENGTH: 40
<212> TYPE: DNA
<213> ORGANISM: Artificial Sequence
<220> FEATURE:
<223> OTHER INFORMATION: Primer - SEQ ID NO:4

<400> SEQUENCE: 4
agtgtacagg cgcgcactcc caggtgcagc tggtggagtc                         40

<210> SEQ ID NO 5
<211> LENGTH: 42
<212> TYPE: DNA
<213> ORGANISM: Artificial Sequence
<220> FEATURE:
<223> OTHER INFORMATION: Primer - SEQ ID NO:5

<400> SEQUENCE: 5
atacgctcta gattagctgg agacggtgac ctgggtcccc gg                      42

<210> SEQ ID NO 6
<211> LENGTH: 41
<212> TYPE: DNA
<213> ORGANISM: Artificial Sequence
<220> FEATURE:
<223> OTHER INFORMATION: Primer - SEQ ID NO:6

<400> SEQUENCE: 6
gcattatctg gcgtgcactc tgatgtgcag ctggtggagt c                       41

<210> SEQ ID NO 7

```
<211> LENGTH: 46
<212> TYPE: DNA
<213> ORGANISM: Artificial Sequence
<220> FEATURE:
<223> OTHER INFORMATION: Primer - SEQ ID NO:7

<400> SEQUENCE: 7
tacagatatg gcgcgcctta tgaggagacg gtgacctggg tcccct          46

<210> SEQ ID NO 8
<211> LENGTH: 121
<212> TYPE: PRT
<213> ORGANISM: Artificial Sequence
<220> FEATURE:
<223> OTHER INFORMATION: Heavy chain variable region amino acid
      sequence

<400> SEQUENCE: 8
```

Gln Val Gln Leu Gln Glu Ser Gly Gly Gly Ser Val Gln Ala Gly Gly
1               5                   10                  15

Ser Leu Arg Leu Ser Cys Ser Ala Ser Gly Tyr Thr Tyr Ile Ser Gly
            20                  25                  30

Trp Phe Arg Gln Ala Pro Gly Lys Glu Arg Glu Gly Val Ala Ala Ile
        35                  40                  45

Arg Ser Ser Asp Gly Thr Thr Tyr Tyr Ala Asp Ser Val Lys Gly Arg
    50                  55                  60

Phe Thr Ile Ser Gln Asp Asn Ala Lys Asn Thr Val Tyr Leu Gln Met
65                  70                  75                  80

Asn Ser Leu Lys Pro Glu Asp Thr Ala Met Tyr Tyr Cys Ala Ala Thr
                85                  90                  95

Glu Val Ala Gly Trp Pro Leu Asp Ile Gly Ile Tyr Asp Tyr Trp Gly
            100                 105                 110

Gln Gly Thr Glu Val Thr Val Ser Ser
        115                 120

```
<210> SEQ ID NO 9
<211> LENGTH: 10
<212> TYPE: PRT
<213> ORGANISM: Artificial Sequence
<220> FEATURE:
<223> OTHER INFORMATION: c-myc tag

<400> SEQUENCE: 9
```

Glu Gln Lys Leu Ile Ser Glu Glu Asp Leu
1               5                   10

```
<210> SEQ ID NO 10
<211> LENGTH: 11
<212> TYPE: PRT
<213> ORGANISM: Artificial Sequence
<220> FEATURE:
<223> OTHER INFORMATION: VSV-tag

<400> SEQUENCE: 10
```

Tyr Thr Asp Ile Glu Met Asn Arg Leu Gly Lys
1               5                   10

```
<210> SEQ ID NO 11
<211> LENGTH: 9
<212> TYPE: PRT
<213> ORGANISM: Artificial Sequence
```

-continued

```
<220> FEATURE:
<223> OTHER INFORMATION: influenza Hemagglutinin (HA)-tag

<400> SEQUENCE: 11

Tyr Pro Tyr Asp Val Pro Asp Tyr Ala
1               5
```